US008658416B2

(12) United States Patent
Church et al.

(10) Patent No.: US 8,658,416 B2
(45) Date of Patent: Feb. 25, 2014

(54) TOXIN-EATING BACTERIA AND BIOREMEDIATION

(75) Inventors: George M. Church, Brookline, MA (US); Gautam Dantas, University City, MO (US); Morten O. Sommer, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 902 days.

(21) Appl. No.: 12/579,696

(22) Filed: Oct. 15, 2009

(65) Prior Publication Data

US 2010/0159565 A1 Jun. 24, 2010

Related U.S. Application Data

(60) Provisional application No. 61/105,614, filed on Oct. 15, 2008.

(51) Int. Cl.
| | |
|---|---|
| *A62D 3/00* | (2007.01) |
| *A62D 3/02* | (2007.01) |
| *B09B 3/00* | (2006.01) |
| *B09C 1/10* | (2006.01) |
| *C02F 3/34* | (2006.01) |

(52) U.S. Cl.
USPC ......... 435/262; 435/262.5; 435/800; 435/822

(58) Field of Classification Search
None
See application file for complete search history.

(56) References Cited

PUBLICATIONS

Abdalem, et al., "Chloramphenicol, a Simultaneous Carbon and Nitrogen Source for a *Streptomyces* sp. from Egyptian Soil." Nature 4766, Mar. 4, 1961.
Davies, "Inactivation of Antibiotics and the Dissemination of Resistance Genes." Science, vol. 264, Apr. 15, 1994.
D'Costa, et al., "Expanding the soil antibiotic resistome:exploring environmental diversity." Current Opinion in Microbiology 2007, 10: 481-489.
Desantis, et al., "NAST:a multiple sequence alignment server for comparative analysis of 16S rRNA genes." Nucleic Acids Research, 2006, vol. 34, W-394-W399.
Fredrickson, et al., "Reduction of Fe(III), Cr(Vi), U(VI), and Te(VII) by *Deinococcus radiodurans* R1." Applied and Environmental Microbiology, May 2000, vol. 66, No. 5, p. 2006-2011.
Johnsen, "Utilization of Benzylpenicillin as Carbon, Nitrogen and Energy Source by a *Pseudomonas fluorescens* Strain." Arch. Microbial. 115, 271-275 (1977).
Kameda, et al.,"A Method for isolating Bacteria capable of producing 6-Aminopenicillanic Acid from Benzylpenicillin." Nature, vol. 191, Sep. 9, 1961.
Marshall, et al., "Glycopeptide Antibiotic Resistance Genes in Glycopeptide-Producing Organisms." Antimicrobial Agents and Chemotherapy, Sep. 1998,vol. 42, No. 9,p. 2215-2220.
McAllister, et al., "Microbial degradation of pentachlorphenol." Biodegradation 7, 1-40, 1996.
Parke, et al., "Diversity of the *Burkholderia cepacia complex* and Implications for Risk Assessment of Biological Control Strains." Ann. Rev. Phytopathol. 2001 39:225-258.
Projan, "Guest Commentary (Genome) Size Matters." Antimicrobial Agents and Chemotherapy, Apr. 2007, vol. 51, No. 4,p. 1133-1134.
Alekshun, et al., "Molecular Mechanisms of Antibacterial Multidrug Resistance." Cell 128, Mar. 23, 2007.
Riesenfeld, et al., "Uncultured soil bacteria are a reservoir of new antibiotic resistance genes." Environmental Microbiology (2004) vol. 6, No. 9, p. 981-989.
Cole, et al., "The ribosomal database project (RDP-II):introducing myRDP space and quality controlled public data." Nucleic Acids Research, 2007, vol. 35, Database issue D169-D172.
D'Costa, et al., "Sampling the Antibiotic Resistome." Science, vol. 311, Jan. 20, 2006.
Desantis, et al., "Greengenes, a Chimera-Checked 16S rRNA Gene Database and Workbench Compatible with ARB." Applied Environmental Microbiology, Jul. 2006, vol. 72, No. 7,p. 5069-5072.
Mikrobiologie, et al., "ARB: a software environment for sequence data." Nucleic Acids Research, 2004, vol. 32, No. 4, p. 1363-1371.
Walsh, "Molecular mechanisms that confer antibacterial drug resistance." Nature, vol. 406, Aug. 17, 2000.
Wheeler, et al., "Database resources of the National Center for Biotechnology Information." Nucleic Acids Research, 2000, vol. 28, No. 1.

*Primary Examiner* — Debbie K Ware
(74) *Attorney, Agent, or Firm* — Banner & Witcoff, Ltd.

(57) ABSTRACT

Methods are provided for reducing a level of one or more antibiotics from an antibiotic-contaminated substance. An organism that can utilize the one or more antibiotics as a carbon source is cultured in the presence of the antibiotic-contaminated substance for a sufficient amount of time to reduce the level of one or more antibiotics from the antibiotic-contaminated substance.

12 Claims, 39 Drawing Sheets
(5 of 39 Drawing Sheet(s) Filed in Color)

| Box | S* | Strain | Label | Source | Media | Temp | Oxygen | Extraction | Date |
|---|---|---|---|---|---|---|---|---|---|
| AIB2 | A1 | CIPRO S2TM1LLLSSL1 | CIPRO S2TM1LLLSSL1 | Soil 2 from 2 mixed forest area, PA | YDM-TM | RT | Yes | N/A | 8/3/2007 |
| AIB3 | A2 | CIPRO S2TM1LLLSSL2 | CIPRO S2TM1LLLSSL2 | Soil 2 from 2 mixed forest area, PA | YDM-TM | RT | Yes | N/A | 8/3/2007 |
| AIB4 | A3 | CIPRO S2TM1LLLSSL3 | CIPRO S2TM1LLLSSL3 | Soil 2 from 2 mixed forest area, PA | YDM-TM | RT | Yes | N/A | 8/3/2007 |
| AIB5 | A4 | LEVO S2TM1LLLSSL 1 | LEVO S2TM1LLLSSL 1 | Soil 2 from 2 mixed forest area, PA | YDM-TM | RT | Yes | N/A | 8/3/2007 |
| AIB6 | A5 | LEVO S2TM1LLLSSL 2 | LEVO S2TM1LLLSSL 2 | Soil 2 from 2 mixed forest area, PA | YDM-TM | RT | Yes | N/A | 8/3/2007 |
| AIB7 | A6 | LEVO S2TM1LLLSSL 3 | LEVO S2TM1LLLSSL 3 | Soil 2 from 2 mixed forest area, PA | YDM-TM | RT | Yes | N/A | 8/3/2007 |
| AIB8 | A7 | SISO S2TM1LLLSSL 1 | SISO S2TM1LLLSSL 1 | Soil 2 from 2 mixed forest area, PA | YDM-TM | RT | Yes | N/A | 8/3/2007 |
| AIB9 | A8 | SISO S2TM1LLLSSL 2 | SISO S2TM1LLLSSL 2 | Soil 2 from 2 mixed forest area, PA | YDM-TM | RT | Yes | N/A | 8/3/2007 |
| AIB10 | A9 | SISOMICIN S2TM1LLLSSL 3 | SISOMICIN S2TM1LLLSSL 3 | Soil 2 from 2 mixed forest area, PA | YDM-TM | RT | Yes | N/A | 8/3/2007 |
| AIB11 | A10 | GENTAMICIN S2TM1LLLSSL 1 | GENTAMICIN S2TM1LLLSSL 1 | Soil 2 from 2 mixed forest area, PA | YDM-TM | RT | Yes | N/A | 8/3/2007 |
| AIB12 | B1 | GENTAMICIN S2TM1LLLSSL 2 | GENTAMICIN S2TM1LLLSSL 2 | Soil 2 from 2 mixed forest area, PA | YDM-TM | RT | Yes | N/A | 8/3/2007 |
| AIB13 | B2 | GENTAMICIN S2TM1LLLSSL 3 | GENTAMICIN S2TM1LLLSSL 3 | Soil 2 from 2 mixed forest area, PA | YDM-TM | RT | Yes | N/A | 8/3/2007 |
| AIB14 | B3 | KANAMICIN S2TM1LLLSSL 1 | KANAMICIN S2TM1LLLSSL 1 | Soil 2 from 2 mixed forest area, PA | YDM-TM | RT | Yes | N/A | 8/3/2007 |
| AIB15 | B4 | KANAMICIN S2TM1LLLSSL 2 | KANAMICIN S2TM1LLLSSL 2 | Soil 2 from 2 mixed forest area, PA | YDM-TM | RT | Yes | N/A | 8/3/2007 |
| AIB16 | B5 | KANAMICIN S2TM1LLLSSL 3 | KANAMICIN S2TM1LLLSSL 3 | Soil 2 from 2 mixed forest area, PA | YDM-TM | RT | Yes | N/A | 8/3/2007 |
| AIB17 | B6 | AMIKACIN S2TM1LLLSSL 1 | AMIKACIN S2TM1LLLSSL 1 | Soil 2 from 2 mixed forest area, PA | YDM-TM | RT | Yes | N/A | 8/3/2007 |
| AIB18 | B7 | AMIKACIN S2TM1LLLSSL 2 | AMIKACIN S2TM1LLLSSL 2 | Soil 2 from 2 mixed forest area, PA | YDM-TM | RT | Yes | N/A | 8/3/2007 |
| AIB19 | B8 | AMIKACIN S2TM1LLLSSL 3 | AMIKACIN S2TM1LLLSSL 3 | Soil 2 from 2 mixed forest area, PA | YDM-TM | RT | Yes | N/A | 8/3/2007 |
| AIB20 | B9 | PENICILLIN G S2TM1LLLSSL 1 | PENICILLIN G S2TM1LLLSSL 1 | Soil 2 from 2 mixed forest area, PA | YDM-TM | RT | Yes | N/A | 8/3/2007 |
| AIB21 | B10 | PENICILLIN G S2TM1LLLSSL 2 | PENICILLIN G S2TM1LLLSSL 2 | Soil 2 from 2 mixed forest area, PA | YDM-TM | RT | Yes | N/A | 8/3/2007 |
| AIB22 | C1 | PENICILLIN G S2TM1LLLSSL 3 | PENICILLIN G S2TM1LLLSSL 3 | Soil 2 from 2 mixed forest area, PA | YDM-TM | RT | Yes | N/A | 8/3/2007 |
| AIB23 | C2 | CARBENICILLIN S2TM1LLLSSL 1 | CARBENICILLIN S2TM1LLLSSL 1 | Soil 2 from 2 mixed forest area, PA | YDM-TM | RT | Yes | N/A | 8/3/2007 |

Figure 7

| | | | | | | | |
|---|---|---|---|---|---|---|---|
| AIB24 | C3 | CARBENICILLIN S2TM1LLLSSL 2 | CARBENICILLIN S2TM1LLLSSL 2 | Soil 2 from 2 mixed forest area, PA | YDM-TM | RT | Yes | N/A | 8/3/2007 |
| AIB25 | C4 | CARBENICILLIN S2TM1LLLSSL 3 | CARBENICILLIN S2TM1LLLSSL 3 | Soil 2 from 2 mixed forest area, PA | YDM-TM | RT | Yes | N/A | 8/3/2007 |
| AIB26 | C5 | DICLO S2TM1LLLSSL 1 | DICLO S2TM1LLLSSL 1 | Soil 2 from 2 mixed forest area, PA | YDM-TM | RT | Yes | N/A | 8/3/2007 |
| AIB27 | C6 | DICLO S2TM1LLLSSL 2 | DICLO S2TM1LLLSSL 2 | Soil 2 from 2 mixed forest area, PA | YDM-TM | RT | Yes | N/A | 8/3/2007 |
| AIB28 | C7 | DICLO S2TM1LLLSSL 3 | DICLO S2TM1LLLSSL 3 | Soil 2 from 2 mixed forest area, PA | YDM-TM | RT | Yes | N/A | 8/3/2007 |
| AIB29 | C8 | CHLORAM S2TM1LLLSSL 1 | CHLORAM S2TM1LLLSSL 1 | Soil 2 from 2 mixed forest area, PA | YDM-TM | RT | Yes | N/A | 8/3/2007 |
| AIB30 | C9 | CHLORAM S2TM1LLLSSL 2 | CHLORAM S2TM1LLLSSL 2 | Soil 2 from 2 mixed forest area, PA | YDM-TM | RT | Yes | N/A | 8/3/2007 |
| AIB31 | C10 | CHLORAM S2TM1LLLSSL 3 | CHLORAM S2TM1LLLSSL 3 | Soil 2 from 2 mixed forest area, PA | YDM-TM | RT | Yes | N/A | 8/3/2007 |
| AIB32 | D1 | NALIDIXIC S2TM1LLLSSL 1 | NALIDIXIC S2TM1LLLSSL 1 | Soil 2 from 2 mixed forest area, PA | YDM-TM | RT | Yes | N/A | 8/3/2007 |
| AIB33 | D2 | NALIDIXIC S2TM1LLLSSL 2 | NALIDIXIC S2TM1LLLSSL 2 | Soil 2 from 2 mixed forest area, PA | YDM-TM | RT | Yes | N/A | 8/3/2007 |
| AIB34 | D3 | NALIDIXIC S2TM1LLLSSL 3 | NALIDIXIC S2TM1LLLSSL 3 | Soil 2 from 2 mixed forest area, PA | YDM-TM | RT | Yes | N/A | 8/3/2007 |
| AIB35 | D4 | THIAMPHENI S2TM1LLLSSL 1 | THIAMPHENI S2TM1LLLSSL 1 | Soil 2 from 2 mixed forest area, PA | YDM-TM | RT | Yes | N/A | 8/3/2007 |
| AIB36 | D5 | THIAMPHENI S2TM1LLLSSL 2 | THIAMPHENI S2TM1LLLSSL 2 | Soil 2 from 2 mixed forest area, PA | YDM-TM | RT | Yes | N/A | 8/3/2007 |
| AIB37 | D6 | THIAMPHENI S2TM1LLLSSL 3 | THIAMPHENI S2TM1LLLSSL 3 | Soil 2 from 2 mixed forest area, PA | YDM-TM | RT | Yes | N/A | 8/3/2007 |
| AIB38 | D7 | TRIMETHO S2TM1LLLSSL 1 | TRIMETHO S2TM1LLLSSL 1 | Soil 2 from 2 mixed forest area, PA | YDM-TM | RT | Yes | N/A | 8/3/2007 |
| AIB39 | D8 | TRIMETHO S2TM1LLLSSL 2 | TRIMETHO S2TM1LLLSSL 2 | Soil 2 from 2 mixed forest area, PA | YDM-TM | RT | Yes | N/A | 8/3/2007 |
| AIB40 | D9 | TRIMETHO S2TM1LLLSSL 3 | TRIMETHO S2TM1LLLSSL 3 | Soil 2 from 2 mixed forest area, PA | YDM-TM | RT | Yes | N/A | 8/3/2007 |
| AIB41 | D10 | MAFENIDE S2TM1LLLSSL 1 | MAFENIDE S2TM1LLLSSL 1 | Soil 2 from 2 mixed forest area, PA | YDM-TM | RT | Yes | N/A | 8/3/2007 |
| AIB42 | E1 | MAFENIDE S2TM1LLLSSL 2 | MAFENIDE S2TM1LLLSSL 2 | Soil 2 from 2 mixed forest area, PA | YDM-TM | RT | Yes | N/A | 8/3/2007 |
| AIB43 | E2 | MAFENIDE S2TM1LLLSSL 3 | MAFENIDE S2TM1LLLSSL 3 | Soil 2 from 2 mixed forest area, PA | YDM-TM | RT | Yes | N/A | 8/3/2007 |
| AIB44 | E3 | SULFAMET S2TM1LLLSSL 1 | SULFAMET S2TM1LLLSSL 1 | Soil 2 from 2 mixed forest area, PA | YDM-TM | RT | Yes | N/A | 8/3/2007 |
| AIB45 | E4 | SULFAMET S2TM1LLLSSL 2 | SULFAMET S2TM1LLLSSL 2 | Soil 2 from 2 mixed forest area, PA | YDM-TM | RT | Yes | N/A | 8/3/2007 |
| AIB46 | E5 | SULFAMET S2TM1LLLSSL 3 | SULFAMET S2TM1LLLSSL 3 | Soil 2 from 2 mixed forest area, PA | YDM-TM | RT | Yes | N/A | 8/3/2007 |

Figure 7 (Cont.)

| | | | | | | | |
|---|---|---|---|---|---|---|---|
| AIB47 | E6 | TETRA S2TM1LLLSSL 1 | TETRA S2TM1LLLSSL 1 | Soil 2 from 2 mixed forest area, PA | YDM-TM | RT | Yes | N/A | 8/3/2007 |
| AIB48 | E7 | TETRA S2TM1LLLSSL 2 | TETRA S2TM1LLLSSL 2 | Soil 2 from 2 mixed forest area, PA | YDM-TM | RT | Yes | N/A | 8/3/2007 |
| AIB49 | E8 | TETRA S2TM1LLLSSL 3 | TETRA S2TM1LLLSSL 3 | Soil 2 from 2 mixed forest area, PA | YDM-TM | RT | Yes | N/A | 8/3/2007 |
| AIB50 | E9 | OXYTET S2TM1LLLSSL 1 | OXYTET S2TM1LLLSSL 1 | Soil 2 from 2 mixed forest area, PA | YDM-TM | RT | Yes | N/A | 8/3/2007 |
| AIB51 | E10 | OXYTET S2TM1LLLSSL 2 | OXYTET S2TM1LLLSSL 2 | Soil 2 from 2 mixed forest area, PA | YDM-TM | RT | Yes | N/A | 8/3/2007 |
| AIB52 | F1 | OXYTET S2TM1LLLSSL 3 | OXYTET S2TM1LLLSSL 3 | Soil 2 from 2 mixed forest area, PA | YDM-TM | RT | Yes | N/A | 8/3/2007 |
| AIB53 | F2 | MINOCY S2TM1LLLSSL 1 | MINOCY S2TM1LLLSSL 1 | Soil 2 from 2 mixed forest area, PA | YDM-TM | RT | Yes | N/A | 8/3/2007 |
| AIB54 | F3 | MINOCY S2TM1LLLSSL 2 | MINOCY S2TM1LLLSSL 2 | Soil 2 from 2 mixed forest area, PA | YDM-TM | RT | Yes | N/A | 8/3/2007 |
| AIB55 | F4 | MINOCY S2TM1LLLSSL 3 | MINOCY S2TM1LLLSSL 3 | Soil 2 from 2 mixed forest area, PA | YDM-TM | RT | Yes | N/A | 8/3/2007 |
| AIB56 | F5 | D-CYCLO S2TM1LLLSSL 1 | D-CYCLO S2TM1LLLSSL 1 | Soil 2 from 2 mixed forest area, PA | YDM-TM | RT | Yes | N/A | 8/3/2007 |
| AIB57 | F6 | D-CYCLO S2TM1LLLSSL 2 | D-CYCLO S2TM1LLLSSL 2 | Soil 2 from 2 mixed forest area, PA | YDM-TM | RT | Yes | N/A | 8/3/2007 |
| AIB58 | F7 | D-CYCLO S2TM1LLLSSL 3 | D-CYCLO S2TM1LLLSSL 3 | Soil 2 from 2 mixed forest area, PA | YDM-TM | RT | Yes | N/A | 8/3/2007 |
| AIB59 | F8 | VANCO S2TM1LLLSSL 1 | VANCO S2TM1LLLSSL 1 | Soil 2 from 2 mixed forest area, PA | YDM-TM | RT | Yes | N/A | 8/3/2007 |
| AIB60 | F9 | VANCO S2TM1LLLSSL 2 | VANCO S2TM1LLLSSL 2 | Soil 2 from 2 mixed forest area, PA | YDM-TM | RT | Yes | N/A | 8/3/2007 |
| AIB61 | F10 | VANCO S2TM1LLLSSL 3 | VANCO S2TM1LLLSSL 3 | Soil 2 from 2 mixed forest area, PA | YDM-TM | RT | Yes | N/A | 8/3/2007 |
| AIB62 | G1 | CIPRO S2NM1LLLSSL1 | CIPRO S2NM1LLLSSL1 | Soil 2 from Alfalfa without manure, MN | YDM-TM | RT | Yes | N/A | 8/3/2007 |
| AIB63 | G2 | CIPRO S2NM1LLLSSL2 | CIPRO S2NM1LLLSSL2 | Soil 2 from Alfalfa without manure, MN | YDM-TM | RT | Yes | N/A | 8/3/2007 |
| AIB64 | G3 | CIPRO S2NM1LLLSSL3 | CIPRO S2NM1LLLSSL3 | Soil 2 from Alfalfa without manure, MN | YDM-TM | RT | Yes | N/A | 8/3/2007 |
| AIB65 | G4 | LEVO S2NM1LLLSSL 1 | LEVO S2NM1LLLSSL 1 | Soil 2 from Alfalfa without manure, MN | YDM-TM | RT | Yes | N/A | 8/3/2007 |
| AIB66 | G5 | LEVO S2NM1LLLSSL 2 | LEVO S2NM1LLLSSL 2 | Soil 2 from Alfalfa without manure, MN | YDM-TM | RT | Yes | N/A | 8/3/2007 |
| AIB67 | G6 | LEVO S2NM1LLLSSL 3 | LEVO S2NM1LLLSSL 3 | Soil 2 from Alfalfa without manure, MN | YDM-TM | RT | Yes | N/A | 8/3/2007 |
| AIB68 | G7 | SISO S2NM1LLLSSL 1 | SISO S2NM1LLLSSL 1 | Soil 2 from Alfalfa without manure, MN | YDM-TM | RT | Yes | N/A | 8/3/2007 |
| AIB69 | G8 | SISO S2NM1LLLSSL 2 | SISO S2NM1LLLSSL 2 | Soil 2 from Alfalfa without manure, MN | YDM-TM | RT | Yes | N/A | 8/3/2007 |

Figure 7 (Cont.)

| | | | | | | | |
|---|---|---|---|---|---|---|---|
| AIB70 | G9 | SISO S2NM1LLLSSL 3 | SISO S2NM1LLLSSL 3 | Soil 2 from Alfalfa without manure, MN | YDM-TM | RT | Yes | N/A | 8/3/2007 |
| AIB71 | G10 | GENTAMICIN S2NM1LLLSSL 1 | GENTAMICIN S2NM1LLLSSL 1 | Soil 2 from Alfalfa without manure, MN | YDM-TM | RT | Yes | N/A | 8/3/2007 |
| AIB72 | H1 | GENTAMICIN S2NM1LLLSSL 2 | GENTAMICIN S2NM1LLLSSL 2 | Soil 2 from Alfalfa without manure, MN | YDM-TM | RT | Yes | N/A | 8/3/2007 |
| AIB73 | H2 | GENTAMICIN S2NM1LLLSSL 3 | GENTAMICIN S2NM1LLLSSL 3 | Soil 2 from Alfalfa without manure, MN | YDM-TM | RT | Yes | N/A | 8/3/2007 |
| AIB74 | H3 | KANAMICIN S2NM1LLLSSL 1 | KANAMICIN S2NM1LLLSSL 1 | Soil 2 from Alfalfa without manure, MN | YDM-TM | RT | Yes | N/A | 8/3/2007 |
| AIB75 | H4 | KANAMICIN S2NM1LLLSSL 2 | KANAMICIN S2NM1LLLSSL 2 | Soil 2 from Alfalfa without manure, MN | YDM-TM | RT | Yes | N/A | 8/3/2007 |
| AIB76 | H5 | KANAMICIN S2NM1LLLSSL 3 | KANAMICIN S2NM1LLLSSL 3 | Soil 2 from Alfalfa without manure, MN | YDM-TM | RT | Yes | N/A | 8/3/2007 |
| AIB77 | H6 | AMIKACIN S2NM1LLLSSL 1 | AMIKACIN S2NM1LLLSSL 1 | Soil 2 from Alfalfa without manure, MN | YDM-TM | RT | Yes | N/A | 8/3/2007 |
| AIB78 | H7 | AMIKACIN S2NM1LLLSSL 2 | AMIKACIN S2NM1LLLSSL 2 | Soil 2 from Alfalfa without manure, MN | YDM-TM | RT | Yes | N/A | 8/3/2007 |
| AIB79 | H8 | AMIKACIN S2NM1LLLSSL 3 | AMIKACIN S2NM1LLLSSL 3 | Soil 2 from Alfalfa without manure, MN | YDM-TM | RT | Yes | N/A | 8/3/2007 |
| AIB80 | H9 | PENICILLIN G S2NM1LLLSSL 1 | PENICILLIN G S2NM1LLLSSL 1 | Soil 2 from Alfalfa without manure, MN | YDM-TM | RT | Yes | N/A | 8/3/2007 |
| AIB81 | H10 | PENICILLIN G S2NM1LLLSSL 2 | PENICILLIN G S2NM1LLLSSL 2 | Soil 2 from Alfalfa without manure, MN | YDM-TM | RT | Yes | N/A | 8/3/2007 |
| AIB82 | I1 | PENICILLIN G S2NM1LLLSSL 3 | PENICILLIN G S2NM1LLLSSL 3 | Soil 2 from Alfalfa without manure, MN | YDM-TM | RT | Yes | N/A | 8/3/2007 |
| AIB83 | I2 | CARBENICILLIN S2NM1LLLSSL 1 | CARBENICILLIN S2NM1LLLSSL 1 | Soil 2 from Alfalfa without manure, MN | YDM-TM | RT | Yes | N/A | 8/3/2007 |
| AIB84 | I3 | CARBENICILLIN S2NM1LLLSSL 2 | CARBENICILLIN S2NM1LLLSSL 2 | Soil 2 from Alfalfa without manure, MN | YDM-TM | RT | Yes | N/A | 8/3/2007 |
| AIB85 | I4 | CARBENICILLIN S2NM1LLLSSL 3 | CARBENICILLIN S2NM1LLLSSL 3 | Soil 2 from Alfalfa without manure, MN | YDM-TM | RT | Yes | N/A | 8/3/2007 |
| AIB86 | I5 | DICLO S2NM1LLLSSL 1 | DICLO S2NM1LLLSSL 1 | Soil 2 from Alfalfa without manure, MN | YDM-TM | RT | Yes | N/A | 8/3/2007 |
| AIB87 | I6 | DICLO S2NM1LLLSSL 2 | DICLO S2NM1LLLSSL 2 | Soil 2 from Alfalfa without manure, MN | YDM-TM | RT | Yes | N/A | 8/3/2007 |
| AIB88 | I7 | DICLO S2NM1LLLSSL 3 | DICLO S2NM1LLLSSL 3 | Soil 2 from Alfalfa without manure, MN | YDM-TM | RT | Yes | N/A | 8/3/2007 |
| AIB89 | I8 | CHLORAM S2NM1LLLSSL 1 | CHLORAM S2NM1LLLSSL 1 | Soil 2 from Alfalfa without manure, MN | YDM-TM | RT | Yes | N/A | 8/3/2007 |
| AIB90 | I9 | CHLORAM S2NM1LLLSSL 2 | CHLORAM S2NM1LLLSSL 2 | Soil 2 from Alfalfa without manure, MN | YDM-TM | RT | Yes | N/A | 8/3/2007 |
| AIB91 | I10 | CHLORAM S2NM1LLLSSL 3 | CHLORAM S2NM1LLLSSL 3 | Soil 2 from Alfalfa without manure, MN | YDM-TM | RT | Yes | N/A | 8/3/2007 |
| AIB92 | J1 | NALIDIXIC S2NM1LLLSSL 1 | NALIDIXIC S2NM1LLLSSL 1 | Soil 2 from Alfalfa without manure, MN | YDM-TM | RT | Yes | N/A | 8/3/2007 |

Figure 7 (Cont.)

| | | | | | | | |
|---|---|---|---|---|---|---|---|
| AIB93 | J2 | NALIDIXIC S2NM1LLLSSL 2 | NALIDIXIC S2NM1LLLSSL 2 | Soil 2 from Alfalfa without manure, MN | YDM-TM | RT | Yes | N/A | 8/3/2007 |
| AIB94 | J3 | NALIDIXIC S2NM1LLLSSL 3 | NALIDIXIC S2NM1LLLSSL 3 | Soil 2 from Alfalfa without manure, MN | YDM-TM | RT | Yes | N/A | 8/3/2007 |
| AIB95 | J4 | THIAMPHENI S2NM1LLLSSL 1 | THIAMPHENI S2NM1LLLSSL 1 | Soil 2 from Alfalfa without manure, MN | YDM-TM | RT | Yes | N/A | 8/3/2007 |
| AIB96 | J5 | THIAMPHENI S2NM1LLLSSL 2 | THIAMPHENI S2NM1LLLSSL 2 | Soil 2 from Alfalfa without manure, MN | YDM-TM | RT | Yes | N/A | 8/3/2007 |
| AIB97 | J6 | THIAMPHENI S2NM1LLLSSL 3 | THIAMPHENI S2NM1LLLSSL 3 | Soil 2 from Alfalfa without manure, MN | YDM-TM | RT | Yes | N/A | 8/3/2007 |
| AIB98 | J7 | TRIMETHO S2NM1LLLSSL 1 | TRIMETHO S2NM1LLLSSL 1 | Soil 2 from Alfalfa without manure, MN | YDM-TM | RT | Yes | N/A | 8/3/2007 |
| AIB99 | J8 | TRIMETHO S2NM1LLLSSL 2 | TRIMETHO S2NM1LLLSSL 2 | Soil 2 from Alfalfa without manure, MN | YDM-TM | RT | Yes | N/A | 8/3/2007 |
| AIB100 | J9 | TRIMETHO S2NM1LLLSSL 3 | TRIMETHO S2NM1LLLSSL 3 | Soil 2 from Alfalfa without manure, MN | YDM-TM | RT | Yes | N/A | 8/3/2007 |
| AIB101 | J10 | MAFENIDE S2NM1LLLSSL 1 | MAFENIDE S2NM1LLLSSL 1 | Soil 2 from Alfalfa without manure, MN | YDM-TM | RT | Yes | N/A | 8/3/2007 |

Figure 7 (Cont.)

| Box | S* | Strain | Label | Source | Media | Temp | Oxygen | Extr | Date |
|---|---|---|---|---|---|---|---|---|---|
| A1B3 | A1 | MAFENIDE S2NM1LLLSSL 2 | MAFENIDE S2NM1LLLSSL 2 | Soil 2 from Alfalfa without manure, MN | YDM-TM | RT | Yes | N/A | 8/3/2007 |
| A1B3 | A2 | MAFENIDE S2NM1LLLSSL 3 | MAFENIDE S2NM1LLLSSL 3 | Soil 2 from Alfalfa without manure, MN | YDM-TM | RT | Yes | N/A | 8/3/2007 |
| A1B3 | A3 | SULFAMET S2NM1LLLSSL 1 | SULFAMET S2NM1LLLSSL 1 | Soil 2 from Alfalfa without manure, MN | YDM-TM | RT | Yes | N/A | 8/3/2007 |
| A1B3 | A4 | SULFAMET S2NM1LLLSSL 2 | SULFAMET S2NM1LLLSSL 2 | Soil 2 from Alfalfa without manure, MN | YDM-TM | RT | Yes | N/A | 8/3/2007 |
| A1B3 | A5 | SULFAMET S2NM1LLLSSL 3 | SULFAMET S2NM1LLLSSL 3 | Soil 2 from Alfalfa without manure, MN | YDM-TM | RT | Yes | N/A | 8/3/2007 |
| A1B3 | A6 | TETRA S2NM1LLLSSL 1 | TETRA S2NM1LLLSSL 1 | Soil 2 from Alfalfa without manure, MN | YDM-TM | RT | Yes | N/A | 8/3/2007 |
| A1B3 | A7 | TETRA S2NM1LLLSSL 2 | TETRA S2NM1LLLSSL 2 | Soil 2 from Alfalfa without manure, MN | YDM-TM | RT | Yes | N/A | 8/3/2007 |
| A1B3 | A8 | TETRA S2NM1LLLSSL 3 | TETRA S2NM1LLLSSL 3 | Soil 2 from Alfalfa without manure, MN | YDM-TM | RT | Yes | N/A | 8/3/2007 |
| A1B3 | A9 | OXYTET S2NM1LLLSSL 1 | OXYTET S2NM1LLLSSL 1 | Soil 2 from Alfalfa without manure, MN | YDM-TM | RT | Yes | N/A | 8/3/2007 |
| A1B3 | A10 | OXYTET S2NM1LLLSSL 2 | OXYTET S2NM1LLLSSL 2 | Soil 2 from Alfalfa without manure, MN | YDM-TM | RT | Yes | N/A | 8/3/2007 |
| A1B3 | B1 | OXYTET S2NM1LLLSSL 3 | OXYTET S2NM1LLLSSL 3 | Soil 2 from Alfalfa without manure, MN | YDM-TM | RT | Yes | N/A | 8/3/2007 |
| A1B3 | B2 | VANCO S2NM1LLLSSL 1 | VANCO S2NM1LLLSSL 1 | Soil 2 from Alfalfa without manure, MN | YDM-TM | RT | Yes | N/A | 8/3/2007 |
| A1B3 | B3 | VANCO S2NM1LLLSSL 2 | VANCO S2NM1LLLSSL 2 | Soil 2 from Alfalfa without manure, MN | YDM-TM | RT | Yes | N/A | 8/3/2007 |
| A1B3 | B4 | VANCO S2NM1LLLSSL 3 | VANCO S2NM1LLLSSL 3 | Soil 2 from Alfalfa without manure, MN | YDM-TM | RT | Yes | N/A | 8/3/2007 |
| A1B3 | B5 | CIPRO S3NM1LLLSSL1 | CIPRO S3NM1LLLSSL1 | Soil 3 from Prairie, MN | YDM-TM | RT | Yes | N/A | 8/3/2007 |
| A1B3 | B6 | CIPRO S3NM1LLLSSL2 | CIPRO S3NM1LLLSSL2 | Soil 3 from Prairie, MN | YDM-TM | RT | Yes | N/A | 8/3/2007 |
| A1B3 | B7 | CIPRO S3NM1LLLSSL3 | CIPRO S3NM1LLLSSL3 | Soil 3 from Prairie, MN | YDM-TM | RT | Yes | N/A | 8/3/2007 |
| A1B3 | B8 | LEVO S3NM1LLLSSL 1 | LEVO S3NM1LLLSSL 1 | Soil 3 from Prairie, MN | YDM-TM | RT | Yes | N/A | 8/3/2007 |
| A1B3 | B9 | LEVO S3NM1LLLSSL 2 | LEVO S3NM1LLLSSL 2 | Soil 3 from Prairie, MN | YDM-TM | RT | Yes | N/A | 8/3/2007 |
| A1B3 | B10 | LEVO S3NM1LLLSSL 3 | LEVO S3NM1LLLSSL 3 | Soil 3 from Prairie, MN | YDM-TM | RT | Yes | N/A | 8/3/2007 |
| A1B3 | C1 | SISO S3NM1LLLSSL 1 | SISO S3NM1LLLSSL 1 | Soil 3 from Prairie, MN | YDM-TM | RT | Yes | N/A | 8/3/2007 |
| A1B3 | C2 | SISO S3NM1LLLSSL 2 | SISO S3NM1LLLSSL 2 | Soil 3 from Prairie, MN | YDM-TM | RT | Yes | N/A | 8/3/2007 |

Figure 8

| | | | | | | | |
|---|---|---|---|---|---|---|---|
| AIB3 | C3 | SISO S3NM1LLLSSL 3 | SISO S3NM1LLLSSL 3 | Soil 3 from Prairie, MN | YDM-TM | RT | Yes | N/A | 8/3/2007 |
| AIB3 | C4 | GENTAMICIN S3NM1LLLSSL 1 | GENTAMICIN S3NM1LLLSSL 1 | Soil 3 from Prairie, MN | YDM-TM | RT | Yes | N/A | 8/3/2007 |
| AIB3 | C5 | GENTAMICIN S3NM1LLLSSL 2 | GENTAMICIN S3NM1LLLSSL 2 | Soil 3 from Prairie, MN | YDM-TM | RT | Yes | N/A | 8/3/2007 |
| AIB3 | C6 | GENTAMICIN S3NM1LLLSSL 3 | GENTAMICIN S3NM1LLLSSL 3 | Soil 3 from Prairie, MN | YDM-TM | RT | Yes | N/A | 8/3/2007 |
| AIB3 | C7 | KANAMICIN S3NM1LLLSSL 1 | KANAMICIN S3NM1LLLSSL 1 | Soil 3 from Prairie, MN | YDM-TM | RT | Yes | N/A | 8/3/2007 |
| AIB3 | C8 | KANAMICIN S3NM1LLLSSL 2 | KANAMICIN S3NM1LLLSSL 2 | Soil 3 from Prairie, MN | YDM-TM | RT | Yes | N/A | 8/3/2007 |
| AIB3 | C9 | KANAMICIN S3NM1LLLSSL 3 | KANAMICIN S3NM1LLLSSL 3 | Soil 3 from Prairie, MN | YDM-TM | RT | Yes | N/A | 8/3/2007 |
| AIB3 | C10 | AMIKACIN S3NM1LLLSSL 1 | AMIKACIN S3NM1LLLSSL 1 | Soil 3 from Prairie, MN | YDM-TM | RT | Yes | N/A | 8/3/2007 |
| AIB3 | D1 | AMIKACIN S3NM1LLLSSL 2 | AMIKACIN S3NM1LLLSSL 2 | Soil 3 from Prairie, MN | YDM-TM | RT | Yes | N/A | 8/3/2007 |
| AIB3 | D2 | AMIKACIN S3NM1LLLSSL 3 | AMIKACIN S3NM1LLLSSL 3 | Soil 3 from Prairie, MN | YDM-TM | RT | Yes | N/A | 8/3/2007 |
| AIB3 | D3 | PENICILLIN G S3NM1LLLSSL 1 | PENICILLIN G S3NM1LLLSSL 1 | Soil 3 from Prairie, MN | YDM-TM | RT | Yes | N/A | 8/3/2007 |
| AIB3 | D4 | PENICILLIN G S3NM1LLLSSL 2 | PENICILLIN G S3NM1LLLSSL 2 | Soil 3 from Prairie, MN | YDM-TM | RT | Yes | N/A | 8/3/2007 |
| AIB3 | D5 | PENICILLIN G S3NM1LLLSSL 3 | PENICILLIN G S3NM1LLLSSL 3 | Soil 3 from Prairie, MN | YDM-TM | RT | Yes | N/A | 8/3/2007 |
| AIB3 | D6 | CARBENICILLIN S3NM1LLLSSL 1 | CARBENICILLIN S3NM1LLLSSL 1 | Soil 3 from Prairie, MN | YDM-TM | RT | Yes | N/A | 8/3/2007 |
| AIB3 | D7 | CARBENICILLIN S3NM1LLLSSL 2 | CARBENICILLIN S3NM1LLLSSL 2 | Soil 3 from Prairie, MN | YDM-TM | RT | Yes | N/A | 8/3/2007 |
| AIB3 | D8 | CARBENICILLIN S3NM1LLLSSL 3 | CARBENICILLIN S3NM1LLLSSL 3 | Soil 3 from Prairie, MN | YDM-TM | RT | Yes | N/A | 8/3/2007 |
| AIB3 | D9 | DICLO S3NM1LLLSSL 1 | DICLO S3NM1LLLSSL 1 | Soil 3 from Prairie, MN | YDM-TM | RT | Yes | N/A | 8/3/2007 |
| AIB3 | D10 | DICLO S3NM1LLLSSL 2 | DICLO S3NM1LLLSSL 2 | Soil 3 from Prairie, MN | YDM-TM | RT | Yes | N/A | 8/3/2007 |
| AIB3 | E1 | DICLO S3NM1LLLSSL 3 | DICLO S3NM1LLLSSL 3 | Soil 3 from Prairie, MN | YDM-TM | RT | Yes | N/A | 8/3/2007 |
| AIB3 | E2 | CHLORAM S3NM1LLLSSL 1 | CHLORAM S3NM1LLLSSL 1 | Soil 3 from Prairie, MN | YDM-TM | RT | Yes | N/A | 8/3/2007 |
| AIB3 | E3 | CHLORAM S3NM1LLLSSL 2 | CHLORAM S3NM1LLLSSL 2 | Soil 3 from Prairie, MN | YDM-TM | RT | Yes | N/A | 8/3/2007 |
| AIB3 | E4 | CHLORAM S3NM1LLLSSL 3 | CHLORAM S3NM1LLLSSL 3 | Soil 3 from Prairie, MN | YDM-TM | RT | Yes | N/A | 8/3/2007 |
| AIB3 | E5 | NALIDIXIC S3NM1LLLSSL 1 | NALIDIXIC S3NM1LLLSSL 1 | Soil 3 from Prairie, MN | YDM-TM | RT | Yes | N/A | 8/3/2007 |

Figure 8 (Cont.)

| | | | | | | | |
|---|---|---|---|---|---|---|---|
| AIB3 | E6 | NALIDIXIC S3NM1LLLSSL 2 | NALIDIXIC S3NM1LLLSSL 2 | Soil 3 from Prairie, MN | YDM-TM | RT | Yes | N/A | 8/3/2007 |
| AIB3 | E7 | NALIDIXIC S3NM1LLLSSL 3 | NALIDIXIC S3NM1LLLSSL 3 | Soil 3 from Prairie, MN | YDM-TM | RT | Yes | N/A | 8/3/2007 |
| AIB3 | E8 | THIAMPHENI S3NM1LLLSSL 1 | THIAMPHENI S3NM1LLLSSL 1 | Soil 3 from Prairie, MN | YDM-TM | RT | Yes | N/A | 8/3/2007 |
| AIB3 | E9 | THIAMPHENI S3NM1LLLSSL 2 | THIAMPHENI S3NM1LLLSSL 2 | Soil 3 from Prairie, MN | YDM-TM | RT | Yes | N/A | 8/3/2007 |
| AIB3 | E10 | THIAMPHENI S3NM1LLLSSL 3 | THIAMPHENI S3NM1LLLSSL 3 | Soil 3 from Prairie, MN | YDM-TM | RT | Yes | N/A | 8/3/2007 |
| AIB3 | F1 | TRIMETHO S3NM1LLLSSL 1 | TRIMETHO S3NM1LLLSSL 1 | Soil 3 from Prairie, MN | YDM-TM | RT | Yes | N/A | 8/3/2007 |
| AIB3 | F2 | TRIMETHO S3NM1LLLSSL 2 | TRIMETHO S3NM1LLLSSL 2 | Soil 3 from Prairie, MN | YDM-TM | RT | Yes | N/A | 8/3/2007 |
| AIB3 | F3 | TRIMETHO S3NM1LLLSSL 3 | TRIMETHO S3NM1LLLSSL 3 | Soil 3 from Prairie, MN | YDM-TM | RT | Yes | N/A | 8/3/2007 |
| AIB3 | F4 | MAFENIDE S3NM1LLLSSL 1 | MAFENIDE S3NM1LLLSSL 1 | Soil 3 from Prairie, MN | YDM-TM | RT | Yes | N/A | 8/3/2007 |
| AIB3 | F5 | MAFENIDE S3NM1LLLSSL 2 | MAFENIDE S3NM1LLLSSL 2 | Soil 3 from Prairie, MN | YDM-TM | RT | Yes | N/A | 8/3/2007 |
| AIB3 | F6 | MAFENIDE S3NM1LLLSSL 3 | MAFENIDE S3NM1LLLSSL 3 | Soil 3 from Prairie, MN | YDM-TM | RT | Yes | N/A | 8/3/2007 |
| AIB3 | F7 | TETRA S3NM1LLLSSL 1 | TETRA S3NM1LLLSSL 1 | Soil 3 from Prairie, MN | YDM-TM | RT | Yes | N/A | 8/3/2007 |
| AIB3 | F8 | TETRA S3NM1LLLSSL 2 | TETRA S3NM1LLLSSL 2 | Soil 3 from Prairie, MN | YDM-TM | RT | Yes | N/A | 8/3/2007 |
| AIB3 | F9 | TETRA S3NM1LLLSSL 3 | TETRA S3NM1LLLSSL 3 | Soil 3 from Prairie, MN | YDM-TM | RT | Yes | N/A | 8/3/2007 |
| AIB3 | F10 | OXYTET S3NM1LLLSSL 1 | OXYTET S3NM1LLLSSL 1 | Soil 3 from Prairie, MN | YDM-TM | RT | Yes | N/A | 8/3/2007 |
| AIB3 | G1 | OXYTET S3NM1LLLSSL 2 | OXYTET S3NM1LLLSSL 2 | Soil 3 from Prairie, MN | YDM-TM | RT | Yes | N/A | 8/3/2007 |
| AIB3 | G2 | OXYTET S3NM1LLLSSL 3 | OXYTET S3NM1LLLSSL 3 | Soil 3 from Prairie, MN | YDM-TM | RT | Yes | N/A | 8/3/2007 |
| AIB3 | G3 | VANCO S3NM1LLLSSL 1 | VANCO S3NM1LLLSSL 1 | Soil 3 from Prairie, MN | YDM-TM | RT | Yes | N/A | 8/3/2007 |
| AIB3 | G4 | VANCO S3NM1LLLSSL 2 | VANCO S3NM1LLLSSL 2 | Soil 3 from Prairie, MN | YDM-TM | RT | Yes | N/A | 8/3/2007 |
| AIB3 | G5 | VANCO S3NM1LLLSSL 3 | VANCO S3NM1LLLSSL 3 | Soil 3 from Prairie, MN | YDM-TM | RT | Yes | N/A | 8/3/2007 |
| AIB3 | G6 | CIPRO S1PM1LLLSSL1 | CIPRO S1PM1LLLSSL1 | Soil 1 fromBoston Public Garden, MA | YDM-TM | RT | Yes | N/A | 8/3/2007 |
| AIB3 | G7 | CIPRO S1PM1LLLSSL2 | CIPRO S1PM1LLLSSL2 | Soil 1 fromBoston Public Garden, MA | YDM-TM | RT | Yes | N/A | 8/3/2007 |
| AIB3 | G8 | CIPRO S1PM1LLLSSL3 | CIPRO S1PM1LLLSSL3 | Soil 1 fromBoston Public Garden, MA | YDM-TM | RT | Yes | N/A | 8/3/2007 |

Figure 8 (Cont.)

| | | | | | | | |
|---|---|---|---|---|---|---|---|
| AIB3 | G9 | LEVO S1PM1LLLSSL 1 | LEVO S1PM1LLLSSL 1 | Soil 1 fromBoston Public Garden, MA | YDM-TM | RT | Yes | N/A | 8/3/2007 |
| AIB3 | G10 | LEVO S1PM1LLLSSL 2 | LEVO S1PM1LLLSSL 2 | Soil 1 fromBoston Public Garden, MA | YDM-TM | RT | Yes | N/A | 8/3/2007 |
| AIB3 | H1 | LEVO S1PM1LLLSSL 3 | LEVO S1PM1LLLSSL 3 | Soil 1 fromBoston Public Garden, MA | YDM-TM | RT | Yes | N/A | 8/3/2007 |
| AIB3 | H2 | SISO S1PM1LLLSSL 1 | SISO S1PM1LLLSSL 1 | Soil 1 fromBoston Public Garden, MA | YDM-TM | RT | Yes | N/A | 8/3/2007 |
| AIB3 | H3 | SISO S1PM1LLLSSL 2 | SISO S1PM1LLLSSL 2 | Soil 1 fromBoston Public Garden, MA | YDM-TM | RT | Yes | N/A | 8/3/2007 |
| AIB3 | H4 | SISO S1PM1LLLSSL 3 | SISO S1PM1LLLSSL 3 | Soil 1 fromBoston Public Garden, MA | YDM-TM | RT | Yes | N/A | 8/3/2007 |
| AIB3 | H5 | GENTAMICIN S1PM1LLLSSL 1 | GENTAMICIN S1PM1LLLSSL 1 | Soil 1 fromBoston Public Garden, MA | YDM-TM | RT | Yes | N/A | 8/3/2007 |
| AIB3 | H6 | GENTAMICIN S1PM1LLLSSL 2 | GENTAMICIN S1PM1LLLSSL 2 | Soil 1 fromBoston Public Garden, MA | YDM-TM | RT | Yes | N/A | 8/3/2007 |
| AIB3 | H7 | GENTAMICIN S1PM1LLLSSL 3 | GENTAMICIN S1PM1LLLSSL 3 | Soil 1 fromBoston Public Garden, MA | YDM-TM | RT | Yes | N/A | 8/3/2007 |
| AIB3 | H8 | KANAMICIN S1PM1LLLSSL 1 | KANAMICIN S1PM1LLLSSL 1 | Soil 1 fromBoston Public Garden, MA | YDM-TM | RT | Yes | N/A | 8/3/2007 |
| AIB3 | H9 | KANAMICIN S1PM1LLLSSL 2 | KANAMICIN S1PM1LLLSSL 2 | Soil 1 fromBoston Public Garden, MA | YDM-TM | RT | Yes | N/A | 8/3/2007 |
| AIB3 | H10 | KANAMICIN S1PM1LLLSSL 3 | KANAMICIN S1PM1LLLSSL 3 | Soil 1 fromBoston Public Garden, MA | YDM-TM | RT | Yes | N/A | 8/3/2007 |
| AIB3 | I1 | AMIKACIN S1PM1LLLSSL 1 | AMIKACIN S1PM1LLLSSL 1 | Soil 1 fromBoston Public Garden, MA | YDM-TM | RT | Yes | N/A | 8/3/2007 |
| AIB3 | I2 | AMIKACIN S1PM1LLLSSL 2 | AMIKACIN S1PM1LLLSSL 2 | Soil 1 fromBoston Public Garden, MA | YDM-TM | RT | Yes | N/A | 8/3/2007 |
| AIB3 | I3 | AMIKACIN S1PM1LLLSSL 3 | AMIKACIN S1PM1LLLSSL 3 | Soil 1 fromBoston Public Garden, MA | YDM-TM | RT | Yes | N/A | 8/3/2007 |
| AIB3 | I4 | PENICILLIN G S1PM1LLLSSL 1 | PENICILLIN G S1PM1LLLSSL 1 | Soil 1 fromBoston Public Garden, MA | YDM-TM | RT | Yes | N/A | 8/3/2007 |
| AIB3 | I5 | PENICILLIN G S1PM1LLLSSL 2 | PENICILLIN G S1PM1LLLSSL 2 | Soil 1 fromBoston Public Garden, MA | YDM-TM | RT | Yes | N/A | 8/3/2007 |
| AIB3 | I6 | PENICILLIN G S1PM1LLLSSL 3 | PENICILLIN G S1PM1LLLSSL 3 | Soil 1 fromBoston Public Garden, MA | YDM-TM | RT | Yes | N/A | 8/3/2007 |
| AIB3 | I7 | CARBENICILLIN S1PM1LLLSSL 1 | CARBENICILLIN S1PM1LLLSSL 1 | Soil 1 fromBoston Public Garden, MA | YDM-TM | RT | Yes | N/A | 8/3/2007 |
| AIB3 | I8 | CARBENICILLIN S1PM1LLLSSL 2 | CARBENICILLIN S1PM1LLLSSL 2 | Soil 1 fromBoston Public Garden, MA | YDM-TM | RT | Yes | N/A | 8/3/2007 |
| AIB3 | I9 | CARBENICILLIN S1PM1LLLSSL 3 | CARBENICILLIN S1PM1LLLSSL 3 | Soil 1 fromBoston Public Garden, MA | YDM-TM | RT | Yes | N/A | 8/3/2007 |
| AIB3 | I10 | DICLO S1PM1LLLSSL 1 | DICLO S1PM1LLLSSL 1 | Soil 1 fromBoston Public Garden, MA | YDM-TM | RT | Yes | N/A | 8/3/2007 |
| AIB3 | J1 | DICLO S1PM1LLLSSL 2 | DICLO S1PM1LLLSSL 2 | Soil 1 fromBoston Public Garden, MA | YDM-TM | RT | Yes | N/A | 8/3/2007 |

Figure 8 (Cont.)

| AIB3 | J2 | DICLO S1PM1LLLSSL 3 | DICLO S1PM1LLLSSL 3 | Soil 1 fromBoston Public Garden, MA | YDM-TM | RT | Yes | N/A | 8/3/2007 |
|---|---|---|---|---|---|---|---|---|---|
| AIB3 | J3 | CHLORAM S1PM1LLLSSL 1 | CHLORAM S1PM1LLLSSL 1 | Soil 1 fromBoston Public Garden, MA | YDM-TM | RT | Yes | N/A | 8/3/2007 |
| AIB3 | J4 | CHLORAM S1PM1LLLSSL 2 | CHLORAM S1PM1LLLSSL 2 | Soil 1 fromBoston Public Garden, MA | YDM-TM | RT | Yes | N/A | 8/3/2007 |
| AIB3 | J5 | CHLORAM S1PM1LLLSSL 3 | CHLORAM S1PM1LLLSSL 3 | Soil 1 fromBoston Public Garden, MA | YDM-TM | RT | Yes | N/A | 8/3/2007 |
| AIB3 | J6 | NALIDIXIC S1PM1LLLSSL 1 | NALIDIXIC S1PM1LLLSSL 1 | Soil 1 fromBoston Public Garden, MA | YDM-TM | RT | Yes | N/A | 8/3/2007 |
| AIB3 | J7 | NALIDIXIC S1PM1LLLSSL 2 | NALIDIXIC S1PM1LLLSSL 2 | Soil 1 fromBoston Public Garden, MA | YDM-TM | RT | Yes | N/A | 8/3/2007 |
| AIB3 | J8 | NALIDIXIC S1PM1LLLSSL 3 | NALIDIXIC S1PM1LLLSSL 3 | Soil 1 fromBoston Public Garden, MA | YDM-TM | RT | Yes | N/A | 8/3/2007 |
| AIB3 | J9 | THIAMPHENI S1PM1LLLSSL 1 | THIAMPHENI S1PM1LLLSSL 1 | Soil 1 fromBoston Public Garden, MA | YDM-TM | RT | Yes | N/A | 8/3/2007 |
| AIB3 | J10 | THIAMPHENI S1PM1LLLSSL 2 | THIAMPHENI S1PM1LLLSSL 2 | Soil 1 fromBoston Public Garden, MA | YDM-TM | RT | Yes | N/A | 8/3/2007 |

Figure 8 (Cont.)

| Box | S* | Strain | Label | Source | Media | Temp | Oxygen | Extr | Date |
|---|---|---|---|---|---|---|---|---|---|
| A1B4 | A1 | THIAMPHENI S1PM1LLLSSL 3 | THIAMPHENI S1PM1LLLSSL 3 | Soil 1 fromBoston Public Garden, MA | YDM-TM | RT | Yes | N/A | 8/3/2007 |
| A1B4 | A2 | SULFISOXA S1PM1LLLSSL 1 | SULFISOXA S1PM1LLLSSL 1 | Soil 1 fromBoston Public Garden, MA | YDM-TM | RT | Yes | N/A | 8/3/2007 |
| A1B4 | A3 | SULFISOXA S1PM1LLLSSL 2 | SULFISOXA S1PM1LLLSSL 2 | Soil 1 fromBoston Public Garden, MA | YDM-TM | RT | Yes | N/A | 8/3/2007 |
| A1B4 | A4 | SULFISOXA S1PM1LLLSSL 3 | SULFISOXA S1PM1LLLSSL 3 | Soil 1 fromBoston Public Garden, MA | YDM-TM | RT | Yes | N/A | 8/3/2007 |
| A1B4 | A5 | TRIMETHO S1PM1LLLSSL 1 | TRIMETHO S1PM1LLLSSL 1 | Soil 1 fromBoston Public Garden, MA | YDM-TM | RT | Yes | N/A | 8/3/2007 |
| A1B4 | A6 | TRIMETHO S1PM1LLLSSL 2 | TRIMETHO S1PM1LLLSSL 2 | Soil 1 fromBoston Public Garden, MA | YDM-TM | RT | Yes | N/A | 8/3/2007 |
| A1B4 | A7 | TRIMETHO S1PM1LLLSSL 3 | TRIMETHO S1PM1LLLSSL 3 | Soil 1 fromBoston Public Garden, MA | YDM-TM | RT | Yes | N/A | 8/3/2007 |
| A1B4 | A8 | MAFENIDE S1PM1LLLSSL 1 | MAFENIDE S1PM1LLLSSL 1 | Soil 1 fromBoston Public Garden, MA | YDM-TM | RT | Yes | N/A | |
| A1B4 | A9 | MAFENIDE S1PM1LLLSSL 2 | MAFENIDE S1PM1LLLSSL 2 | Soil 1 fromBoston Public Garden, MA | YDM-TM | RT | Yes | N/A | 8/3/2007 |
| A1B4 | A10 | MAFENIDE S1PM1LLLSSL 3 | MAFENIDE S1PM1LLLSSL 3 | Soil 1 fromBoston Public Garden, MA | YDM-TM | RT | Yes | N/A | 8/3/2007 |
| A1B4 | B1 | SULFAMET S1PM1LLLSSL 1 | SULFAMET S1PM1LLLSSL 1 | Soil 1 fromBoston Public Garden, MA | YDM-TM | RT | Yes | N/A | 8/3/2007 |
| A1B4 | B2 | SULFAMET S1PM1LLLSSL 2 | SULFAMET S1PM1LLLSSL 2 | Soil 1 fromBoston Public Garden, MA | YDM-TM | RT | Yes | N/A | 8/3/2007 |
| A1B4 | B3 | SULFAMET S1PM1LLLSSL 3 | SULFAMET S1PM1LLLSSL 3 | Soil 1 fromBoston Public Garden, MA | YDM-TM | RT | Yes | N/A | 8/3/2007 |
| A1B4 | B4 | TETRA S1PM1LLLSSL 1 | TETRA S1PM1LLLSSL 1 | Soil 1 fromBoston Public Garden, MA | YDM-TM | RT | Yes | N/A | 8/3/2007 |
| A1B4 | B5 | TETRA S1PM1LLLSSL 2 | TETRA S1PM1LLLSSL 2 | Soil 1 fromBoston Public Garden, MA | YDM-TM | RT | Yes | N/A | 8/3/2007 |
| A1B4 | B6 | TETRA S1PM1LLLSSL 3 | TETRA S1PM1LLLSSL 3 | Soil 1 fromBoston Public Garden, MA | YDM-TM | RT | Yes | N/A | 8/3/2007 |
| A1B4 | B7 | OXYTET S1PM1LLLSSL 1 | OXYTET S1PM1LLLSSL 1 | Soil 1 fromBoston Public Garden, MA | YDM-TM | RT | Yes | N/A | 8/3/2007 |
| A1B4 | B8 | OXYTET S1PM1LLLSSL 2 | OXYTET S1PM1LLLSSL 2 | Soil 1 fromBoston Public Garden, MA | YDM-TM | RT | Yes | N/A | 8/3/2007 |
| A1B4 | B9 | OXYTET S1PM1LLLSSL 3 | OXYTET S1PM1LLLSSL 3 | Soil 1 fromBoston Public Garden, MA | YDM-TM | RT | Yes | N/A | 8/3/2007 |
| A1B4 | B10 | D-CYCLO S1PM1LLLSSL 1 | D-CYCLO S1PM1LLLSSL 1 | Soil 1 fromBoston Public Garden, MA | YDM-TM | RT | Yes | N/A | 8/3/2007 |
| A1B4 | C1 | D-CYCLO S1PM1LLLSSL 2 | D-CYCLO S1PM1LLLSSL 2 | Soil 1 fromBoston Public Garden, MA | YDM-TM | RT | Yes | N/A | 8/3/2007 |
| A1B4 | C2 | D-CYCLO S1PM1LLLSSL 3 | D-CYCLO S1PM1LLLSSL 3 | Soil 1 fromBoston Public Garden, MA | YDM-TM | RT | Yes | N/A | 8/3/2007 |

Figure 9

| | | | | | | | |
|---|---|---|---|---|---|---|---|
| AIB4 | C3 | VANCO S1PM1LLLSSL 1 | VANCO S1PM1LLLSSL 1 | Soil 1 fromBoston Public Garden, MA | YDM-TM | RT | Yes | N/A | 8/3/2007 |
| AIB4 | C4 | VANCO S1PM1LLLSSL 2 | VANCO S1PM1LLLSSL 2 | Soil 1 fromBoston Public Garden, MA | YDM-TM | RT | Yes | N/A | 8/3/2007 |
| AIB4 | C5 | VANCO S1PM1LLLSSL 3 | VANCO S1PM1LLLSSL 3 | Soil 1 fromBoston Public Garden, MA | YDM-TM | RT | Yes | N/A | 8/3/2007 |
| AIB4 | C6 | CIPRO S1TM1LLLSSL1 | CIPRO S1TM1LLLSSL1 | Soil 1 from 4 mix of waste soil, PA | YDM-TM | RT | Yes | N/A | 8/3/2007 |
| AIB4 | C7 | CIPRO S1TM1LLLSSL2 | CIPRO S1TM1LLLSSL2 | Soil 1 from 4 mix of waste soil, PA | YDM-TM | RT | Yes | N/A | 8/3/2007 |
| AIB4 | C8 | CIPRO S1TM1LLLSSL3 | CIPRO S1TM1LLLSSL3 | Soil 1 from 4 mix of waste soil, PA | YDM-TM | RT | Yes | N/A | 8/3/2007 |
| AIB4 | C9 | LEVO S1TM1LLLSSL 1 | LEVO S1TM1LLLSSL 1 | Soil 1 from 4 mix of waste soil, PA | YDM-TM | RT | Yes | N/A | 8/3/2007 |
| AIB4 | C10 | LEVO S1TM1LLLSSL 2 | LEVO S1TM1LLLSSL 2 | Soil 1 from 4 mix of waste soil, PA | YDM-TM | RT | Yes | N/A | 8/3/2007 |
| AIB4 | D1 | LEVO S1TM1LLLSSL 3 | LEVO S1TM1LLLSSL 3 | Soil 1 from 4 mix of waste soil, PA | YDM-TM | RT | Yes | N/A | 8/3/2007 |
| AIB4 | D2 | SISO S1TM1LLLSSL 1 | SISO S1TM1LLLSSL 1 | Soil 1 from 4 mix of waste soil, PA | YDM-TM | RT | Yes | N/A | 8/3/2007 |
| AIB4 | D3 | SISO S1TM1LLLSSL 2 | SISO S1TM1LLLSSL 2 | Soil 1 from 4 mix of waste soil, PA | YDM-TM | RT | Yes | N/A | 8/3/2007 |
| AIB4 | D4 | SISO S1TM1LLLSSL 3 | SISO S1TM1LLLSSL 3 | Soil 1 from 4 mix of waste soil, PA | YDM-TM | RT | Yes | N/A | 8/3/2007 |
| AIB4 | D5 | GENTAMICIN S1TM1LLLSSL 1 | GENTAMICIN S1TM1LLLSSL 1 | Soil 1 from 4 mix of waste soil, PA | YDM-TM | RT | Yes | N/A | 8/3/2007 |
| AIB4 | D6 | GENTAMICIN S1TM1LLLSSL 2 | GENTAMICIN S1TM1LLLSSL 2 | Soil 1 from 4 mix of waste soil, PA | YDM-TM | RT | Yes | N/A | 8/3/2007 |
| AIB4 | D7 | GENTAMICIN S1TM1LLLSSL 3 | GENTAMICIN S1TM1LLLSSL 3 | Soil 1 from 4 mix of waste soil, PA | YDM-TM | RT | Yes | N/A | 8/3/2007 |
| AIB4 | D8 | KANAMICIN S1TM1LLLSSL 1 | KANAMICIN S1TM1LLLSSL 1 | Soil 1 from 4 mix of waste soil, PA | YDM-TM | RT | Yes | N/A | 8/3/2007 |
| AIB4 | D9 | KANAMICIN S1TM1LLLSSL 2 | KANAMICIN S1TM1LLLSSL 2 | Soil 1 from 4 mix of waste soil, PA | YDM-TM | RT | Yes | N/A | 8/3/2007 |
| AIB4 | D10 | KANAMICIN S1TM1LLLSSL 3 | KANAMICIN S1TM1LLLSSL 3 | Soil 1 from 4 mix of waste soil, PA | YDM-TM | RT | Yes | N/A | 8/3/2007 |
| AIB4 | E1 | AMIKACIN S1TM1LLLSSL 1 | AMIKACIN S1TM1LLLSSL 1 | Soil 1 from 4 mix of waste soil, PA | YDM-TM | RT | Yes | N/A | 8/3/2007 |
| AIB4 | E2 | AMIKACIN S1TM1LLLSSL 2 | AMIKACIN S1TM1LLLSSL 2 | Soil 1 from 4 mix of waste soil, PA | YDM-TM | RT | Yes | N/A | 8/3/2007 |
| AIB4 | E3 | AMIKACIN S1TM1LLLSSL 3 | AMIKACIN S1TM1LLLSSL 3 | Soil 1 from 4 mix of waste soil, PA | YDM-TM | RT | Yes | N/A | 8/3/2007 |
| AIB4 | E4 | PENICILLIN G S1TM1LLLSSL 1 | PENICILLIN G S1TM1LLLSSL 1 | Soil 1 from 4 mix of waste soil, PA | YDM-TM | RT | Yes | N/A | 8/3/2007 |
| AIB4 | E5 | PENICILLIN G S1TM1LLLSSL 2 | PENICILLIN G S1TM1LLLSSL 2 | Soil 1 from 4 mix of waste soil, PA | YDM-TM | RT | Yes | N/A | 8/3/2007 |

Figure 9 (Cont.)

| | | | | | | | |
|---|---|---|---|---|---|---|---|
| AIB4 | E6 | PENICILLIN G S1TM1LLLSSL 3 | PENICILLIN G S1TM1LLLSSL 3 | Soil 1 from 4 mix of waste soil, PA | YDM-TM | RT | Yes | N/A | 8/3/2007 |
| AIB4 | E7 | CARBENICILLIN S1TM1LLLSSL 1 | CARBENICILLIN S1TM1LLLSSL 1 | Soil 1 from 4 mix of waste soil, PA | YDM-TM | RT | Yes | N/A | 8/3/2007 |
| AIB4 | E8 | CARBENICILLIN S1TM1LLLSSL 2 | CARBENICILLIN S1TM1LLLSSL 2 | Soil 1 from 4 mix of waste soil, PA | YDM-TM | RT | Yes | N/A | 8/3/2007 |
| AIB4 | E9 | CARBENICILLIN S1TM1LLLSSL 3 | CARBENICILLIN S1TM1LLLSSL 3 | Soil 1 from 4 mix of waste soil, PA | YDM-TM | RT | Yes | N/A | 8/3/2007 |
| AIB4 | E10 | DICLO S1TM1LLLSSL 1 | DICLO S1TM1LLLSSL 1 | Soil 1 from 4 mix of waste soil, PA | YDM-TM | RT | Yes | N/A | 8/3/2007 |
| AIB4 | F1 | DICLO S1TM1LLLSSL 2 | DICLO S1TM1LLLSSL 2 | Soil 1 from 4 mix of waste soil, PA | YDM-TM | RT | Yes | N/A | 8/3/2007 |
| AIB4 | F2 | DICLO S1TM1LLLSSL 3 | DICLO S1TM1LLLSSL 3 | Soil 1 from 4 mix of waste soil, PA | YDM-TM | RT | Yes | N/A | 8/3/2007 |
| AIB4 | F3 | CHLORAM S1TM1LLLSSL 1 | CHLORAM S1TM1LLLSSL 1 | Soil 1 from 4 mix of waste soil, PA | YDM-TM | RT | Yes | N/A | 8/3/2007 |
| AIB4 | F4 | CHLORAM S1TM1LLLSSL 2 | CHLORAM S1TM1LLLSSL 2 | Soil 1 from 4 mix of waste soil, PA | YDM-TM | RT | Yes | N/A | |
| AIB4 | F5 | CHLORAM S1TM1LLLSSL 3 | CHLORAM S1TM1LLLSSL 3 | Soil 1 from 4 mix of waste soil, PA | YDM-TM | RT | Yes | N/A | 8/3/2007 |
| AIB4 | F6 | NALIDIXIC S1TM1LLLSSL 1 | NALIDIXIC S1TM1LLLSSL 1 | Soil 1 from 4 mix of waste soil, PA | YDM-TM | RT | Yes | N/A | 8/3/2007 |
| AIB4 | F7 | NALIDIXIC S1TM1LLLSSL 2 | NALIDIXIC S1TM1LLLSSL 2 | Soil 1 from 4 mix of waste soil, PA | YDM-TM | RT | Yes | N/A | 8/3/2007 |
| AIB4 | F8 | NALIDIXIC S1TM1LLLSSL 3 | NALIDIXIC S1TM1LLLSSL 3 | Soil 1 from 4 mix of waste soil, PA | YDM-TM | RT | Yes | N/A | 8/3/2007 |
| AIB4 | F9 | THIAMPHENI S1TM1LLLSSL 1 | THIAMPHENI S1TM1LLLSSL 1 | Soil 1 from 4 mix of waste soil, PA | YDM-TM | RT | Yes | N/A | 8/3/2007 |
| AIB4 | F10 | THIAMPHENI S1TM1LLLSSL 2 | THIAMPHENI S1TM1LLLSSL 2 | Soil 1 from 4 mix of waste soil, PA | YDM-TM | RT | Yes | N/A | 8/3/2007 |
| AIB4 | G1 | THIAMPHENI S1TM1LLLSSL 3 | THIAMPHENI S1TM1LLLSSL 3 | Soil 1 from 4 mix of waste soil, PA | YDM-TM | RT | Yes | N/A | 8/3/2007 |
| AIB4 | G2 | TRIMETHO S1TM1LLLSSL 1 | TRIMETHO S1TM1LLLSSL 1 | Soil 1 from 4 mix of waste soil, PA | YDM-TM | RT | Yes | N/A | 8/3/2007 |
| AIB4 | G3 | TRIMETHO S1TM1LLLSSL 2 | TRIMETHO S1TM1LLLSSL 2 | Soil 1 from 4 mix of waste soil, PA | YDM-TM | RT | Yes | N/A | 8/3/2007 |
| AIB4 | G4 | TRIMETHO S1TM1LLLSSL 3 | TRIMETHO S1TM1LLLSSL 3 | Soil 1 from 4 mix of waste soil, PA | YDM-TM | RT | Yes | N/A | 8/3/2007 |
| AIB4 | G5 | MAFENIDE S1TM1LLLSSL 1 | MAFENIDE S1TM1LLLSSL 1 | Soil 1 from 4 mix of waste soil, PA | YDM-TM | RT | Yes | N/A | 8/3/2007 |
| AIB4 | G6 | MAFENIDE S1TM1LLLSSL 2 | MAFENIDE S1TM1LLLSSL 2 | Soil 1 from 4 mix of waste soil, PA | YDM-TM | RT | Yes | N/A | 8/3/2007 |
| AIB4 | G7 | MAFENIDE S1TM1LLLSSL 3 | MAFENIDE S1TM1LLLSSL 3 | Soil 1 from 4 mix of waste soil, PA | YDM-TM | RT | Yes | N/A | 8/3/2007 |
| AIB4 | G8 | SULFAMET S1TM1LLLSSL 1 | SULFAMET S1TM1LLLSSL 1 | Soil 1 from 4 mix of waste soil, PA | YDM-TM | RT | Yes | N/A | 8/3/2007 |

Figure 9 (Cont.)

| AIB4 | G9 | SULFAMET S1TM1LLLSSL 2 | SULFAMET S1TM1LLLSSL 2 | Soil 1 from 4 mix of waste soil, PA | YDM-TM | RT | Yes | N/A | 8/3/2007 |
|---|---|---|---|---|---|---|---|---|---|
| AIB4 | G10 | SULFAMET S1TM1LLLSSL 3 | SULFAMET S1TM1LLLSSL 3 | Soil 1 from 4 mix of waste soil, PA | YDM-TM | RT | Yes | N/A | 8/3/2007 |
| AIB4 | H1 | TETRA S1TM1LLLSSL 1 | TETRA S1TM1LLLSSL 1 | Soil 1 from 4 mix of waste soil, PA | YDM-TM | RT | Yes | N/A | 8/3/2007 |
| AIB4 | H2 | TETRA S1TM1LLLSSL 2 | TETRA S1TM1LLLSSL 2 | Soil 1 from 4 mix of waste soil, PA | YDM-TM | RT | Yes | N/A | 8/3/2007 |
| AIB4 | H3 | TETRA S1TM1LLLSSL 3 | TETRA S1TM1LLLSSL 3 | Soil 1 from 4 mix of waste soil, PA | YDM-TM | RT | Yes | N/A | 8/3/2007 |
| AIB4 | H4 | OXYTET S1TM1LLLSSL 1 | OXYTET S1TM1LLLSSL 1 | Soil 1 from 4 mix of waste soil, PA | YDM-TM | RT | Yes | N/A | 8/3/2007 |
| AIB4 | H5 | OXYTET S1TM1LLLSSL 2 | OXYTET S1TM1LLLSSL 2 | Soil 1 from 4 mix of waste soil, PA | YDM-TM | RT | Yes | N/A | 8/3/2007 |
| AIB4 | H6 | OXYTET S1TM1LLLSSL 3 | OXYTET S1TM1LLLSSL 3 | Soil 1 from 4 mix of waste soil, PA | YDM-TM | RT | Yes | N/A | 8/3/2007 |
| AIB4 | H7 | MINOCY S1TM1LLLSSL 1 | MINOCY S1TM1LLLSSL 1 | Soil 1 from 4 mix of waste soil, PA | YDM-TM | RT | Yes | N/A | 8/3/2007 |
| AIB4 | H8 | MINOCY S1TM1LLLSSL 2 | MINOCY S1TM1LLLSSL 2 | Soil 1 from 4 mix of waste soil, PA | YDM-TM | RT | Yes | N/A | 8/3/2007 |
| AIB4 | H9 | MINOCY S1TM1LLLSSL 3 | MINOCY S1TM1LLLSSL 3 | Soil 1 from 4 mix of waste soil, PA | YDM-TM | RT | Yes | N/A | 8/3/2007 |
| AIB4 | H10 | D-CYCLO S1TM1LLLSSL 1 | D-CYCLO S1TM1LLLSSL 1 | Soil 1 from 4 mix of waste soil, PA | YDM-TM | RT | Yes | N/A | 8/3/2007 |
| AIB4 | I1 | D-CYCLO S1TM1LLLSSL 2 | D-CYCLO S1TM1LLLSSL 2 | Soil 1 from 4 mix of waste soil, PA | YDM-TM | RT | Yes | N/A | 8/3/2007 |
| AIB4 | I2 | D-CYCLO S1TM1LLLSSL 3 | D-CYCLO S1TM1LLLSSL 3 | Soil 1 from 4 mix of waste soil, PA | YDM-TM | RT | Yes | N/A | 8/3/2007 |
| AIB4 | I3 | VANCO S1TM1LLLSSL 1 | VANCO S1TM1LLLSSL 1 | Soil 1 from 4 mix of waste soil, PA | YDM-TM | RT | Yes | N/A | 8/3/2007 |
| AIB4 | I4 | VANCO S1TM1LLLSSL 2 | VANCO S1TM1LLLSSL 2 | Soil 1 from 4 mix of waste soil, PA | YDM-TM | RT | Yes | N/A | 8/3/2007 |
| AIB4 | I5 | VANCO S1TM1LLLSSL 3 | VANCO S1TM1LLLSSL 3 | Soil 1 from 4 mix of waste soil, PA | YDM-TM | RT | Yes | N/A | 8/3/2007 |
| AIB4 | I6 | CIPRO S3FM1LLLSSL1 | CIPRO S3FM1LLLSSL1 | Soil 3 from Fenway | YDM-TM | RT | Yes | N/A | 8/3/2007 |
| AIB4 | I7 | CIPRO S3FM1LLLSSL2 | CIPRO S3FM1LLLSSL2 | Soil 3 from Fenway | YDM-TM | RT | Yes | N/A | 8/3/2007 |
| AIB4 | I8 | CIPRO S3FM1LLLSSL3 | CIPRO S3FM1LLLSSL3 | Soil 3 from Fenway | YDM-TM | RT | Yes | N/A | 8/3/2007 |
| AIB4 | I9 | LEVO S3FM1LLLSSL 1 | LEVO S3FM1LLLSSL 1 | Soil 3 from Fenway | YDM-TM | RT | Yes | N/A | 8/3/2007 |
| AIB4 | I10 | LEVO S3FM1LLLSSL 2 | LEVO S3FM1LLLSSL 2 | Soil 3 from Fenway | YDM-TM | RT | Yes | N/A | 8/3/2007 |
| AIB4 | J1 | LEVO S3FM1LLLSSL 3 | LEVO S3FM1LLLSSL 3 | Soil 3 from Fenway | YDM-TM | RT | Yes | N/A | 8/3/2007 |

Figure 9 (Cont.)

| AIB4 | J2 | SISO S3FM1LLLSSL 1 | Soil 3 from Fenway | YDM-TM | RT | Yes | N/A | 8/3/2007 |
|---|---|---|---|---|---|---|---|---|
| AIB4 | J3 | SISO S3FM1LLLSSL 2 | Soil 3 from Fenway | YDM-TM | RT | Yes | N/A | 8/3/2007 |
| AIB4 | J4 | SISO S3FM1LLLSSL 3 | Soil 3 from Fenway | YDM-TM | RT | Yes | N/A | 8/3/2007 |
| AIB4 | J5 | GENTAMICIN S3FM1LLLSSL 1 | Soil 3 from Fenway | YDM-TM | RT | Yes | N/A | 8/3/2007 |
| AIB4 | J6 | GENTAMICIN S3FM1LLLSSL 2 | Soil 3 from Fenway | YDM-TM | RT | Yes | N/A | 8/3/2007 |
| AIB4 | J7 | GENTAMICIN S3FM1LLLSSL 3 | Soil 3 from Fenway | YDM-TM | RT | Yes | N/A | 8/3/2007 |
| AIB4 | J8 | KANAMICIN S3FM1LLLSSL 1 | Soil 3 from Fenway | YDM-TM | RT | Yes | N/A | 8/3/2007 |
| AIB4 | J9 | KANAMICIN S3FM1LLLSSL 2 | Soil 3 from Fenway | YDM-TM | RT | Yes | N/A | 8/3/2007 |
| AIB4 | J10 | KANAMICIN S3FM1LLLSSL 3 | Soil 3 from Fenway | YDM-TM | RT | Yes | N/A | 8/3/2007 |

Figure 9 (Cont.)

| Box | S* | Strain | Label | Source | Media | Temp | Oxygen | Extr | Date |
|---|---|---|---|---|---|---|---|---|---|
| AIB5 | A1 | AMIKACIN S3FM1LLLSSL 1 | AMIKACIN S3FM1LLLSSL 1 | Soil 3 from Fenway | YDM-TM | RT | Yes | N/A | 8/3/2007 |
| AIB5 | A2 | AMIKACIN S3FM1LLLSSL 2 | AMIKACIN S3FM1LLLSSL 2 | Soil 3 from Fenway | YDM-TM | RT | Yes | N/A | 8/3/2007 |
| AIB5 | A3 | AMIKACIN S3FM1LLLSSL 3 | AMIKACIN S3FM1LLLSSL 3 | Soil 3 from Fenway | YDM-TM | RT | Yes | N/A | 8/3/2007 |
| AIB5 | A4 | PENICILLIN G S3FM1LLLSSL 1 | PENICILLIN G S3FM1LLLSSL 1 | Soil 3 from Fenway | YDM-TM | RT | Yes | N/A | 8/3/2007 |
| AIB5 | A5 | PENICILLIN G S3FM1LLLSSL 2 | PENICILLIN G S3FM1LLLSSL 2 | Soil 3 from Fenway | YDM-TM | RT | Yes | N/A | 8/3/2007 |
| AIB5 | A6 | PENICILLIN G S3FM1LLLSSL 3 | PENICILLIN G S3FM1LLLSSL 3 | Soil 3 from Fenway | YDM-TM | RT | Yes | N/A | 8/3/2007 |
| AIB5 | A7 | CARBENICILLIN S3FM1LLLSSL 1 | CARBENICILLIN S3FM1LLLSSL 1 | Soil 3 from Fenway | YDM-TM | RT | Yes | N/A | 8/3/2007 |
| AIB5 | A8 | CARBENICILLIN S3FM1LLLSSL 2 | CARBENICILLIN S3FM1LLLSSL 2 | Soil 3 from Fenway | YDM-TM | RT | Yes | N/A | 8/3/2007 |
| AIB5 | A9 | CARBENICILLIN S3FM1LLLSSL 3 | CARBENICILLIN S3FM1LLLSSL 3 | Soil 3 from Fenway | YDM-TM | RT | Yes | N/A | 8/3/2007 |
| AIB5 | A10 | DICLO S3FM1LLLSSL 1 | DICLO S3FM1LLLSSL 1 | Soil 3 from Fenway | YDM-TM | RT | Yes | N/A | 8/3/2007 |
| AIB5 | B1 | DICLO S3FM1LLLSSL 2 | DICLO S3FM1LLLSSL 2 | Soil 3 from Fenway | YDM-TM | RT | Yes | N/A | 8/3/2007 |
| AIB5 | B2 | DICLO S3FM1LLLSSL 3 | DICLO S3FM1LLLSSL 3 | Soil 3 from Fenway | YDM-TM | RT | Yes | N/A | 8/3/2007 |
| AIB5 | B3 | CHLORAM S3FM1LLLSSL 1 | CHLORAM S3FM1LLLSSL 1 | Soil 3 from Fenway | YDM-TM | RT | Yes | N/A | 8/3/2007 |
| AIB5 | B4 | CHLORAM S3FM1LLLSSL 2 | CHLORAM S3FM1LLLSSL 2 | Soil 3 from Fenway | YDM-TM | RT | Yes | N/A | 8/3/2007 |
| AIB5 | B5 | CHLORAM S3FM1LLLSSL 3 | CHLORAM S3FM1LLLSSL 3 | Soil 3 from Fenway | YDM-TM | RT | Yes | N/A | 8/3/2007 |
| AIB5 | B6 | NALIDIXIC S3FM1LLLSSL 1 | NALIDIXIC S3FM1LLLSSL 1 | Soil 3 from Fenway | YDM-TM | RT | Yes | N/A | 8/3/2007 |
| AIB5 | B7 | NALIDIXIC S3FM1LLLSSL 2 | NALIDIXIC S3FM1LLLSSL 2 | Soil 3 from Fenway | YDM-TM | RT | Yes | N/A | 8/3/2007 |
| AIB5 | B8 | NALIDIXIC S3FM1LLLSSL 3 | NALIDIXIC S3FM1LLLSSL 3 | Soil 3 from Fenway | YDM-TM | RT | Yes | N/A | 8/3/2007 |
| AIB5 | B9 | THIAMPHENI S3FM1LLLSSL 1 | THIAMPHENI S3FM1LLLSSL 1 | Soil 3 from Fenway | YDM-TM | RT | Yes | N/A | 8/3/2007 |
| AIB5 | B10 | THIAMPHENI S3FM1LLLSSL 2 | THIAMPHENI S3FM1LLLSSL 2 | Soil 3 from Fenway | YDM-TM | RT | Yes | N/A | 8/3/2007 |
| AIB5 | C1 | THIAMPHENI S3FM1LLLSSL 3 | THIAMPHENI S3FM1LLLSSL 3 | Soil 3 from Fenway | YDM-TM | RT | Yes | N/A | 8/3/2007 |
| AIB5 | C2 | SULFISOXA S3FM1LLLSSL 1 | SULFISOXA S3FM1LLLSSL 1 | Soil 3 from Fenway | YDM-TM | RT | Yes | N/A | 8/3/2007 |

Figure 10

| | | | | | | | |
|---|---|---|---|---|---|---|---|
| AIB5 | C3 | SULFISOXA S3FM1LLLSSL 2 | SULFISOXA S3FM1LLLSSL 2 | Soil 3 from Fenway | YDM-TM | RT | Yes | N/A | 8/3/2007 |
| AIB5 | C4 | SULFISOXA S3FM1LLLSSL 3 | SULFISOXA S3FM1LLLSSL 3 | Soil 3 from Fenway | YDM-TM | RT | Yes | N/A | 8/3/2007 |
| AIB5 | C5 | TRIMETHO S3FM1LLLSSL 1 | TRIMETHO S3FM1LLLSSL 1 | Soil 3 from Fenway | YDM-TM | RT | Yes | N/A | 8/3/2007 |
| AIB5 | C6 | TRIMETHO S3FM1LLLSSL 2 | TRIMETHO S3FM1LLLSSL 2 | Soil 3 from Fenway | YDM-TM | RT | Yes | N/A | 8/3/2007 |
| AIB5 | C7 | TRIMETHO S3FM1LLLSSL 3 | TRIMETHO S3FM1LLLSSL 3 | Soil 3 from Fenway | YDM-TM | RT | Yes | N/A | 8/3/2007 |
| AIB5 | C8 | MAFENIDE S3FM1LLLSSL 1 | MAFENIDE S3FM1LLLSSL 1 | Soil 3 from Fenway | YDM-TM | RT | Yes | N/A | 8/3/2007 |
| AIB5 | C9 | MAFENIDE S3FM1LLLSSL 2 | MAFENIDE S3FM1LLLSSL 2 | Soil 3 from Fenway | YDM-TM | RT | Yes | N/A | 8/3/2007 |
| AIB5 | C10 | MAFENIDE S3FM1LLLSSL 3 | MAFENIDE S3FM1LLLSSL 3 | Soil 3 from Fenway | YDM-TM | RT | Yes | N/A | 8/3/2007 |
| AIB5 | D1 | SULFAMET S3FM1LLLSSL 1 | SULFAMET S3FM1LLLSSL 1 | Soil 3 from Fenway | YDM-TM | RT | Yes | N/A | |
| AIB5 | D2 | SULFAMET S3FM1LLLSSL 2 | SULFAMET S3FM1LLLSSL 2 | Soil 3 from Fenway | YDM-TM | RT | Yes | N/A | 8/3/2007 |
| AIB5 | D3 | SULFAMET S3FM1LLLSSL 3 | SULFAMET S3FM1LLLSSL 3 | Soil 3 from Fenway | YDM-TM | RT | Yes | N/A | 8/3/2007 |
| AIB5 | D4 | TETRA S3FM1LLLSSL 1 | TETRA S3FM1LLLSSL 1 | Soil 3 from Fenway | YDM-TM | RT | Yes | N/A | 8/3/2007 |
| AIB5 | D5 | TETRA S3FM1LLLSSL 2 | TETRA S3FM1LLLSSL 2 | Soil 3 from Fenway | YDM-TM | RT | Yes | N/A | 8/3/2007 |
| AIB5 | D6 | TETRA S3FM1LLLSSL 3 | TETRA S3FM1LLLSSL 3 | Soil 3 from Fenway | YDM-TM | RT | Yes | N/A | 8/3/2007 |
| AIB5 | D7 | OXYTET S3FM1LLLSSL 1 | OXYTET S3FM1LLLSSL 1 | Soil 3 from Fenway | YDM-TM | RT | Yes | N/A | 8/3/2007 |
| AIB5 | D8 | OXYTET S3FM1LLLSSL 2 | OXYTET S3FM1LLLSSL 2 | Soil 3 from Fenway | YDM-TM | RT | Yes | N/A | 8/3/2007 |
| AIB5 | D9 | OXYTET S3FM1LLLSSL 3 | OXYTET S3FM1LLLSSL 3 | Soil 3 from Fenway | YDM-TM | RT | Yes | N/A | 8/3/2007 |
| AIB5 | D10 | MINOCY S3FM1LLLSSL 1 | MINOCY S3FM1LLLSSL 1 | Soil 3 from Fenway | YDM-TM | RT | Yes | N/A | 8/3/2007 |
| AIB5 | E1 | MINOCY S3FM1LLLSSL 2 | MINOCY S3FM1LLLSSL 2 | Soil 3 from Fenway | YDM-TM | RT | Yes | N/A | 8/3/2007 |
| AIB5 | E2 | MINOCY S3FM1LLLSSL 3 | MINOCY S3FM1LLLSSL 3 | Soil 3 from Fenway | YDM-TM | RT | Yes | N/A | 8/3/2007 |
| AIB5 | E3 | D-CYCLO S3FM1LLLSSL 1 | D-CYCLO S3FM1LLLSSL 1 | Soil 3 from Fenway | YDM-TM | RT | Yes | N/A | 8/3/2007 |
| AIB5 | E4 | D-CYCLO S3FM1LLLSSL 2 | D-CYCLO S3FM1LLLSSL 2 | Soil 3 from Fenway | YDM-TM | RT | Yes | N/A | 8/3/2007 |
| AIB5 | E5 | D-CYCLO S3FM1LLLSSL 3 | D-CYCLO S3FM1LLLSSL 3 | Soil 3 from Fenway | YDM-TM | RT | Yes | N/A | 8/3/2007 |

Figure 10 (Cont.)

| | | | | | | | |
|---|---|---|---|---|---|---|---|
| AIB5 | E6 | VANCO S3FM1LLLSSL 1 | VANCO S3FM1LLLSSL 1 | Soil 3 from Fenway | YDM-TM | RT | Yes | N/A | 8/3/2007 |
| AIB5 | E7 | VANCO S3FM1LLLSSL 2 | VANCO S3FM1LLLSSL 2 | Soil 3 from Fenway | YDM-TM | RT | Yes | N/A | 8/3/2007 |
| AIB5 | E8 | VANCO S3FM1LLLSSL 3 | VANCO S3FM1LLLSSL 3 | Soil 3 from Fenway | YDM-TM | RT | Yes | N/A | 8/3/2007 |
| AIB5 | E9 | CIPRO S1RM1LLLSSL1 | CIPRO S1RM1LLLSSL1 | Soil 1 from Brier's Swamp | YDM-TM | RT | Yes | N/A | 8/3/2007 |
| AIB5 | E10 | CIPRO S1RM1LLLSSL2 | CIPRO S1RM1LLLSSL2 | Soil 1 from Brier's Swamp | YDM-TM | RT | Yes | N/A | 8/3/2007 |
| AIB5 | F1 | CIPRO S1RM1LLLSSL3 | CIPRO S1RM1LLLSSL3 | Soil 1 from Brier's Swamp | YDM-TM | RT | Yes | N/A | 8/3/2007 |
| AIB5 | F2 | LEVO S1RM1LLLSSL 1 | LEVO S1RM1LLLSSL 1 | Soil 1 from Brier's Swamp | YDM-TM | RT | Yes | N/A | 8/3/2007 |
| AIB5 | F3 | LEVO S1RM1LLLSSL 2 | LEVO S1RM1LLLSSL 2 | Soil 1 from Brier's Swamp | YDM-TM | RT | Yes | N/A | 8/3/2007 |
| AIB5 | F4 | LEVO S1RM1LLLSSL 3 | LEVO S1RM1LLLSSL 3 | Soil 1 from Brier's Swamp | YDM-TM | RT | Yes | N/A | 8/3/2007 |
| AIB5 | F5 | SISO S1RM1LLLSSL 1 | SISO S1RM1LLLSSL 1 | Soil 1 from Brier's Swamp | YDM-TM | RT | Yes | N/A | 8/3/2007 |
| AIB5 | F6 | SISO S1RM1LLLSSL 2 | SISO S1RM1LLLSSL 2 | Soil 1 from Brier's Swamp | YDM-TM | RT | Yes | N/A | 8/3/2007 |
| AIB5 | F7 | SISO S1RM1LLLSSL 3 | SISO S1RM1LLLSSL 3 | Soil 1 from Brier's Swamp | YDM-TM | RT | Yes | N/A | 8/3/2007 |
| AIB5 | F8 | GENTAMICIN S1RM1LLLSSL 1 | GENTAMICIN S1RM1LLLSSL 1 | Soil 1 from Brier's Swamp | YDM-TM | RT | Yes | N/A | 8/3/2007 |
| AIB5 | F9 | GENTAMICIN S1RM1LLLSSL 2 | GENTAMICIN S1RM1LLLSSL 2 | Soil 1 from Brier's Swamp | YDM-TM | RT | Yes | N/A | 8/3/2007 |
| AIB5 | F10 | GENTAMICIN S1RM1LLLSSL 3 | GENTAMICIN S1RM1LLLSSL 3 | Soil 1 from Brier's Swamp | YDM-TM | RT | Yes | N/A | 8/3/2007 |
| AIB5 | G1 | KANAMICIN S1RM1LLLSSL 1 | KANAMICIN S1RM1LLLSSL 1 | Soil 1 from Brier's Swamp | YDM-TM | RT | Yes | N/A | 8/3/2007 |
| AIB5 | G2 | KANAMICIN S1RM1LLLSSL 2 | KANAMICIN S1RM1LLLSSL 2 | Soil 1 from Brier's Swamp | YDM-TM | RT | Yes | N/A | 8/3/2007 |
| AIB5 | G3 | KANAMICIN S1RM1LLLSSL 3 | KANAMICIN S1RM1LLLSSL 3 | Soil 1 from Brier's Swamp | YDM-TM | RT | Yes | N/A | 8/3/2007 |
| AIB5 | G4 | AMIKACIN S1RM1LLLSSL 1 | AMIKACIN S1RM1LLLSSL 1 | Soil 1 from Brier's Swamp | YDM-TM | RT | Yes | N/A | 8/3/2007 |
| AIB5 | G5 | AMIKACIN S1RM1LLLSSL 2 | AMIKACIN S1RM1LLLSSL 2 | Soil 1 from Brier's Swamp | YDM-TM | RT | Yes | N/A | 8/3/2007 |
| AIB5 | G6 | AMIKACIN S1RM1LLLSSL 3 | AMIKACIN S1RM1LLLSSL 3 | Soil 1 from Brier's Swamp | YDM-TM | RT | Yes | N/A | 8/3/2007 |
| AIB5 | G7 | PENICILLIN G S1RM1LLLSSL 1 | PENICILLIN G S1RM1LLLSSL 1 | Soil 1 from Brier's Swamp | YDM-TM | RT | Yes | N/A | 8/3/2007 |
| AIB5 | G8 | PENICILLIN G S1RM1LLLSSL 2 | PENICILLIN G S1RM1LLLSSL 2 | Soil 1 from Brier's Swamp | YDM-TM | RT | Yes | N/A | 8/3/2007 |

Figure 10 (Cont.)

| | | | | | | | |
|---|---|---|---|---|---|---|---|
| AIB5 | G9 | PENICILLIN G S1RM1LLLSSL 3 | PENICILLIN G S1RM1LLLSSL 3 | Soil 1 from Brier's Swamp | YDM-TM | RT | Yes | N/A | 8/3/2007 |
| AIB5 | G10 | CARBENICILLIN S1RM1LLLSSL 1 | CARBENICILLIN S1RM1LLLSSL 1 | Soil 1 from Brier's Swamp | YDM-TM | RT | Yes | N/A | 8/3/2007 |
| AIB5 | H1 | CARBENICILLIN S1RM1LLLSSL 2 | CARBENICILLIN S1RM1LLLSSL 2 | Soil 1 from Brier's Swamp | YDM-TM | RT | Yes | N/A | 8/3/2007 |
| AIB5 | H2 | CARBENICILLIN S1RM1LLLSSL 3 | CARBENICILLIN S1RM1LLLSSL 3 | Soil 1 from Brier's Swamp | YDM-TM | RT | Yes | N/A | 8/3/2007 |
| AIB5 | H3 | DICLO S1RM1LLLSSL 1 | DICLO S1RM1LLLSSL 1 | Soil 1 from Brier's Swamp | YDM-TM | RT | Yes | N/A | 8/3/2007 |
| AIB5 | H4 | DICLO S1RM1LLLSSL 2 | DICLO S1RM1LLLSSL 2 | Soil 1 from Brier's Swamp | YDM-TM | RT | Yes | N/A | 8/3/2007 |
| AIB5 | H5 | DICLO S1RM1LLLSSL 3 | DICLO S1RM1LLLSSL 3 | Soil 1 from Brier's Swamp | YDM-TM | RT | Yes | N/A | 8/3/2007 |
| AIB5 | H6 | CHLORAM S1RM1LLLSSL 1 | CHLORAM S1RM1LLLSSL 1 | Soil 1 from Brier's Swamp | YDM-TM | RT | Yes | N/A | 8/3/2007 |
| AIB5 | H7 | CHLORAM S1RM1LLLSSL 2 | CHLORAM S1RM1LLLSSL 2 | Soil 1 from Brier's Swamp | YDM-TM | RT | Yes | N/A | 8/3/2007 |
| AIB5 | H8 | CHLORAM S1RM1LLLSSL 3 | CHLORAM S1RM1LLLSSL 3 | Soil 1 from Brier's Swamp | YDM-TM | RT | Yes | N/A | 8/3/2007 |
| AIB5 | H9 | THIAMPHENI S1RM1LLLSSL 1 | THIAMPHENI S1RM1LLLSSL 1 | Soil 1 from Brier's Swamp | YDM-TM | RT | Yes | N/A | 8/3/2007 |
| AIB5 | H10 | THIAMPHENI S1RM1LLLSSL 2 | THIAMPHENI S1RM1LLLSSL 2 | Soil 1 from Brier's Swamp | YDM-TM | RT | Yes | N/A | 8/3/2007 |
| AIB5 | I1 | THIAMPHENI S1RM1LLLSSL 3 | THIAMPHENI S1RM1LLLSSL 3 | Soil 1 from Brier's Swamp | YDM-TM | RT | Yes | N/A | 8/3/2007 |
| AIB5 | I2 | MAFENIDE S1RM1LLLSSL 1 | MAFENIDE S1RM1LLLSSL 1 | Soil 1 from Brier's Swamp | YDM-TM | RT | Yes | N/A | 8/3/2007 |
| AIB5 | I3 | MAFENIDE S1RM1LLLSSL 2 | MAFENIDE S1RM1LLLSSL 2 | Soil 1 from Brier's Swamp | YDM-TM | RT | Yes | N/A | 8/3/2007 |
| AIB5 | I4 | MAFENIDE S1RM1LLLSSL 3 | MAFENIDE S1RM1LLLSSL 3 | Soil 1 from Brier's Swamp | YDM-TM | RT | Yes | N/A | 8/3/2007 |
| AIB5 | I5 | TETRA S1RM1LLLSSL 1 | TETRA S1RM1LLLSSL 1 | Soil 1 from Brier's Swamp | YDM-TM | RT | Yes | N/A | 8/3/2007 |
| AIB5 | I6 | TETRA S1RM1LLLSSL 2 | TETRA S1RM1LLLSSL 2 | Soil 1 from Brier's Swamp | YDM-TM | RT | Yes | N/A | 8/3/2007 |
| AIB5 | I7 | TETRA S1RM1LLLSSL 3 | TETRA S1RM1LLLSSL 3 | Soil 1 from Brier's Swamp | YDM-TM | RT | Yes | N/A | 8/3/2007 |
| AIB5 | I8 | OXYTET S1RM1LLLSSL 1 | OXYTET S1RM1LLLSSL 1 | Soil 1 from Brier's Swamp | YDM-TM | RT | Yes | N/A | 8/3/2007 |
| AIB5 | I9 | OXYTET S1RM1LLLSSL 2 | OXYTET S1RM1LLLSSL 2 | Soil 1 from Brier's Swamp | YDM-TM | RT | Yes | N/A | 8/3/2007 |
| AIB5 | I10 | OXYTET S1RM1LLLSSL 3 | OXYTET S1RM1LLLSSL 3 | Soil 1 from Brier's Swamp | YDM-TM | RT | Yes | N/A | 8/3/2007 |
| AIB5 | J1 | MINO S1RM1LLLSSL 1 | MINO S1RM1LLLSSL 1 | Soil 1 from Brier's Swamp | YDM-TM | RT | Yes | N/A | 8/3/2007 |

Figure 10 (Cont.)

| AIB5 | J2 | MINO S1RM1LLLSSL 2 | MINO S1RM1LLLSSL 2 | YDM-TM | RT | Yes | N/A | 8/3/2007 |
|---|---|---|---|---|---|---|---|---|
| AIB5 | J3 | MINO S1RM1LLLSSL 3 | MINO S1RM1LLLSSL 3 | YDM-TM | RT | Yes | N/A | 8/3/2007 |
| AIB5 | J4 | D-CYCLO S1RM1LLLSSL 1 | D-CYCLO S1RM1LLLSSL 1 | YDM-TM | RT | Yes | N/A | 8/3/2007 |
| AIB5 | J5 | D-CYCLO S1RM1LLLSSL 2 | D-CYCLO S1RM1LLLSSL 2 | YDM-TM | RT | Yes | N/A | 8/3/2007 |
| AIB5 | J6 | D-CYCLO S1RM1LLLSSL 3 | D-CYCLO S1RM1LLLSSL 3 | YDM-TM | RT | Yes | N/A | 8/3/2007 |
| AIB5 | J7 | VANCO S1RM1LLLSSL 1 | VANCO S1RM1LLLSSL 1 | YDM-TM | RT | Yes | N/A | 8/3/2007 |
| AIB5 | J8 | VANCO S1RM1LLLSSL 2 | VANCO S1RM1LLLSSL 2 | YDM-TM | RT | Yes | N/A | 8/3/2007 |
| AIB5 | J9 | VANCO S1RM1LLLSSL 3 | VANCO S1RM1LLLSSL 3 | YDM-TM | RT | Yes | N/A | 8/3/2007 |
| AIB5 | J10 | CIPRO S1NM1LLLSSL1 | CIPRO S1NM1LLLSSL1 | Soil 1 from Alfalfa field with manure,MN | YDM-TM | RT | Yes | N/A | 8/3/2007 |

Figure 10 (Cont.)

| Box | S* | Strain | Label | Source | Media | Temp | Oxygen | Extr |
|---|---|---|---|---|---|---|---|---|
| A1B6 | A1 | CIPRO SINM1LL1SSL2 | CIPRO SINM1LL1SSL2 | Soil 1 from Alfalfa field with manure, MN | YDM-TM | RT | Yes | N/A |
| A1B6 | A2 | CIPRO SINM1LL1SSL3 | CIPRO SINM1LL1SSL3 | Soil 1 from Alfalfa field with manure, MN | YDM-TM | RT | Yes | N/A |
| A1B6 | A3 | LEVO SINM1LL1SSL1 | LEVO SINM1LL1SSL1 | Soil 1 from Alfalfa field with manure, MN | YDM-TM | RT | Yes | N/A |
| A1B6 | A4 | LEVO SINM1LL1SSL2 | LEVO SINM1LL1SSL2 | Soil 1 from Alfalfa field with manure, MN | YDM-TM | RT | Yes | N/A |
| A1B6 | A5 | LEVO SINM1LL1SSL3 | LEVO SINM1LL1SSL3 | Soil 1 from Alfalfa field with manure, MN | YDM-TM | RT | Yes | N/A |
| A1B6 | A6 | SISO SINM1LL1SSL1 | SISO SINM1LL1SSL1 | Soil 1 from Alfalfa field with manure, MN | YDM-TM | RT | Yes | N/A |
| A1B6 | A7 | SISO SINM1LL1SSL2 | SISO SINM1LL1SSL2 | Soil 1 from Alfalfa field with manure, MN | YDM-TM | RT | Yes | N/A |
| A1B6 | A8 | SISO SINM1LL1SSL3 | SISO SINM1LL1SSL3 | Soil 1 from Alfalfa field with manure, MN | YDM-TM | RT | Yes | N/A |
| A1B6 | A9 | GENTAMICIN SINM1LL1SSL1 | GENTAMICIN SINM1LL1SSL1 | Soil 1 from Alfalfa field with manure, MN | YDM-TM | RT | Yes | N/A |
| A1B6 | A10 | GENTAMICIN SINM1LL1SSL2 | GENTAMICIN SINM1LL1SSL2 | Soil 1 from Alfalfa field with manure, MN | YDM-TM | RT | Yes | N/A |
| A1B6 | B1 | GENTAMICIN SINM1LL1SSL3 | GENTAMICIN SINM1LL1SSL3 | Soil 1 from Alfalfa field with manure, MN | YDM-TM | RT | Yes | N/A |
| A1B6 | B2 | KANAMICIN SINM1LL1SSL1 | KANAMICIN SINM1LL1SSL1 | Soil 1 from Alfalfa field with manure, MN | YDM-TM | RT | Yes | N/A |
| A1B6 | B3 | KANAMICIN SINM1LL1SSL2 | KANAMICIN SINM1LL1SSL2 | Soil 1 from Alfalfa field with manure, MN | YDM-TM | RT | Yes | N/A |
| A1B6 | B4 | KANAMICIN SINM1LL1SSL3 | KANAMICIN SINM1LL1SSL3 | Soil 1 from Alfalfa field with manure, MN | YDM-TM | RT | Yes | N/A |
| A1B6 | B5 | AMIKACIN SINM1LL1SSL1 | AMIKACIN SINM1LL1SSL1 | Soil 1 from Alfalfa field with manure, MN | YDM-TM | RT | Yes | N/A |
| A1B6 | B6 | AMIKACIN SINM1LL1SSL2 | AMIKACIN SINM1LL1SSL2 | Soil 1 from Alfalfa field with manure, MN | YDM-TM | RT | Yes | N/A |
| A1B6 | B7 | AMIKACIN SINM1LL1SSL3 | AMIKACIN SINM1LL1SSL3 | Soil 1 from Alfalfa field with manure, MN | YDM-TM | RT | Yes | N/A |
| A1B6 | B8 | PENICILLIN G SINM1LL1SSL1 | PENICILLIN G SINM1LL1SSL1 | Soil 1 from Alfalfa field with manure, MN | YDM-TM | RT | Yes | N/A |
| A1B6 | B9 | PENICILLIN G SINM1LL1SSL2 | PENICILLIN G SINM1LL1SSL2 | Soil 1 from Alfalfa field with manure, MN | YDM-TM | RT | Yes | N/A |
| A1B6 | B10 | PENICILLIN G SINM1LL1SSL3 | PENICILLIN G SINM1LL1SSL3 | Soil 1 from Alfalfa field with manure, MN | YDM-TM | RT | Yes | N/A |
| A1B6 | C1 | CARBENICILLIN SINM1LL1SSL1 | CARBENICILLIN SINM1LL1SSL1 | Soil 1 from Alfalfa field with manure, MN | YDM-TM | RT | Yes | N/A |
| A1B6 | C2 | CARBENICILLIN SINM1LL1SSL2 | CARBENICILLIN SINM1LL1SSL2 | Soil 1 from Alfalfa field with manure, MN | YDM-TM | RT | Yes | N/A |

Figure 11

| | | | | | | | |
|---|---|---|---|---|---|---|---|
| AIB6 | C3 | CARBENICILLIN S1NM1LLLSSL 3 | CARBENICILLIN S1NM1LLLSSL 3 | Soil 1 from Alfalfa field with manure,MN | YDM-TM | RT | Yes | N/A |
| AIB6 | C4 | DICLO S1NM1LLLSSL 1 | DICLO S1NM1LLLSSL 1 | Soil 1 from Alfalfa field with manure,MN | YDM-TM | RT | Yes | N/A |
| AIB6 | C5 | DICLO S1NM1LLLSSL 2 | DICLO S1NM1LLLSSL 2 | Soil 1 from Alfalfa field with manure,MN | YDM-TM | RT | Yes | N/A |
| AIB6 | C6 | DICLO S1NM1LLLSSL 3 | DICLO S1NM1LLLSSL 3 | Soil 1 from Alfalfa field with manure,MN | YDM-TM | RT | Yes | N/A |
| AIB6 | C7 | CHLORAM S1NM1LLLSSL 1 | CHLORAM S1NM1LLLSSL 1 | Soil 1 from Alfalfa field with manure,MN | YDM-TM | RT | Yes | N/A |
| AIB6 | C8 | CHLORAM S1NM1LLLSSL 2 | CHLORAM S1NM1LLLSSL 2 | Soil 1 from Alfalfa field with manure,MN | YDM-TM | RT | Yes | N/A |
| AIB6 | C9 | CHLORAM S1NM1LLLSSL 3 | CHLORAM S1NM1LLLSSL 3 | Soil 1 from Alfalfa field with manure,MN | YDM-TM | RT | Yes | N/A |
| AIB6 | C10 | NALIDIXIC S1NM1LLLSSL 1 | NALIDIXIC S1NM1LLLSSL 1 | Soil 1 from Alfalfa field with manure,MN | YDM-TM | RT | Yes | N/A |
| AIB6 | D1 | NALIDIXIC S1NM1LLLSSL 2 | NALIDIXIC S1NM1LLLSSL 2 | Soil 1 from Alfalfa field with manure,MN | YDM-TM | RT | Yes | |
| AIB6 | D2 | NALIDIXIC S1NM1LLLSSL 3 | NALIDIXIC S1NM1LLLSSL 3 | Soil 1 from Alfalfa field with manure,MN | YDM-TM | RT | Yes | N/A |
| AIB6 | D3 | THIAMPHENI S1NM1LLLSSL 1 | THIAMPHENI S1NM1LLLSSL 1 | Soil 1 from Alfalfa field with manure,MN | YDM-TM | RT | Yes | N/A |
| AIB6 | D4 | THIAMPHENI S1NM1LLLSSL 2 | THIAMPHENI S1NM1LLLSSL 2 | Soil 1 from Alfalfa field with manure,MN | YDM-TM | RT | Yes | N/A |
| AIB6 | D5 | THIAMPHENI S1NM1LLLSSL 3 | THIAMPHENI S1NM1LLLSSL 3 | Soil 1 from Alfalfa field with manure,MN | YDM-TM | RT | Yes | N/A |
| AIB6 | D6 | TRIMETHO S1NM1LLLSSL 1 | TRIMETHO S1NM1LLLSSL 1 | Soil 1 from Alfalfa field with manure,MN | YDM-TM | RT | Yes | N/A |
| AIB6 | D7 | TRIMETHO S1NM1LLLSSL 2 | TRIMETHO S1NM1LLLSSL 2 | Soil 1 from Alfalfa field with manure,MN | YDM-TM | RT | Yes | N/A |
| AIB6 | D8 | TRIMETHO S1NM1LLLSSL 3 | TRIMETHO S1NM1LLLSSL 3 | Soil 1 from Alfalfa field with manure,MN | YDM-TM | RT | Yes | N/A |
| AIB6 | D9 | MAFENIDE S1NM1LLLSSL 1 | MAFENIDE S1NM1LLLSSL 1 | Soil 1 from Alfalfa field with manure,MN | YDM-TM | RT | Yes | N/A |
| AIB6 | D10 | MAFENIDE S1NM1LLLSSL 2 | MAFENIDE S1NM1LLLSSL 2 | Soil 1 from Alfalfa field with manure,MN | YDM-TM | RT | Yes | N/A |
| AIB6 | E1 | MAFENIDE S1NM1LLLSSL 3 | MAFENIDE S1NM1LLLSSL 3 | Soil 1 from Alfalfa field with manure,MN | YDM-TM | RT | Yes | N/A |
| AIB6 | E2 | TETRA S1NM1LLLSSL 1 | TETRA S1NM1LLLSSL 1 | Soil 1 from Alfalfa field with manure,MN | YDM-TM | RT | Yes | N/A |
| AIB6 | E3 | TETRA S1NM1LLLSSL 2 | TETRA S1NM1LLLSSL 2 | Soil 1 from Alfalfa field with manure,MN | YDM-TM | RT | Yes | N/A |
| AIB6 | E4 | TETRA S1NM1LLLSSL 3 | TETRA S1NM1LLLSSL 3 | Soil 1 from Alfalfa field with manure,MN | YDM-TM | RT | Yes | N/A |
| AIB6 | E5 | OXYTET S1NM1LLLSSL 1 | OXYTET S1NM1LLLSSL 1 | Soil 1 from Alfalfa field with manure,MN | YDM-TM | RT | Yes | N/A |

Figure 11 (Cont.)

| | | | | | | | |
|---|---|---|---|---|---|---|---|
| AIB6 | E6 | OXYTET S1NM1LLLSSL 2 | OXYTET S1NM1LLLSSL 2 | Soil 1 from Alfalfa field with manure,MN | YDM-TM | RT | Yes | N/A |
| AIB6 | E7 | OXYTET S1NM1LLLSSL 3 | OXYTET S1NM1LLLSSL 3 | Soil 1 from Alfalfa field with manure,MN | YDM-TM | RT | Yes | N/A |
| AIB6 | E8 | D-CYCLO S1NM1LLLSSL 1 | D-CYCLO S1NM1LLLSSL 1 | Soil 1 from Alfalfa field with manure,MN | YDM-TM | RT | Yes | N/A |
| AIB6 | E9 | D-CYCLO S1NM1LLLSSL 2 | D-CYCLO S1NM1LLLSSL 2 | Soil 1 from Alfalfa field with manure,MN | YDM-TM | RT | Yes | N/A |
| AIB6 | E10 | D-CYCLO S1NM1LLLSSL 3 | D-CYCLO S1NM1LLLSSL 3 | Soil 1 from Alfalfa field with manure,MN | YDM-TM | RT | Yes | N/A |
| AIB6 | F1 | VANCO S1NM1LLLSSL 1 | VANCO S1NM1LLLSSL 1 | Soil 1 from Alfalfa field with manure,MN | YDM-TM | RT | Yes | N/A |
| AIB6 | F2 | VANCO S1NM1LLLSSL 2 | VANCO S1NM1LLLSSL 2 | Soil 1 from Alfalfa field with manure,MN | YDM-TM | RT | Yes | N/A |
| AIB6 | F3 | VANCO S1NM1LLLSSL 3 | VANCO S1NM1LLLSSL 3 | Soil 1 from Alfalfa field with manure,MN | YDM-TM | RT | Yes | N/A |
| AIB6 | F4 | CIPRO S1AM1LLLSSL1 | CIPRO S1AM1LLLSSL1 | Soil 1 from 3 mix of pristine soils, PA | YDM-TM | RT | Yes | N/A |
| AIB6 | F5 | CIPRO S1AM1LLLSSL2 | CIPRO S1AM1LLLSSL2 | Soil 1 from 3 mix of pristine soils, PA | YDM-TM | RT | Yes | N/A |
| AIB6 | F6 | CIPRO S1AM1LLLSSL3 | CIPRO S1AM1LLLSSL3 | Soil 1 from 3 mix of pristine soils, PA | YDM-TM | RT | Yes | N/A |
| AIB6 | F7 | SISO S1AM1LLLSSL 1 | SISO S1AM1LLLSSL 1 | Soil 1 from 3 mix of pristine soils, PA | YDM-TM | RT | Yes | N/A |
| AIB6 | F8 | SISO S1AM1LLLSSL 2 | SISO S1AM1LLLSSL 2 | Soil 1 from 3 mix of pristine soils, PA | YDM-TM | RT | Yes | N/A |
| AIB6 | F9 | SISO S1AM1LLLSSL 3 | SISO S1AM1LLLSSL 3 | Soil 1 from 3 mix of pristine soils, PA | YDM-TM | RT | Yes | N/A |
| AIB6 | F10 | GENTAMICIN S1AM1LLLSSL 1 | GENTAMICIN S1AM1LLLSSL 1 | Soil 1 from 3 mix of pristine soils, PA | YDM-TM | RT | Yes | N/A |
| AIB6 | G1 | GENTAMICIN S1AM1LLLSSL 2 | GENTAMICIN S1AM1LLLSSL 2 | Soil 1 from 3 mix of pristine soils, PA | YDM-TM | RT | Yes | N/A |
| AIB6 | G2 | GENTAMICIN S1AM1LLLSSL 3 | GENTAMICIN S1AM1LLLSSL 3 | Soil 1 from 3 mix of pristine soils, PA | YDM-TM | RT | Yes | N/A |
| AIB6 | G3 | KANAMICIN S1AM1LLLSSL 1 | KANAMICIN S1AM1LLLSSL 1 | Soil 1 from 3 mix of pristine soils, PA | YDM-TM | RT | Yes | N/A |
| AIB6 | G4 | KANAMICIN S1AM1LLLSSL 2 | KANAMICIN S1AM1LLLSSL 2 | Soil 1 from 3 mix of pristine soils, PA | YDM-TM | RT | Yes | N/A |
| AIB6 | G5 | KANAMICIN S1AM1LLLSSL 3 | KANAMICIN S1AM1LLLSSL 3 | Soil 1 from 3 mix of pristine soils, PA | YDM-TM | RT | Yes | N/A |
| AIB6 | G6 | AMIKACIN S1AM1LLLSSL 1 | AMIKACIN S1AM1LLLSSL 1 | Soil 1 from 3 mix of pristine soils, PA | YDM-TM | RT | Yes | N/A |
| AIB6 | G7 | AMIKACIN S1AM1LLLSSL 2 | AMIKACIN S1AM1LLLSSL 2 | Soil 1 from 3 mix of pristine soils, PA | YDM-TM | RT | Yes | N/A |
| AIB6 | G8 | AMIKACIN S1AM1LLLSSL 3 | AMIKACIN S1AM1LLLSSL 3 | Soil 1 from 3 mix of pristine soils, PA | YDM-TM | RT | Yes | N/A |

Figure 11 (Cont.)

| | | | | | | |
|---|---|---|---|---|---|---|
| AIB6 | G9 | PENICILLIN S1AM1LLLSSL 1 | PENICILLIN G S1AM1LLLSSL 1 | Soil 1 from 3 mix of pristine soils, PA | YDM-TM | RT | Yes | N/A |
| AIB6 | G10 | PENICILLIN S1AM1LLLSSL 2 | PENICILLIN G S1AM1LLLSSL 2 | Soil 1 from 3 mix of pristine soils, PA | YDM-TM | RT | Yes | N/A |
| AIB6 | H1 | PENICILLIN S1AM1LLLSSL 3 | PENICILLIN G S1AM1LLLSSL 3 | Soil 1 from 3 mix of pristine soils, PA | YDM-TM | RT | Yes | N/A |
| AIB6 | H2 | CARBENICILLIN S1AM1LLLSSL 1 | CARBENICILLIN S1AM1LLLSSL 1 | Soil 1 from 3 mix of pristine soils, PA | YDM-TM | RT | Yes | N/A |
| AIB6 | H3 | CARBENICILLIN S1AM1LLLSSL 2 | CARBENICILLIN S1AM1LLLSSL 2 | Soil 1 from 3 mix of pristine soils, PA | YDM-TM | RT | Yes | N/A |
| AIB6 | H4 | CARBENICILLIN S1AM1LLLSSL 3 | CARBENICILLIN S1AM1LLLSSL 3 | Soil 1 from 3 mix of pristine soils, PA | YDM-TM | RT | Yes | N/A |
| AIB6 | H5 | DICLO S1AM1LLLSSL 1 | DICLO S1AM1LLLSSL 1 | Soil 1 from 3 mix of pristine soils, PA | YDM-TM | RT | Yes | N/A |
| AIB6 | H6 | DICLO S1AM1LLLSSL 2 | DICLO S1AM1LLLSSL 2 | Soil 1 from 3 mix of pristine soils, PA | YDM-TM | RT | Yes | N/A |
| AIB6 | H7 | DICLO S1AM1LLLSSL 3 | DICLO S1AM1LLLSSL 3 | Soil 1 from 3 mix of pristine soils, PA | YDM-TM | | | N/A |
| AIB6 | H8 | CHLORAM S1AM1LLLSSL 1 | CHLORAM S1AM1LLLSSL 1 | Soil 1 from 3 mix of pristine soils, PA | YDM-TM | RT | Yes | N/A |
| AIB6 | H9 | CHLORAM S1AM1LLLSSL 2 | CHLORAM S1AM1LLLSSL 2 | Soil 1 from 3 mix of pristine soils, PA | YDM-TM | RT | Yes | N/A |
| AIB6 | H10 | CHLORAM S1AM1LLLSSL 3 | CHLORAM S1AM1LLLSSL 3 | Soil 1 from 3 mix of pristine soils, PA | YDM-TM | RT | Yes | N/A |
| AIB6 | I1 | NALIDIXIC S1AM1LLLSSL 1 | NALIDIXIC S1AM1LLLSSL 1 | Soil 1 from 3 mix of pristine soils, PA | YDM-TM | RT | Yes | N/A |
| AIB6 | I2 | NALIDIXIC S1AM1LLLSSL 2 | NALIDIXIC S1AM1LLLSSL 2 | Soil 1 from 3 mix of pristine soils, PA | YDM-TM | RT | Yes | N/A |
| AIB6 | I3 | NALIDIXIC S1AM1LLLSSL 3 | NALIDIXIC S1AM1LLLSSL 3 | Soil 1 from 3 mix of pristine soils, PA | YDM-TM | RT | Yes | N/A |
| AIB6 | I4 | THIAMPHENI S1AM1LLLSSL 1 | THIAMPHENI S1AM1LLLSSL 1 | Soil 1 from 3 mix of pristine soils, PA | YDM-TM | RT | Yes | N/A |
| AIB6 | I5 | THIAMPHENI S1AM1LLLSSL 2 | THIAMPHENI S1AM1LLLSSL 2 | Soil 1 from 3 mix of pristine soils, PA | YDM-TM | RT | Yes | N/A |
| AIB6 | I6 | THIAMPHENI S1AM1LLLSSL 3 | THIAMPHENI S1AM1LLLSSL 3 | Soil 1 from 3 mix of pristine soils, PA | YDM-TM | RT | Yes | N/A |
| AIB6 | I7 | SULFISOXA S1AM1LLLSSL 1 | SULFISOXA S1AM1LLLSSL 1 | Soil 1 from 3 mix of pristine soils, PA | YDM-TM | RT | Yes | N/A |
| AIB6 | I8 | SULFISOXA S1AM1LLLSSL 2 | SULFISOXA S1AM1LLLSSL 2 | Soil 1 from 3 mix of pristine soils, PA | YDM-TM | RT | Yes | N/A |
| AIB6 | I9 | SULFISOXA S1AM1LLLSSL 3 | SULFISOXA S1AM1LLLSSL 3 | Soil 1 from 3 mix of pristine soils, PA | YDM-TM | RT | Yes | N/A |
| AIB6 | I10 | TRIMETHO S1AM1LLLSSL 1 | TRIMETHO S1AM1LLLSSL 1 | Soil 1 from 3 mix of pristine soils, PA | YDM-TM | RT | Yes | N/A |
| AIB6 | J1 | TRIMETHO S1AM1LLLSSL 2 | TRIMETHO S1AM1LLLSSL 2 | Soil 1 from 3 mix of pristine soils, PA | YDM-TM | RT | Yes | N/A |

Figure 11 (Cont.)

| AIB6 | J2 | TRIMETHO S1AM1LLLSSL 3 | TRIMETHO S1AM1LLLSSL 3 | Soil 1 from 3 mix of pristine soils, PA | YDM-TM | RT | Yes | N/A |
|---|---|---|---|---|---|---|---|---|
| AIB6 | J3 | MAFENIDE S1AM1LLLSSL 1 | MAFENIDE S1AM1LLLSSL 1 | Soil 1 from 3 mix of pristine soils, PA | YDM-TM | RT | Yes | N/A |
| AIB6 | J4 | MAFENIDE S1AM1LLLSSL 2 | MAFENIDE S1AM1LLLSSL 2 | Soil 1 from 3 mix of pristine soils, PA | YDM-TM | RT | Yes | N/A |
| AIB6 | J5 | MAFENIDE S1AM1LLLSSL 3 | MAFENIDE S1AM1LLLSSL 3 | Soil 1 from 3 mix of pristine soils, PA | YDM-TM | RT | Yes | N/A |
| AIB6 | J6 | SULFAMET S1AM1LLLSSL 1 | SULFAMET S1AM1LLLSSL 1 | Soil 1 from 3 mix of pristine soils, PA | YDM-TM | RT | Yes | N/A |
| AIB6 | J7 | SULFAMET S1AM1LLLSSL 2 | SULFAMET S1AM1LLLSSL 2 | Soil 1 from 3 mix of pristine soils, PA | YDM-TM | RT | Yes | N/A |
| AIB6 | J8 | SULFAMET S1AM1LLLSSL 3 | SULFAMET S1AM1LLLSSL 3 | Soil 1 from 3 mix of pristine soils, PA | YDM-TM | RT | Yes | N/A |
| AIB6 | J9 | TETRA S1AM1LLLSSL 1 | TETRA S1AM1LLLSSL 1 | Soil 1 from 3 mix of pristine soils, PA | YDM-TM | RT | Yes | N/A |
| AIB6 | J10 | TETRA S1AM1LLLSSL 2 | TETRA S1AM1LLLSSL 2 | Soil 1 from 3 mix of pristine soils, PA | YDM-TM | RT | Yes | N/A |

Figure 11 (Cont.)

| Box | S* | Strain | Label | Source | Media | Temp | Oxygen | Extr | |
|---|---|---|---|---|---|---|---|---|---|
| AIB7 | A1 | TETRA S1AM1LLLSSL 3 | TETRA S1AM1LLLSSL 3 | Soil 1 from 3 mix of pristine soils, PA | YDM-TM | RT | Yes | N/A | 8/3/2007 |
| AIB7 | A2 | OXYTET S1AM1LLLSSL 1 | OXYTET S1AM1LLLSSL 1 | Soil 1 from 3 mix of pristine soils, PA | YDM-TM | RT | Yes | N/A | 8/3/2007 |
| AIB7 | A3 | OXYTET S1AM1LLLSSL 2 | OXYTET S1AM1LLLSSL 2 | Soil 1 from 3 mix of pristine soils, PA | YDM-TM | RT | Yes | N/A | 8/3/2007 |
| AIB7 | A4 | OXYTET S1AM1LLLSSL 3 | OXYTET S1AM1LLLSSL 3 | Soil 1 from 3 mix of pristine soils, PA | YDM-TM | RT | Yes | N/A | 8/3/2007 |
| AIB7 | A5 | MINO S1AM1LLLSSL 1 | MINO S1AM1LLLSSL 1 | Soil 1 from 3 mix of pristine soils, PA | YDM-TM | RT | Yes | N/A | 8/3/2007 |
| AIB7 | A6 | MINO S1AM1LLLSSL 2 | MINO S1AM1LLLSSL 2 | Soil 1 from 3 mix of pristine soils, PA | YDM-TM | RT | Yes | N/A | 8/3/2007 |
| AIB7 | A7 | MINO S1AM1LLLSSL 3 | MINO S1AM1LLLSSL 3 | Soil 1 from 3 mix of pristine soils, PA | YDM-TM | RT | Yes | N/A | 8/3/2007 |
| AIB7 | A8 | D-CYCLO S1AM1LLLSSL 1 | D-CYCLO S1AM1LLLSSL 1 | Soil 1 from 3 mix of pristine soils, PA | YDM-TM | RT | Yes | N/A | 8/3/2007 |
| AIB7 | A9 | D-CYCLO S1AM1LLLSSL 2 | D-CYCLO S1AM1LLLSSL 2 | Soil 1 from 3 mix of pristine soils, PA | YDM-TM | RT | Yes | N/A | 8/3/2007 |
| AIB7 | A10 | D-CYCLO S1AM1LLLSSL 3 | D-CYCLO S1AM1LLLSSL 3 | Soil 1 from 3 mix of pristine soils, PA | YDM-TM | RT | Yes | N/A | 8/3/2007 |
| AIB7 | B1 | VANCO S1AM1LLLSSL 1 | VANCO S1AM1LLLSSL 1 | Soil 1 from 3 mix of pristine soils, PA | YDM-TM | RT | Yes | N/A | 8/3/2007 |
| AIB7 | B2 | VANCO S1AM1LLLSSL 2 | VANCO S1AM1LLLSSL 2 | Soil 1 from 3 mix of pristine soils, PA | YDM-TM | RT | Yes | N/A | 8/3/2007 |
| AIB7 | B3 | VANCO S1AM1LLLSSL 3 | VANCO S1AM1LLLSSL 3 | Soil 1 from 3 mix of pristine soils, PA | YDM-TM | RT | Yes | N/A | 8/3/2007 |
| AIB7 | B4 | CIPRO S2RM1LLLSSL1 | CIPRO S2RM1LLLSSL1 | Soil 2 from Raccoon Ledger, MA | YDM-TM | RT | Yes | N/A | 8/3/2007 |
| AIB7 | B5 | CIPRO S2RM1LLLSSL2 | CIPRO S2RM1LLLSSL2 | Soil 2 from Raccoon Ledger, MA | YDM-TM | RT | Yes | N/A | 8/3/2007 |
| AIB7 | B6 | CIPRO S2RM1LLLSSL3 | CIPRO S2RM1LLLSSL3 | Soil 2 from Raccoon Ledger, MA | YDM-TM | RT | Yes | N/A | 8/3/2007 |
| AIB7 | B7 | LEVO S2RM1LLLSSL 1 | LEVO S2RM1LLLSSL 1 | Soil 2 from Raccoon Ledger, MA | YDM-TM | RT | Yes | N/A | 8/3/2007 |
| AIB7 | B8 | LEVO S2RM1LLLSSL 2 | LEVO S2RM1LLLSSL 2 | Soil 2 from Raccoon Ledger, MA | YDM-TM | RT | Yes | N/A | 8/3/2007 |
| AIB7 | B9 | LEVO S2RM1LLLSSL 3 | LEVO S2RM1LLLSSL 3 | Soil 2 from Raccoon Ledger, MA | YDM-TM | RT | Yes | N/A | 8/3/2007 |
| AIB7 | B10 | SISO S2RM1LLLSSL 1 | SISO S2RM1LLLSSL 1 | Soil 2 from Raccoon Ledger, MA | YDM-TM | RT | Yes | N/A | 8/3/2007 |
| AIB7 | C1 | SISO S2RM1LLLSSL 2 | SISO S2RM1LLLSSL 2 | Soil 2 from Raccoon Ledger, MA | YDM-TM | RT | Yes | N/A | 8/3/2007 |
| AIB7 | C2 | SISO S2RM1LLLSSL 3 | SISO S2RM1LLLSSL 3 | Soil 2 from Raccoon Ledger, MA | YDM-TM | RT | Yes | N/A | 8/3/2007 |

Figure 12

| AIB7 | C3 | GENTAMICIN S2RM1LLLSSL 1 | GENTAMICIN S2RM1LLLSSL 1 | Soil 2 from Raccoon Ledger, MA | YDM-TM | RT | Yes | N/A | 8/3/2007 |
|---|---|---|---|---|---|---|---|---|---|
| AIB7 | C4 | GENTAMICIN S2RM1LLLSSL 2 | GENTAMICIN S2RM1LLLSSL 2 | Soil 2 from Raccoon Ledger, MA | YDM-TM | RT | Yes | N/A | 8/3/2007 |
| AIB7 | C5 | GENTAMICIN S2RM1LLLSSL 3 | GENTAMICIN S2RM1LLLSSL 3 | Soil 2 from Raccoon Ledger, MA | YDM-TM | RT | Yes | N/A | 8/3/2007 |
| AIB7 | C6 | KANAMICIN S2RM1LLLSSL 1 | KANAMICIN S2RM1LLLSSL 1 | Soil 2 from Raccoon Ledger, MA | YDM-TM | RT | Yes | N/A | 8/3/2007 |
| AIB7 | C7 | KANAMICIN S2RM1LLLSSL 2 | KANAMICIN S2RM1LLLSSL 2 | Soil 2 from Raccoon Ledger, MA | YDM-TM | RT | Yes | N/A | 8/3/2007 |
| AIB7 | C8 | KANAMICIN S2RM1LLLSSL 3 | KANAMICIN S2RM1LLLSSL 3 | Soil 2 from Raccoon Ledger, MA | YDM-TM | RT | Yes | N/A | 8/3/2007 |
| AIB7 | C9 | AMIKACIN S2RM1LLLSSL 1 | AMIKACIN S2RM1LLLSSL 1 | Soil 2 from Raccoon Ledger, MA | YDM-TM | RT | Yes | N/A | 8/3/2007 |
| AIB7 | C10 | AMIKACIN S2RM1LLLSSL 2 | AMIKACIN S2RM1LLLSSL 2 | Soil 2 from Raccoon Ledger, MA | YDM-TM | RT | Yes | N/A | 8/3/2007 |
| AIB7 | D1 | AMIKACIN S2RM1LLLSSL 3 | AMIKACIN S2RM1LLLSSL 3 | Soil 2 from Raccoon Ledger, MA | YDM-TM | RT | Yes | N/A | 8/3/2007 |
| AIB7 | D2 | PENICILLIN G S2RM1LLLSSL 1 | PENICILLIN G S2RM1LLLSSL 1 | Soil 2 from Raccoon Ledger, MA | YDM-TM | RT | Yes | N/A | 8/3/2007 |
| AIB7 | D3 | PENICILLIN G S2RM1LLLSSL 2 | PENICILLIN G S2RM1LLLSSL 2 | Soil 2 from Raccoon Ledger, MA | YDM-TM | RT | Yes | N/A | 8/3/2007 |
| AIB7 | D4 | PENICILLIN G S2RM1LLLSSL 3 | PENICILLIN G S2RM1LLLSSL 3 | Soil 2 from Raccoon Ledger, MA | YDM-TM | RT | Yes | N/A | 8/3/2007 |
| AIB7 | D5 | CARBENICILLIN S2RM1LLLSSL 1 | CARBENICILLIN S2RM1LLLSSL 1 | Soil 2 from Raccoon Ledger, MA | YDM-TM | RT | Yes | N/A | 8/3/2007 |
| AIB7 | D6 | CARBENICILLIN S2RM1LLLSSL 2 | CARBENICILLIN S2RM1LLLSSL 2 | Soil 2 from Raccoon Ledger, MA | YDM-TM | RT | Yes | N/A | 8/3/2007 |
| AIB7 | D7 | CARBENICILLIN S2RM1LLLSSL 3 | CARBENICILLIN S2RM1LLLSSL 3 | Soil 2 from Raccoon Ledger, MA | YDM-TM | RT | Yes | N/A | 8/3/2007 |
| AIB7 | D8 | DICLO S2RM1LLLSSL 1 | DICLO S2RM1LLLSSL 1 | Soil 2 from Raccoon Ledger, MA | YDM-TM | RT | Yes | N/A | 8/3/2007 |
| AIB7 | D9 | DICLO S2RM1LLLSSL 2 | DICLO S2RM1LLLSSL 2 | Soil 2 from Raccoon Ledger, MA | YDM-TM | RT | Yes | N/A | 8/3/2007 |
| AIB7 | D10 | DICLO S2RM1LLLSSL 3 | DICLO S2RM1LLLSSL 3 | Soil 2 from Raccoon Ledger, MA | YDM-TM | RT | Yes | N/A | 8/3/2007 |
| AIB7 | E1 | CHLORAM S2RM1LLLSSL1 | CHLORAM S2RM1LLLSSL1 | Soil 2 from Raccoon Ledger, MA | YDM-TM | RT | Yes | N/A | 8/3/2007 |
| AIB7 | E2 | CHLORAM S2RM1LLLSSL2 | CHLORAM S2RM1LLLSSL2 | Soil 2 from Raccoon Ledger, MA | YDM-TM | RT | Yes | N/A | 8/3/2007 |
| AIB7 | E3 | CHLORAM S2RM1LLLSSL3 | CHLORAM S2RM1LLLSSL3 | Soil 2 from Raccoon Ledger, MA | YDM-TM | RT | Yes | N/A | 8/3/2007 |
| AIB7 | E4 | NALIDIXIC S2RM1LLLSSL 1 | NALIDIXIC S2RM1LLLSSL 1 | Soil 2 from Raccoon Ledger, MA | YDM-TM | RT | Yes | N/A | 8/3/2007 |
| AIB7 | E5 | NALIDIXIC S2RM1LLLSSL 2 | NALIDIXIC S2RM1LLLSSL 2 | Soil 2 from Raccoon Ledger, MA | YDM-TM | RT | Yes | N/A | 8/3/2007 |

Figure 12 (Cont.)

| | | | | | | | |
|---|---|---|---|---|---|---|---|
| A1B7 | E6 | NALIDIXIC S2RM1LLLSSL 3 | NALIDIXIC S2RM1LLLSSL 3 | Soil 2 from Raccoon Ledger, MA | YDM-TM | RT | Yes | N/A | 8/3/2007 |
| A1B7 | E7 | THIAMPHENI S2RM1LLLSSL 1 | THIAMPHENI S2RM1LLLSSL 1 | Soil 2 from Raccoon Ledger, MA | YDM-TM | RT | Yes | N/A | 8/3/2007 |
| A1B7 | E8 | THIAMPHENI S2RM1LLLSSL 2 | THIAMPHENI S2RM1LLLSSL 2 | Soil 2 from Raccoon Ledger, MA | YDM-TM | RT | Yes | N/A | 8/3/2007 |
| A1B7 | E9 | THIAMPHENI S2RM1LLLSSL 3 | THIAMPHENI S2RM1LLLSSL 3 | Soil 2 from Raccoon Ledger, MA | YDM-TM | RT | Yes | N/A | 8/3/2007 |
| A1B7 | E10 | TRIMETHO S2RM1LLLSSL 1 | TRIMETHO S2RM1LLLSSL 1 | Soil 2 from Raccoon Ledger, MA | YDM-TM | RT | Yes | N/A | 8/3/2007 |
| A1B7 | F1 | TRIMETHO S2RM1LLLSSL 2 | TRIMETHO S2RM1LLLSSL 2 | Soil 2 from Raccoon Ledger, MA | YDM-TM | RT | Yes | N/A | 8/3/2007 |
| A1B7 | F2 | TRIMETHO S2RM1LLLSSL 3 | TRIMETHO S2RM1LLLSSL 3 | Soil 2 from Raccoon Ledger, MA | YDM-TM | RT | Yes | N/A | 8/3/2007 |
| A1B7 | F3 | MAFENIDE S2RM1LLLSSL 1 | MAFENIDE S2RM1LLLSSL 1 | Soil 2 from Raccoon Ledger, MA | YDM-TM | RT | Yes | N/A | 8/3/2007 |
| A1B7 | F4 | MAFENIDE S2RM1LLLSSL 2 | MAFENIDE S2RM1LLLSSL 2 | Soil 2 from Raccoon Ledger, MA | YDM-TM | RT | Yes | N/A | 8/3/2007 |
| A1B7 | F5 | MAFENIDE S2RM1LLLSSL 3 | MAFENIDE S2RM1LLLSSL 3 | Soil 2 from Raccoon Ledger, MA | YDM-TM | RT | Yes | N/A | 8/3/2007 |
| A1B7 | F6 | SULFAMET S2RM1LLLSSL 1 | SULFAMET S2RM1LLLSSL 1 | Soil 2 from Raccoon Ledger, MA | YDM-TM | RT | Yes | N/A | 8/3/2007 |
| A1B7 | F7 | SULFAMET S2RM1LLLSSL 2 | SULFAMET S2RM1LLLSSL 2 | Soil 2 from Raccoon Ledger, MA | YDM-TM | RT | Yes | N/A | 8/3/2007 |
| A1B7 | F8 | SULFAMET S2RM1LLLSSL 3 | SULFAMET S2RM1LLLSSL 3 | Soil 2 from Raccoon Ledger, MA | YDM-TM | RT | Yes | N/A | 8/3/2007 |
| A1B7 | F9 | TETRA S2RM1LLLSSL 1 | TETRA S2RM1LLLSSL 1 | Soil 2 from Raccoon Ledger, MA | YDM-TM | RT | Yes | N/A | 8/3/2007 |
| A1B7 | F10 | TETRA S2RM1LLLSSL 2 | TETRA S2RM1LLLSSL 2 | Soil 2 from Raccoon Ledger, MA | YDM-TM | RT | Yes | N/A | 8/3/2007 |
| A1B7 | G1 | TETRA S2RM1LLLSSL 3 | TETRA S2RM1LLLSSL 3 | Soil 2 from Raccoon Ledger, MA | YDM-TM | RT | Yes | N/A | 8/3/2007 |
| A1B7 | G2 | OXYTET S2RM1LLLSSL 1 | OXYTET S2RM1LLLSSL 1 | Soil 2 from Raccoon Ledger, MA | YDM-TM | RT | Yes | N/A | 8/3/2007 |
| A1B7 | G3 | OXYTET S2RM1LLLSSL 2 | OXYTET S2RM1LLLSSL 2 | Soil 2 from Raccoon Ledger, MA | YDM-TM | RT | Yes | N/A | 8/3/2007 |
| A1B7 | G4 | OXYTET S2RM1LLLSSL 3 | OXYTET S2RM1LLLSSL 3 | Soil 2 from Raccoon Ledger, MA | YDM-TM | RT | Yes | N/A | 8/3/2007 |
| A1B7 | G5 | MINO S2RM1LLLSSL 1 | MINO S2RM1LLLSSL 1 | Soil 2 from Raccoon Ledger, MA | YDM-TM | RT | Yes | N/A | 8/3/2007 |
| A1B7 | G6 | MINO S2RM1LLLSSL 2 | MINO S2RM1LLLSSL 2 | Soil 2 from Raccoon Ledger, MA | YDM-TM | RT | Yes | N/A | 8/3/2007 |
| A1B7 | G7 | MINO S2RM1LLLSSL 3 | MINO S2RM1LLLSSL 3 | Soil 2 from Raccoon Ledger, MA | YDM-TM | RT | Yes | N/A | 8/3/2007 |
| A1B7 | G8 | D-CYCLO S2RM1LLLSSL 1 | D-CYCLO S2RM1LLLSSL 1 | Soil 2 from Raccoon Ledger, MA | YDM-TM | RT | Yes | N/A | 8/3/2007 |

Figure 12 (Cont.)

| | | | | | | | |
|---|---|---|---|---|---|---|---|
| AIB7 | G9 | D-CYCLO S2RM1LLLSSL 2 | D-CYCLO S2RM1LLLSSL 2 | Soil 2 from Raccoon Ledger, MA | YDM-TM | RT | Yes | N/A | 8/3/2007 |
| AIB7 | G10 | D-CYCLO S2RM1LLLSSL 3 | D-CYCLO S2RM1LLLSSL 3 | Soil 2 from Raccoon Ledger, MA | YDM-TM | RT | Yes | N/A | 8/3/2007 |
| AIB7 | H1 | VANCO S2RM1LLLSSL 1 | VANCO S2RM1LLLSSL 1 | Soil 2 from Raccoon Ledger, MA | YDM-TM | RT | Yes | N/A | 8/3/2007 |
| AIB7 | H2 | VANCO S2RM1LLLSSL 2 | VANCO S2RM1LLLSSL 2 | Soil 2 from Raccoon Ledger, MA | YDM-TM | RT | Yes | N/A | 8/3/2007 |
| AIB7 | H3 | VANCO S2RM1LLLSSL 3 | VANCO S2RM1LLLSSL 3 | Soil 2 from Raccoon Ledger, MA | YDM-TM | RT | Yes | N/A | 8/3/2007 |
| AIB7 | H4 | CIPRO S1GM1LLLSSL1 | CIPRO S1GM1LLLSSL1 | Soil 1 from Corn field with antibiotic, MA | YDM-TM | RT | Yes | N/A | 8/3/2007 |
| AIB7 | H5 | CIPRO S1GM1LLLSSL2 | CIPRO S1GM1LLLSSL2 | Soil 1 from Corn field with antibiotic, MA | YDM-TM | RT | Yes | N/A | 8/3/2007 |
| AIB7 | H6 | CIPRO S1GM1LLLSSL3 | CIPRO S1GM1LLLSSL3 | Soil 1 from Corn field with antibiotic, MA | YDM-TM | RT | Yes | N/A | 8/3/2007 |
| AIB7 | H7 | LEVO S1GM1LLLSSL 1 | LEVO S1GM1LLLSSL 1 | Soil 1 from Corn field with antibiotic, MA | YDM-TM | RT | Yes | N/A | 8/3/2007 |
| AIB7 | H8 | LEVO S1GM1LLLSSL 2 | LEVO S1GM1LLLSSL 2 | Soil 1 from Corn field with antibiotic, MA | YDM-TM | RT | Yes | N/A | 8/3/2007 |
| AIB7 | H9 | LEVO S1GM1LLLSSL 3 | LEVO S1GM1LLLSSL 3 | Soil 1 from Corn field with antibiotic, MA | YDM-TM | RT | Yes | N/A | 8/3/2007 |
| AIB7 | H10 | SISO S1GM1LLLSSL 1 | SISO S1GM1LLLSSL 1 | Soil 1 from Corn field with antibiotic, MA | YDM-TM | RT | Yes | N/A | 8/3/2007 |
| AIB7 | I1 | SISO S1GM1LLLSSL 2 | SISO S1GM1LLLSSL 2 | Soil 1 from Corn field with antibiotic, MA | YDM-TM | RT | Yes | N/A | 8/3/2007 |
| AIB7 | I2 | SISO S1GM1LLLSSL 3 | SISO S1GM1LLLSSL 3 | Soil 1 from Corn field with antibiotic, MA | YDM-TM | RT | Yes | N/A | 8/3/2007 |
| AIB7 | I3 | GENTAMICIN S1GM1LLLSSL 1 | GENTAMICIN S1GM1LLLSSL 1 | Soil 1 from Corn field with antibiotic, MA | YDM-TM | RT | Yes | N/A | 8/3/2007 |
| AIB7 | I4 | GENTAMICIN S1GM1LLLSSL 2 | GENTAMICIN S1GM1LLLSSL 2 | Soil 1 from Corn field with antibiotic, MA | YDM-TM | RT | Yes | N/A | 8/3/2007 |
| AIB7 | I5 | GENTAMICIN S1GM1LLLSSL 3 | GENTAMICIN S1GM1LLLSSL 3 | Soil 1 from Corn field with antibiotic, MA | YDM-TM | RT | Yes | N/A | 8/3/2007 |
| AIB7 | I6 | KANAMICIN S1GM1LLLSSL 1 | KANAMICIN S1GM1LLLSSL 1 | Soil 1 from Corn field with antibiotic, MA | YDM-TM | RT | Yes | N/A | 8/3/2007 |
| AIB7 | I7 | KANAMICIN S1GM1LLLSSL 2 | KANAMICIN S1GM1LLLSSL 2 | Soil 1 from Corn field with antibiotic, MA | YDM-TM | RT | Yes | N/A | 8/3/2007 |
| AIB7 | I8 | KANAMICIN S1GM1LLLSSL 3 | KANAMICIN S1GM1LLLSSL 3 | Soil 1 from Corn field with antibiotic, MA | YDM-TM | RT | Yes | N/A | 8/3/2007 |
| AIB7 | I9 | AMIKACIN S1GM1LLLSSL 1 | AMIKACIN S1GM1LLLSSL 1 | Soil 1 from Corn field with antibiotic, MA | YDM-TM | RT | Yes | N/A | 8/3/2007 |
| AIB7 | I10 | AMIKACIN S1GM1LLLSSL 2 | AMIKACIN S1GM1LLLSSL 2 | Soil 1 from Corn field with antibiotic, MA | YDM-TM | RT | Yes | N/A | 8/3/2007 |
| AIB7 | J1 | AMIKACIN S1GM1LLLSSL 3 | AMIKACIN S1GM1LLLSSL 3 | Soil 1 from Corn field with antibiotic, MA | YDM-TM | RT | Yes | N/A | 8/3/2007 |

Figure 12 (Cont.)

| AIB7 | J2 | PENICILLIN G SIGM1LLLSSL 1 | PENICILLIN G SIGM1LLLSSL 1 | Soil 1 from Corn field with antibiotic, MA | YDM-TM | RT | Yes | N/A | 8/3/2007 |
|---|---|---|---|---|---|---|---|---|---|
| AIB7 | J3 | PENICILLIN G SIGM1LLLSSL 2 | PENICILLIN G SIGM1LLLSSL 2 | Soil 1 from Corn field with antibiotic, MA | YDM-TM | RT | Yes | N/A | 8/3/2007 |
| AIB7 | J4 | PENICILLIN G SIGM1LLLSSL 3 | PENICILLIN G SIGM1LLLSSL 3 | Soil 1 from Corn field with antibiotic, MA | YDM-TM | RT | Yes | N/A | 8/3/2007 |
| AIB7 | J5 | CARBENICILLIN SIGM1LLLSSL 1 | CARBENICILLIN SIGM1LLLSSL 1 | Soil 1 from Corn field with antibiotic, MA | YDM-TM | RT | Yes | N/A | 8/3/2007 |
| AIB7 | J6 | CARBENICILLIN SIGM1LLLSSL 2 | CARBENICILLIN SIGM1LLLSSL 2 | Soil 1 from Corn field with antibiotic, MA | YDM-TM | RT | Yes | N/A | 8/3/2007 |
| AIB7 | J7 | CARBENICILLIN SIGM1LLLSSL 3 | CARBENICILLIN SIGM1LLLSSL 3 | Soil 1 from Corn field with antibiotic, MA | YDM-TM | RT | Yes | N/A | 8/3/2007 |
| AIB7 | J8 | DICLO SIGM1LLLSSL 1 | DICLO SIGM1LLLSSL 1 | Soil 1 from Corn field with antibiotic, MA | YDM-TM | RT | Yes | N/A | 8/3/2007 |
| AIB7 | J9 | DICLO SIGM1LLLSSL 2 | DICLO SIGM1LLLSSL 2 | Soil 1 from Corn field with antibiotic, MA | YDM-TM | RT | Yes | N/A | 8/3/2007 |
| AIB7 | J10 | DICLO SIGM1LLLSSL 3 | DICLO SIGM1LLLSSL 3 | Soil 1 from Corn field with antibiotic, MA | YDM-TM | RT | Yes | N/A | 8/3/2007 |

Figure 12 (Cont.)

| Box | S* | Strain | Label | Source | Media | Temp | Oxygen | Extr | 8/3/2007 |
|---|---|---|---|---|---|---|---|---|---|
| AIB8 | A1 | CHLORAM SIGM1LLLSSL1 | CHLORAM SIGM1LLLSSL1 | Soil 1 from Corn field with antibiotic, MA | YDM-TM | RT | Yes | N/A | 8/3/2007 |
| AIB8 | A2 | CHLORAM SIGM1LLLSSL2 | CHLORAM SIGM1LLLSSL2 | Soil 1 from Corn field with antibiotic, MA | YDM-TM | RT | Yes | N/A | 8/3/2007 |
| AIB8 | A3 | CHLORAM SIGM1LLLSSL3 | CHLORAM SIGM1LLLSSL3 | Soil 1 from Corn field with antibiotic, MA | YDM-TM | RT | Yes | N/A | 8/3/2007 |
| AIB8 | A4 | NALIDIXIC SIGM1LLLSSL1 | NALIDIXIC SIGM1LLLSSL1 | Soil 1 from Corn field with antibiotic, MA | YDM-TM | RT | Yes | N/A | 8/3/2007 |
| AIB8 | A5 | NALIDIXIC SIGM1LLLSSL2 | NALIDIXIC SIGM1LLLSSL2 | Soil 1 from Corn field with antibiotic, MA | YDM-TM | RT | Yes | N/A | 8/3/2007 |
| AIB8 | A6 | NALIDIXIC SIGM1LLLSSL3 | NALIDIXIC SIGM1LLLSSL3 | Soil 1 from Corn field with antibiotic, MA | YDM-TM | RT | Yes | N/A | 8/3/2007 |
| AIB8 | A7 | THIAMPHENI SIGM1LLLSSL1 | THIAMPHENI SIGM1LLLSSL1 | Soil 1 from Corn field with antibiotic, MA | YDM-TM | RT | Yes | N/A | 8/3/2007 |
| AIB8 | A8 | THIAMPHENI SIGM1LLLSSL2 | THIAMPHENI SIGM1LLLSSL2 | Soil 1 from Corn field with antibiotic, MA | YDM-TM | RT | Yes | N/A | 8/3/2007 |
| AIB8 | A9 | THIAMPHENI SIGM1LLLSSL3 | THIAMPHENI SIGM1LLLSSL3 | Soil 1 from Corn field with antibiotic, MA | YDM-TM | RT | Yes | N/A | 8/3/2007 |
| AIB8 | A10 | SULFISOXA SIGM1LLLSSL1 | SULFISOXA SIGM1LLLSSL1 | Soil 1 from Corn field with antibiotic, MA | YDM-TM | RT | Yes | N/A | 8/3/2007 |
| AIB8 | B1 | SULFISOXA SIGM1LLLSSL2 | SULFISOXA SIGM1LLLSSL2 | Soil 1 from Corn field with antibiotic, MA | YDM-TM | RT | Yes | N/A | 8/3/2007 |
| AIB8 | B2 | SULFISOXA SIGM1LLLSSL3 | SULFISOXA SIGM1LLLSSL3 | Soil 1 from Corn field with antibiotic, MA | YDM-TM | RT | Yes | N/A | 8/3/2007 |
| AIB8 | B3 | TRIMETHO SIGM1LLLSSL1 | TRIMETHO SIGM1LLLSSL1 | Soil 1 from Corn field with antibiotic, MA | YDM-TM | RT | Yes | N/A | 8/3/2007 |
| AIB8 | B4 | TRIMETHO SIGM1LLLSSL2 | TRIMETHO SIGM1LLLSSL2 | Soil 1 from Corn field with antibiotic, MA | YDM-TM | RT | Yes | N/A | 8/3/2007 |
| AIB8 | B5 | TRIMETHO SIGM1LLLSSL3 | TRIMETHO SIGM1LLLSSL3 | Soil 1 from Corn field with antibiotic, MA | YDM-TM | RT | Yes | N/A | 8/3/2007 |
| AIB8 | B6 | MAFENIDE SIGM1LLLSSL1 | MAFENIDE SIGM1LLLSSL1 | Soil 1 from Corn field with antibiotic, MA | YDM-TM | RT | Yes | N/A | 8/3/2007 |
| AIB8 | B7 | MAFENIDE SIGM1LLLSSL2 | MAFENIDE SIGM1LLLSSL2 | Soil 1 from Corn field with antibiotic, MA | YDM-TM | RT | Yes | N/A | 8/3/2007 |
| AIB8 | B8 | MAFENIDE SIGM1LLLSSL3 | MAFENIDE SIGM1LLLSSL3 | Soil 1 from Corn field with antibiotic, MA | YDM-TM | RT | Yes | N/A | 8/3/2007 |
| AIB8 | B9 | SULFAMET SIGM1LLLSSL1 | SULFAMET SIGM1LLLSSL1 | Soil 1 from Corn field with antibiotic, MA | YDM-TM | RT | Yes | N/A | 8/3/2007 |
| AIB8 | B10 | SULFAMET SIGM1LLLSSL2 | SULFAMET SIGM1LLLSSL2 | Soil 1 from Corn field with antibiotic, MA | YDM-TM | RT | Yes | N/A | 8/3/2007 |
| AIB8 | C1 | SULFAMET SIGM1LLLSSL3 | SULFAMET SIGM1LLLSSL3 | Soil 1 from Corn field with antibiotic, MA | YDM-TM | RT | Yes | N/A | 8/3/2007 |
|  |  | TETRA SIGM1LLLSSL1 | TETRA SIGM1LLLSSL1 | Soil 1 from Corn field with antibiotic, MA | YDM-TM | RT | Yes | N/A | 8/3/2007 |

Figure 13

| | | | | | | |
|---|---|---|---|---|---|---|
| | TETRA SIGM1LLLSSL 2 | TETRA SIGM1LLLSSL 2 | Soil 1 from Corn field with antibiotic, MA | YDM-TM | RT | Yes | N/A | 8/3/2007 |
| | TETRA SIGM1LLLSSL 3 | TETRA SIGM1LLLSSL 3 | Soil 1 from Corn field with antibiotic, MA | YDM-TM | RT | Yes | N/A | 8/3/2007 |
| | OXYTET SIGM1LLLSSL 1 | OXYTET SIGM1LLLSSL 1 | Soil 1 from Corn field with antibiotic, MA | YDM-TM | RT | Yes | N/A | 8/3/2007 |
| | OXYTET SIGM1LLLSSL 2 | OXYTET SIGM1LLLSSL 2 | Soil 1 from Corn field with antibiotic, MA | YDM-TM | RT | Yes | N/A | 8/3/2007 |
| | OXYTET SIGM1LLLSSL 3 | OXYTET SIGM1LLLSSL 3 | Soil 1 from Corn field with antibiotic, MA | YDM-TM | RT | Yes | N/A | 8/3/2007 |
| | MINO SIGM1LLLSSL 1 | MINO SIGM1LLLSSL 1 | Soil 1 from Corn field with antibiotic, MA | YDM-TM | RT | Yes | N/A | 8/3/2007 |
| | MINO SIGM1LLLSSL 2 | MINO SIGM1LLLSSL 2 | Soil 1 from Corn field with antibiotic, MA | YDM-TM | RT | Yes | N/A | 8/3/2007 |
| | MINO SIGM1LLLSSL 3 | MINO SIGM1LLLSSL 3 | Soil 1 from Corn field with antibiotic, MA | YDM-TM | RT | Yes | N/A | 8/3/2007 |
| | D-CYCLO SIGM1LLLSSL 1 | D-CYCLO SIGM1LLLSSL 1 | Soil 1 from Corn field with antibiotic, MA | YDM-TM | RT | Yes | N/A | 8/3/2007 |
| | D-CYCLO SIGM1LLLSSL 2 | D-CYCLO SIGM1LLLSSL 2 | Soil 1 from Corn field with antibiotic, MA | YDM-TM | RT | Yes | N/A | 8/3/2007 |
| | D-CYCLO SIGM1LLLSSL 3 | D-CYCLO SIGM1LLLSSL 3 | Soil 1 from Corn field with antibiotic, MA | YDM-TM | RT | Yes | N/A | 8/3/2007 |
| | VANCO SIGM1LLLSSL 1 | VANCO SIGM1LLLSSL 1 | Soil 1 from Corn field with antibiotic, MA | YDM-TM | RT | Yes | N/A | 8/3/2007 |
| | VANCO SIGM1LLLSSL 2 | VANCO SIGM1LLLSSL 2 | Soil 1 from Corn field with antibiotic, MA | YDM-TM | RT | Yes | N/A | 8/3/2007 |
| | VANCO SIGM1LLLSSL 3 | VANCO SIGM1LLLSSL 3 | Soil 1 from Corn field with antibiotic, MA | YDM-TM | RT | Yes | N/A | 8/3/2007 |

TOXIN-EATING BACTERIA AND BIOREMEDIATION

PRIORITY INFORMATION

This application claims priority to U.S. Provisional Patent Application No. 61/105,614, filed on Oct. 15, 2008 and is hereby incorporated herein by reference in its entirety for all purposes.

STATEMENT OF GOVERNMENT INTERESTS

This application was made with Government support under DE-FG02-03ER63445 (T-103693) awarded by the U.S. Department of Energy. The Government has certain rights in the invention.

BACKGROUND

The seemingly unchecked spread of multiple antibiotic resistance in clinically relevant pathogenic microbes is alarming. Furthermore, a significant environmental reservoir of antibiotic resistance determinants, termed the antibiotic resistome, has been discovered (Riesenfeld et al. (2004) *Environmental Microbiology* 6:981; D'Costa et al. (2006) *Science* 311:374). The primary microbial antibiotic resistance mechanisms include efflux pumps, target gene-product modifications, and enzymatic inactivation of the antibiotic compound (Walsh (2000) *Nature* 406:775; Alekshun and Levy (2007) *Cell* 128:1037). Many of the mechanisms are common to several species of pathogens and spread by lateral gene transfer (Davies (1994) *Science* 264:375). While many bacteria growing in extreme environments (Davies (1994) *Science* 264:375) and capable of degrading toxic substrates (McAllister et al. (1996) *Biodegradation* 7:1) have been previously reported, only a few organisms have been shown to subsist on a limited number of antibiotic substrates (Kameda et al. (1961) *Nature* 191:1122; Johnsen (1977) *Archives of Microbiology* 115:271; Abdelm et al. (1961) *Nature* 189:775).

SUMMARY

The present invention is based in part on the surprising discovery that the microbiome (e.g., of soil and/or water) includes a significant reservoir of bacteria capable of subsisting on antibiotics. Clonal bacterial isolates were obtained from eleven diverse soils which were capable of utilizing one of 18 different antibiotics as the sole carbon source. The 18 antibiotics comprised of natural, semi-synthetic and synthetic compounds and included all major bacterial target classes.

Accordingly, in certain exemplary embodiments, a method of reducing a level of one or more antibiotics from an antibiotic-contaminated substance comprising culturing an organism that can utilize the one or more antibiotics as a carbon source (e.g., a sole carbon source) in the presence of the antibiotic-contaminated substance for a sufficient amount of time to reduce the level of one or more antibiotics from the antibiotic-contaminated substance is provided. In certain aspects, the organism is a bacterium. In other aspects, one or more antibiotics are from the antibiotic class including one or more of pyrimidine derivative, sulfonamide, quinolone, glycopeptides, beta-lactam, amphenicols, aminoglycoside and amino acid derivative. In yet other aspects, one or more antibiotics are selected from the group including one or more of chloramphenicol, penicillin G, vancomycin, carbenicillin, ciprofloxacin, mafenide, kanamycin, sisomicin, amikacin, trimethropin, D-cycloserine, gentamicin, dicloxacillin, nalidixic acid, thiamphenicol, levofloxacin, sulfamethizole and sulfisoxazole. In still other aspects, the antibiotic-contaminated substance is one or more of contaminated soil, contaminated water and a contaminated work surface (e.g., in a hospital, a clinic, a laboratory or the like).

In certain exemplary embodiments, a bacterium that can use one or more antibiotics as a carbon source (e.g., a sole carbon source) is provided. The bacterium has a 16S nucleic acid sequence comprising a GenBank Accession Number selected from one or more of EU515334, EU515335, EU515336, EU515337, EU515338, EU515339, EU515400, EU515401, EU515402, EU515403, EU515404, EU515405, EU515406, EU515407, EU515408, EU515409, EU515410, EU515411, EU515412, EU515413, EU515414, EU515415, EU515416, EU515417, EU515418, EU515419, EU515420, EU515421, EU515422, EU515423, EU515424, EU515425, EU515426, EU515427, EU515428, EU515429, EU515430, EU515431, EU515432, EU515433, EU515434, EU515435, EU515436, EU515437, EU515438, EU515439, EU515440, EU515441, EU515442, EU515443, EU515444, EU515445, EU515446, EU515447, EU515448, EU515449, EU515450, EU515451, EU515452, EU515453, EU515454, EU515455, EU515456, EU515457, EU515458, EU515459, EU515460, EU515461, EU515462, EU515463, EU515464, EU515465, EU515466, EU515467, EU515468, EU515469 EU515470, EU515471, EU515472, EU515473, EU515474, EU515475, EU515476, EU515477, EU515478, EU515479, EU515480, EU515481, EU515482, EU515483, EU515484, EU515485, EU515486, EU515487, EU515488, EU515489, EU515490, EU515491, EU515492, EU515493, EU515494, EU515495, EU515496, EU515497, EU515498, EU515499, EU515500, EU515501, EU515502, EU515503, EU515504, EU515505, EU515506, EU515507, EU515508, EU515509, EU515510, EU515511, EU515512, EU515513, EU515514, EU515515, EU515516, EU515517, EU515518, EU515519, EU515520, EU515521, EU515522, EU515523, EU515524, EU515525, EU515526, EU515527, EU515528, EU515529, EU515530, EU515531, EU515532, EU515533, EU515534, EU515535, EU515536, EU515537, EU515538, EU515539, EU515540, EU515541, EU515542, EU515543, EU515544, EU515545, EU515546, EU515547, EU515548, EU515549, EU515550, EU515551, EU515552, EU515553, EU515554, EU515555, EU515556, EU515557, EU515558, EU515559, EU515560, EU515561, EU515562, EU515563, EU515564, EU515565, EU515566, EU515567, EU515568, EU515569, EU515570, EU515571, EU515572, EU515573, EU515574, EU515575, EU515576, EU515577, EU515578, EU515579, EU515580, EU515581, EU515582, EU515583, EU515584, EU515585, EU515586, EU515587, EU515588, EU515589, EU515590, EU515591, EU515592, EU515593, EU515594, EU515595, EU515596, EU515597, EU515598, EU515599, EU515600, EU515601, EU515602, EU515603, EU515604, EU515605, EU515606, EU515607, EU515608, EU515609, EU515610, EU515611, EU515612, EU515613, EU515614, EU515615, EU515616, EU515617, EU515618, EU515619, EU515620, EU515621, EU515622 and EU515623. In certain aspects, one or more antibiotics are from the antibiotic class including one or more of pyrimidine derivative, sulfonamide, quinolone, glycopeptides, beta-lactam, amphenicols, aminoglycoside and amino acid derivative. In other aspects, one or more antibiotics include one or more of chloramphenicol, penicillin G, vancomycin, carbenicillin, ciprofloxacin, mafenide, kanamycin, sisomicin, amikacin, trimethropin, D-cycloserine, gentamicin, dicloxacillin, nalidixic acid, thiamphenicol, levofloxacin, sulfamethizole and sulfisoxazole.

In certain exemplary embodiments, a method of removing one or more antibiotics from an antibiotic-contaminated substance, comprising culturing a bacterium described above in the presence of the antibiotic-contaminated substance for a sufficient amount of time to reduce the level of one or more antibiotics from the antibiotic-contaminated substance is provided. In certain aspects, one or more antibiotics are from the antibiotic class including one or more of pyrimidine derivative, sulfonamide, quinolone, glycopeptides, beta-lactam, amphenicols, aminoglycoside and amino acid derivative. In other aspects, one or more antibiotics are selected from the group including one or more of chloramphenicol, penicillin G, vancomycin, carbenicillin, ciprofloxacin, mafenide, kanamycin, sisomicin, amikacin, trimethropin, D-cycloserine, gentamicin, dicloxacillin, nalidixic acid, thiamphenicol, levofloxacin, sulfamethizole and sulfisoxazole. In yet other aspects, the antibiotic-contaminated substance is one or more of contaminated soil, contaminated water and a contaminated work surface (e.g., in a hospital, a clinic, a laboratory or the like.

Further features and advantages of certain embodiments of the present invention will become more fully apparent in the following description of the embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

FIG. 7 depicts a list of antibiotic catabolizing isolates described in FIG. 2. AIB2: Antibiotic Box 2; S*: section; YDM-TM: 1×YDM, trace metals, pH 5.5; Extr: extraction; RT: room temperature.

FIG. 8 depicts a list of antibiotic catabolizing isolates described in FIG. 2. AIB3: Antibiotic Box 3; S*: section; YDM-TM: 1×YDM, trace metals, pH 5.5; Extr: extraction; RT: room temperature.

FIG. 9 depicts a list of antibiotic catabolizing isolates described in FIG. 2. AIB4: Antibiotic Box 4; S*: section; YDM-TM: 1×YDM, trace metals, pH 5.5; Extr: extraction; RT: room temperature.

FIG. 10 depicts a list of antibiotic catabolizing isolates described in FIG. 2. AIB5: Antibiotic Box 5; S*: section; YDM-TM: 1×YDM, trace metals, pH 5.5; Extr: extraction; RT: room temperature.

FIG. 11 depicts a list of antibiotic catabolizing isolates described in FIG. 2. AIB6: Antibiotic Box 6; S*: section; YDM-TM: 1×YDM, trace metals, pH 5.5; Extr: extraction; RT: room temperature.

FIG. 12 depicts a list of antibiotic catabolizing isolates described in FIG. 2. AIB7: Antibiotic Box 7; S*: section; YDM-TM: 1×YDM, trace metals, pH 5.5; Extr: extraction; RT: room temperature.

FIG. 13 depicts a list of antibiotic catabolizing isolates described in FIG. 2. AIB8: Antibiotic Box 8; S*: section; YDM-TM: 1×YDM, trace metals, pH 5.5; Extr: extraction; RT: room temperature.

DETAILED DESCRIPTION

Figure 1:
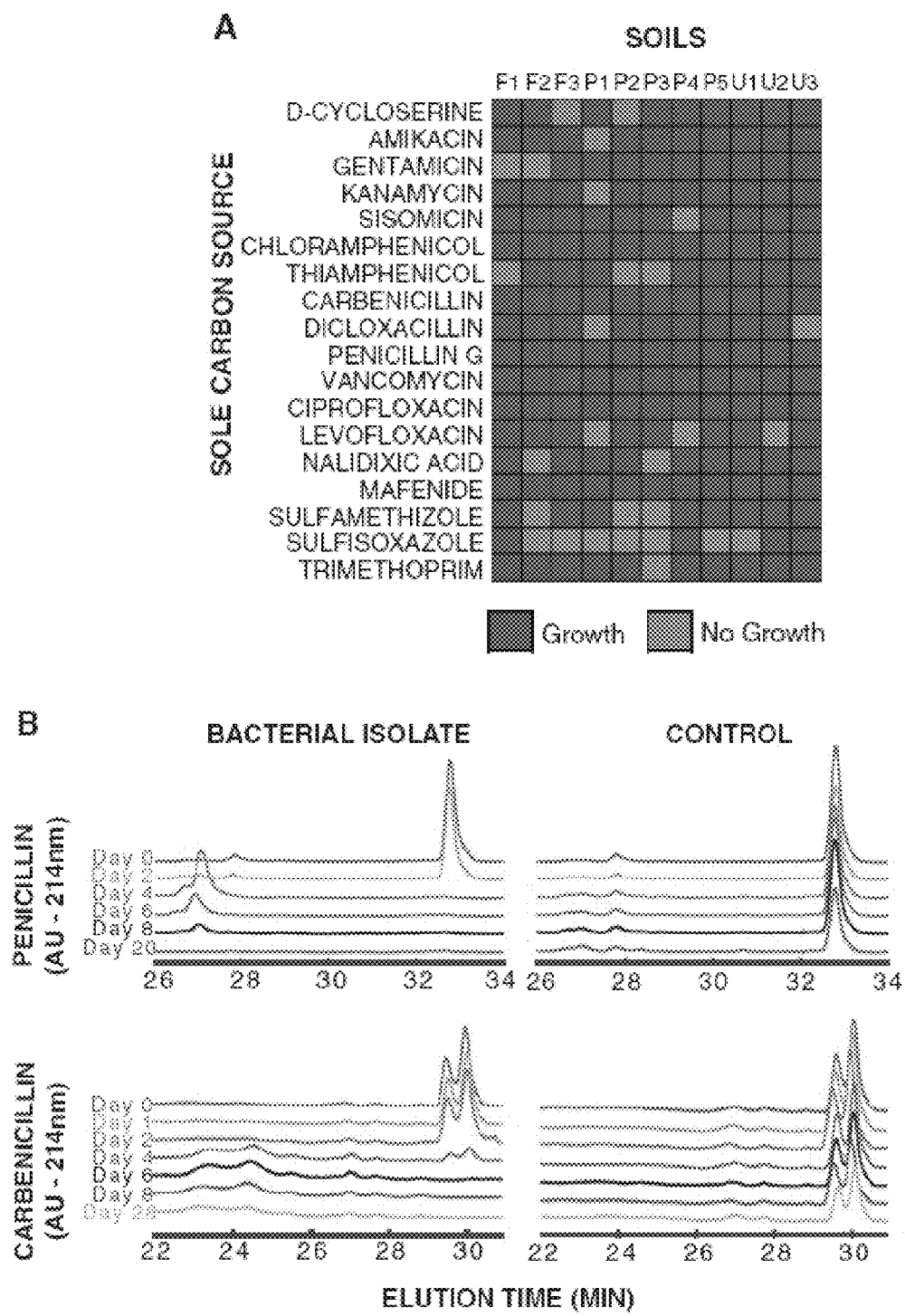
FIGS. 1A-1B graphically depict clonal bacterial isolates subsisting on antibiotics. (A) Heat-map illustrating growth results from all combinations of 11 soils by 18 antibiotics, where blue squares represent successful isolation of bacteria from a given soil that are able to utilize that antibiotic as sole carbon source at 1 g/L. Soil samples labeled F1-3 were from farm soils and U1-3 were from urban soils. Soil samples P1-5 were from pristine soils, collected from non-urban areas with minimal human exposure over the last 100 years (Table 2). (B) High performance liquid chromatography (HPLC) traces at 214 nm of representative penicillin and carbenicillin catabolizing clonal isolates and corresponding un-inoculated media controls for different time points over 20 or 28 days of growth, respectively.

Man-made chemicals are often used to clean up contaminated and/or toxic materials, which can be both costly and time-consuming. Microorganisms (e.g., bacteria) are a natural, inexpensive means for reducing and/or eliminating contamination and/or toxicity of a substance. Accordingly, in certain exemplary embodiments, antibiotic and/or toxin eating microorganisms (e.g., bacteria) that can be produced using the methods described herein are provided. In certain aspects, a cell, cell lysate, cell extract, cell fraction, protein(s), polypeptide(s), isolated antibiotic(s) or any combinations thereof from one or more antibiotic and/or toxin eating microorganisms (e.g., bacteria) are incubated in the presence of a contaminated substance to reduce or eliminate contamination. In another aspect, antibiotic and/or toxin eating bacteria are used in hybrid biological/chemical manufacturing or decontamination systems where resistance to high levels of various chemicals is helpful in the process engineering. A cell, cell lysate, cell extract, cell fraction, protein(s), polypeptide(s), isolated antibiotic(s) or any combinations thereof from one or more antibiotic and/or toxin eating microorganisms (e.g., bacteria) can be applied to a contaminated substance or a manufacturing system via aerosols, slurries, cleaning solutions, animal feeds, seeds, fertilizer and the like to partially or completely decontaminate the substance or manufacturing system.

As used herein, the terms "toxin-eating bacterium" and "toxin-eating bacteria" refer to bacteria that can use one or more toxins and/or contaminants as a carbon source(s) or as the sole carbon source to support growth. As used herein, the terms "antibiotic-eating bacterium" and "antibiotic-eating bacteria" refer to bacteria that can use one or more antibiotics as a carbon source(s) or as the sole carbon source to support growth.

In certain exemplary embodiments, one or more toxin-eating bacteria described herein are used for bioremediation of one or more contaminants from a variety of environments such as, e.g., earth (e.g., sand, soil, rocks, any combination thereof and the like), water (e.g., springs, lakes, brooks, streams, rivers, bays, estuaries, seas, oceans and the like), air, manmade surfaces (e.g., medical facilities, instruments, service salons, makeup counters etc.) and the like. As used herein, the term "bioremediation" refers to the ability of one or more bacteria described herein to remove or reduce the levels of one or more contaminants from an environment.

As used herein, the terms "toxic environment" and "contaminated substance" refer to an environment or substance, respectively, that contains one or more adverse compound(s) and/or physical condition(s) that can inhibit growth, inhibit productivity and/or lead to the death of one or more microorganisms exposed to the compound(s) and/or physical condition(s). A toxic environment includes, but is not limited to, the following: the presence of inhibitory compounds (e.g., antibiotics, radioactive compounds, heavy metals and the like) high or low salinity, extreme temperatures (e.g., high temperature (e.g., in thermal vents) and/or cold temperature (e.g., in icy conditions), water scarcity, darkness, light, catalytic products (e.g., cell waste, alcohol and the like) and the like. For example, a toxic environment can include the presence of a concentration (e.g., high or low concentrations) of a compound and/or a condition that is considered non-toxic to the microorganism in typical concentrations and/or in typical conditions, as well as the presence of a compound or a physical condition that would be typically considered to be detrimental to the organism.

In certain embodiments, the toxicity (of a toxic environment) or contamination (of a contaminated substance) is eliminated or reduced to non-toxic or non-contaminated levels. In certain aspects, the toxicity and/or contamination is reduced by about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.9% or more.

In certain exemplary embodiments, DNA fragments that can be used in a microorganism to decrease toxicity and/or contamination of a substance are provided. In certain aspects, the identification of useful DNA fragments occurs by introducing a diverse library of DNA fragments into a clonal population of the production microorganism creating a population of cells harboring different DNA fragments. The population of microorganisms harboring the large DNA fragment library is subjected to growth in the presence of high concentration of the inhibitor(s) which would normally suppress growth of the host organism. If a host cell in the population contains a DNA fragment which encodes for resistance to, e.g., high concentrations of inhibitor(s) (e.g., one or more antibiotics), the cell will selectively grow and can be identified. The DNA fragment that enabled the cell to tolerate the inhibitor can then be isolated, characterized and subsequently introduced into the production microorganism improving its catalytic productivity in the presence of the inhibitor.

As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *D. rerio*) a roundworm (e.g., *C. elegans*) and any transgenic species thereof. The term "organism" further includes, but is not limited to, a yeast (e.g., *S. cerevisiae*) cell, a yeast tetrad, a yeast colony, a bacterium, a bacterial colony, a virion, virosome, virus-like particle and/or cultures thereof, and the like.

As used herein, the terms "microorganism" and "microbe" refer to tiny organisms. Most microorganisms and microbes are unicellular, although some multicellular organisms are microscopic, while some unicellular protists and bacteria (e.g., *T. namibiensis*) called are visible to the naked eye. Microorganisms and microbes include, but are not limited to, bacteria, fungi, archaea and protists, microscopic plants, and animals (e.g., plankton, the planarian, the amoeba) and the like.

Certain aspects of the invention pertain to vectors, such as, for example, expression vectors, containing a nucleic acid encoding one or more bipolar cell-specific regulatory sequences. As used herein, the term "vector" refers to a nucleic acid sequence capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. By way of example, but not of limitation, a vector of the invention can be a single-copy or multi-copy vector, including, but not limited to, a BAC (bacterial artificial chromosome), a fosmid, a cosmid, a plasmid, a suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of interest (e.g., a nucleic acid sequence from a microorganism) in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is present in the vector in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences).

It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or portions thereof, including fusion proteins or portions thereof, encoded by nucleic acids as described herein.

In certain exemplary embodiments, a nucleic acid described herein is expressed in bacterial cells using a bacterial expression vector such as, e.g., a fosmid. A fosmid is a cloning vector that is based on the bacterial F-plasmid. The host bacteria will typically only contain one fosmid molecule, although an inducible high-copy on can be included such that a higher copy number can be obtained (e.g., pCC1FOS™, pCC2FOS™) Fosmid libraries are particularly useful for constructing stable libraries from complex genomes. Fosmids and fosmid library production kits are commercially available (EPICENTRE® Biotechnologies, Madison, Wis.). For other suitable expression systems for both prokaryotic and eukaryotic cells see chapters 16 and 17 of Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, one or more bipolar cell-specific regulatory elements and/or portion(s) thereof can be reproduced in bacterial cells such as *E. coli*, viruses such as retroviruses, insect cells, yeast or mammalian cells (such as Chinese hamster ovary cells (CHO) or COS cells). Other suitable host cells are known to those skilled in the art.

Delivery of nucleic acid sequences described herein (e.g., vector DNA) can be by any suitable method in the art. For example, delivery may be by injection, gene gun, by application of the nucleic acid in a gel, oil, or cream, by electroporation, using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual*. 2nd, ed., Cold Spring harbor Laboratory, Cold Spring Harbor Laboratory Press, Cold Spring Harbor, N.Y., 1989), and other laboratory manuals.

In certain exemplary embodiments, one or more host microorganisms described herein are engineered with various isolation and/or safety features such as, e.g., novel genetic codes, broad restriction systems, extreme sensitivity to substances common in nature (e.g., UV light), dependency on lab metabolites uncommon in nature (e.g., diaminopimelic acid) and the like in order to decrease the spread of antibiotic and/or toxin resistance gene(s) from one or more host cells. A non-limiting example of a broad restriction system would be expression in the same cell endonucleases aimed at both the methylated and unmethylated forms of a DNA sequence (e.g., DpnI and DpnII aimed at G-mA-T-C and GATC). This would require the removal of all sites (GATC in the above example) throughout the host genome.

In certain exemplary embodiments, antibiotic and/or toxin eating microorganisms (e.g., bacteria) are used to develop novel antibiotics. Novel antibiotics are useful for overcoming the multi-drug resistance (MDR) that is increasingly observed among pathogenic bacteria. In certain exemplary aspects, antibiotic and/or toxin eating bacteria are used to manufacture novel antibiotics either harvested metagenomically from diverse natural microbial cells or engineered from combinatorial libraries. Even the trace amounts need to detect biosynthesis of novel compounds could be enough to kill the host (or put undesired pressure to be unproductive).

Novel antibiotics can be manufactured, for example, by metagenomic harvesting from natural microbial cells or by engineering from combinatorial libraries. In certain exemplary embodiments, one or more microorganisms that are resistant to one or more compounds that typically kill and/or inhibit the growth of the microorganism (e.g., antibiotics, toxins and the like) are used in screening assays for identifying modulators, i.e., candidate or test compounds or agents (e.g., antibodies, peptides, cyclic peptides, peptidomimetics, small molecules, small organic molecules, antibiotics or drugs) which kill or have an inhibitory effect on the growth of one or more microorganisms are provided. In certain aspects, such screening assays can identify novel antibiotics as well as antibiotics that are effective in killing or reducing the growth of one or more multiple antibiotic resistant microorganisms.

As used herein, the term "antibiotic" refers to a chemotherapeutic agent (e.g., an agent produced by microorganisms and/or synthetically) that has the capacity to inhibit the growth of and/or to kill, one or more microorganisms (e.g., bacteria, fungi, parasites and the like) or aberrantly growing cells (e.g., tumor cells). As used herein, antibiotics are well-known to those of skill in the art. Classes of antibiotics include, but are not limited to, aminoglycosides (e.g., amikacin, gentamicin, kanamycin, neomycin, netilmicin, streptomycin, tobramycin, paromomycin and the like), ansamycins (e.g., geldanamycin, herbimycin and the like), carbacephem (e.g., loracarbef), carbapenems (e.g., ertapenem, doripenem, imipenem/cilastatin, meropenem and the like) cephalosporins (e.g., first generation (e.g., cefadroxil, cefazolin, cefalotin, cefalexin and the like), second generation (e.g., cefaclor, cefamandole, cefoxitin, cefprozil, cefuroxime and the like), third generation (e.g., cefixime, cefdinir, cefditoren, cefoperazone, cefotaxime, cefpodoxime, ceftazidime, ceftibuten, ceftizoxime, ceftriaxone and the like), fourth generation (e.g., cefepime and the like) and fifth generation (e.g., ceftobiprole and the like)), glycopeptides (e.g., teicoplanin, vancomycin and the like), macrolides (e.g., azithromycin, clarithromycin, dirithromycin, erythromycin, roxithromycin, troleandomycin, telithromycin, spectinomycin and the like), monobatams (e.g., aztreonam and the like), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticacillin and the like), polypeptides (e.g., bacitracin, colistin, polymyxin B and the like) quinolones (e.g., ciprofloxacin, enoxacin, gatifloxacin, levofloxacin, lomefloxacin, moxifloxacin, norfloxacin, ofloxacin, trovafloxacin and the like), sulfonamides (e.g., mafenide, prontosil, sulfacetamide, sulfamethizole, sulfanilamide, sulfasalazine, sulfisoxazole, trimethoprim, trimethoprim-sulfamethoxazole and the like), tetracyclines (e.g., demeclocycline, doxycycline, minocycline, oxytetracycline, tetracycline and the like) and others (e.g., arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin, tinidazol and the like) (See, e.g., Robert Berkow (ed.) *The Merck Manual of Medical Information—Home Edition*. Pocket (September 1999), ISBN 0-671-02727-1).

In certain exemplary embodiments, assays for screening candidate or test compounds (e.g., antibiotics) which bind to or modulate (e.g., kill or have an inhibitory effect on the growth of) a microorganism are provided. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

The candidate or test compound(s) described herein can be incorporated into pharmaceutical compositions suitable for administration. Such compositions typically comprise the nucleic acid molecule or protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In certain exemplary embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the candidate or test compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, the candidate or test compound(s) are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The candidate or test compound(s) can also be prepared in the form of suppositories (e.g., with conventional suppository bases such as cocoa butter and other glycerides) or retention enemas for rectal delivery.

In one embodiment, candidate or test compound(s) are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of candidate or test compound(s) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In certain exemplary embodiments, a method for treatment of infection by a microorganism includes the step of administering a therapeutically effective amount of an agent (e.g., one or more candidate or test compounds) which modulates (e.g., kills and/or inhibits the growth of), one or more microorganisms to a subject. As defined herein, a therapeutically effective amount of agent (i.e., an effective dosage) ranges from about 0.001 to 30 mg/kg body weight, from about 0.01 to 25 mg/kg body weight, from about 0.1 to 20 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, in certain exemplary embodiments, can include a series of treatments. It will also be appreciated that the effective dosage of inhibitor used for treatment may increase or decrease over the course of a particular treatment. Changes in dosage may result from the results of diagnostic assays as described herein. The pharmaceutical compositions can be included in a container, pack, or dispenser together with instructions for administration.

In certain embodiments, monitoring the influence of agents (e.g., drugs, compounds) on the killing and/or inhibiting cell growth of one or more microorganisms can be applied not only in basic drug screening, but also in clinical trials. In certain exemplary embodiments, a method is provided for monitoring the effectiveness of treatment of a subject with an agent (e.g., an agonist, antagonist, antibody, peptidomimetic, protein, peptide, nucleic acid, small molecule, antibiotic or other drug candidate identified by the screening assays described herein) comprising the steps of (i) obtaining a pre-administration sample from a subject prior to administration of the agent; (ii) detecting the level of a microorganism in the preadministration sample; (iii) obtaining one or more post-administration samples from the subject; (iv) detecting the level the microorganism in the post-administration samples; (v) comparing the level of microorganism in the pre-administration sample with the level of microorganism in the post-administration sample or samples; and (vi) altering the administration of the agent to the subject accordingly. For example, increased administration of the agent may be desirable to increase the effectiveness of the agent. Alternatively, decreased administration of the agent may be desirable to decrease the effectiveness of the agent.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, tables, figures, and accompanying claims.

EXAMPLE I

Bacteria Subsisting on Antibiotics

Antibiotics are a crucial line of defense against bacterial infections. Nevertheless, several antibiotics are natural products of microorganisms that have as yet poorly appreciated ecological roles in the wider environment. Hundreds of soil bacteria with the capacity to grow on antibiotics as a sole carbon source were isolated. Of 18 antibiotics tested, representing eight major classes of natural and synthetic origin, 13-17 antibiotics supported growth of clonal bacteria from each of 11 diverse soils. Bacteria subsisting on antibiotics are surprisingly phylogenetically diverse and many are closely related to human pathogens. Furthermore, each antibiotic consuming isolate is resistant to multiple antibiotics at clinically relevant concentrations. This phenomenon suggests this unappreciated reservoir of antibiotic resistance determinants can contribute to the increasing levels of multiple antibiotic resistance in pathogenic bacteria.

Figure 4:
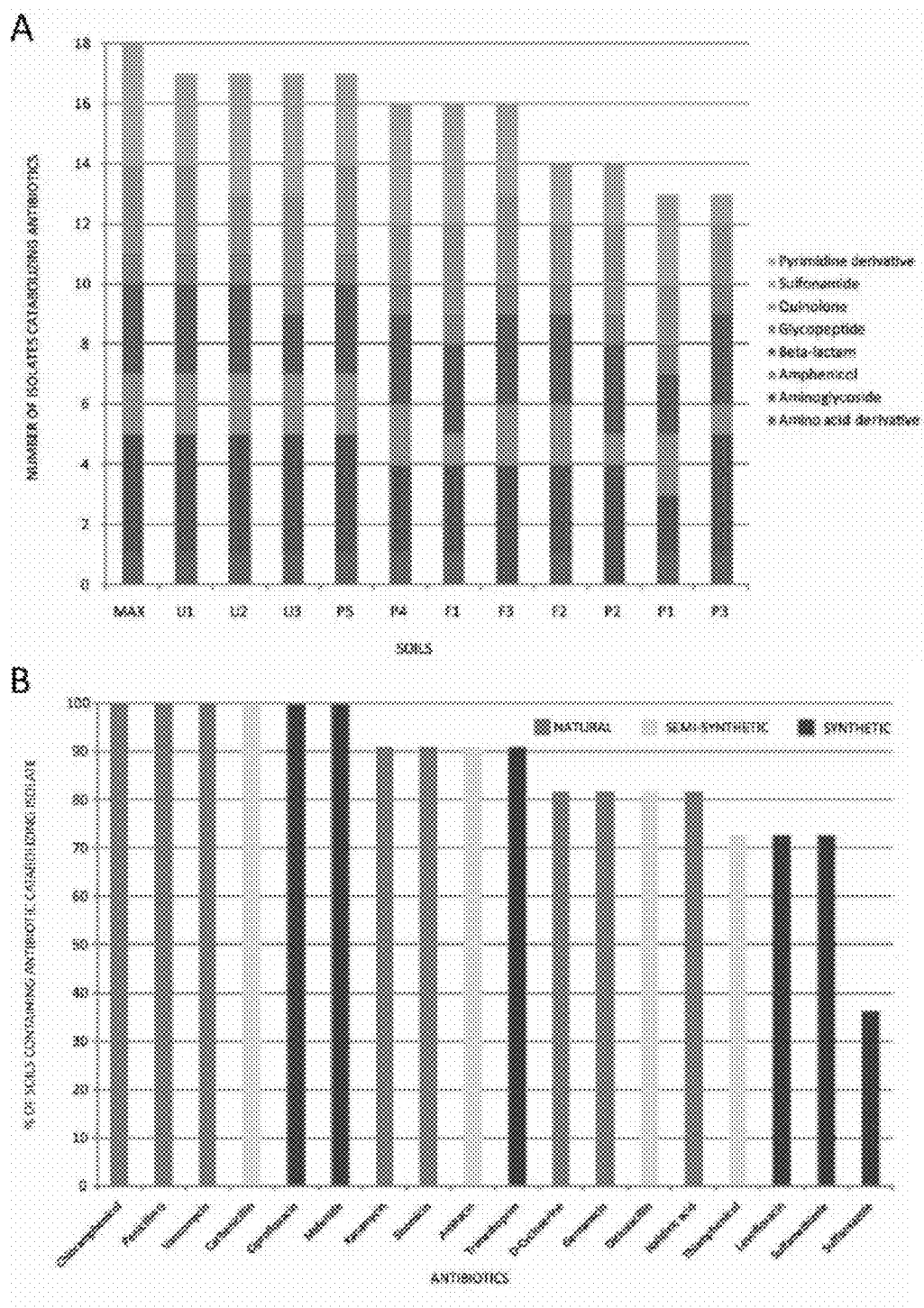
FIGS. 4A-4B graphically depict the distribution of antibiotic catabolizing bacterial isolates with respect to antibiotics and soil. (A) Number of antibiotic catabolizing bacteria isolated from 11 soils color-coded by antibiotic class catabolized. (B) Percentage of soils containing antibiotic catabolizing bacteria, color-coded by chemical origin of antibiotic.
Figure 5:
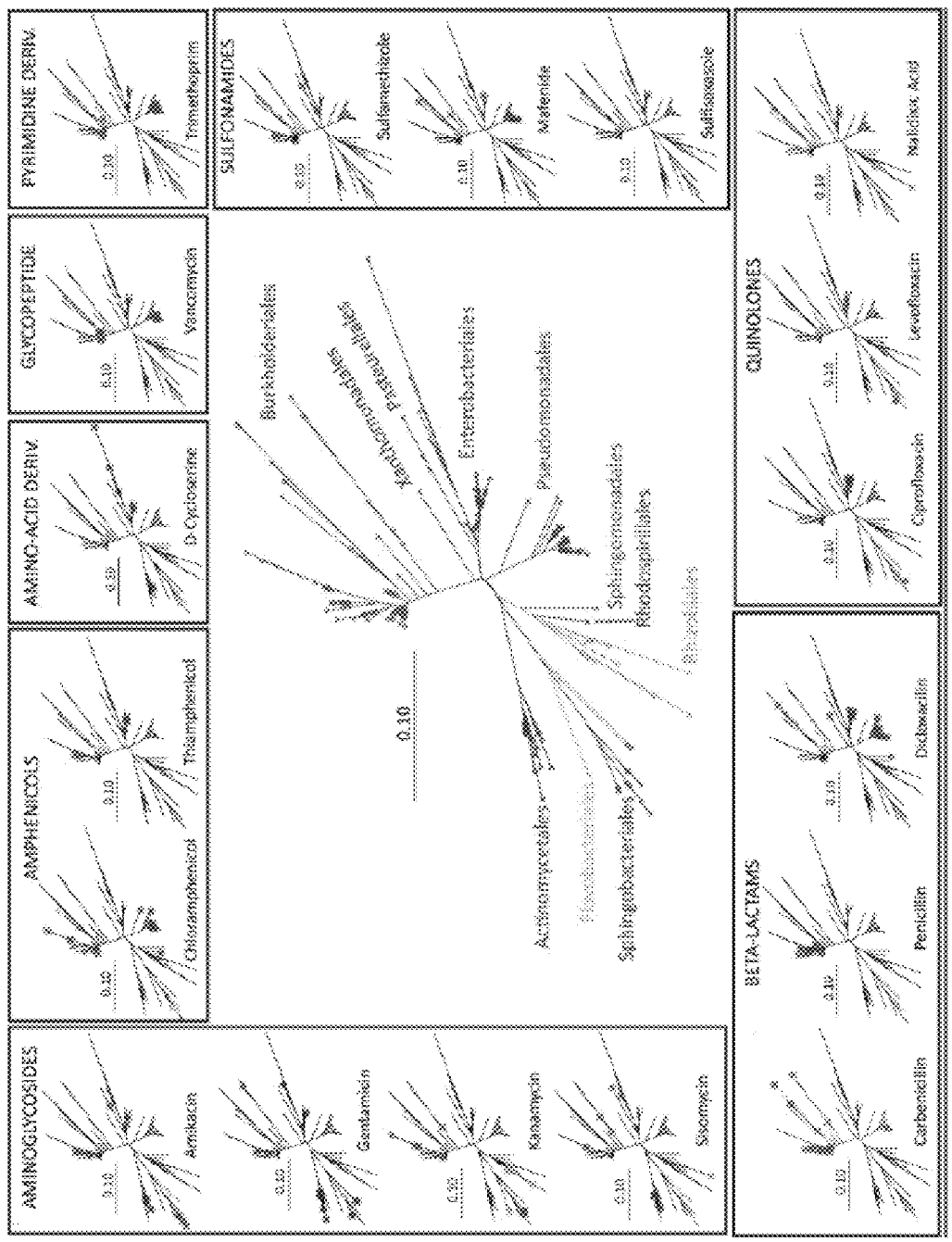
FIG. 5 schematically depicts the phylogenetic distribution of bacterial isolates subsisting on antibiotics. Full set of bacteria subsisting on antibiotics is displayed in the centre, with branches color-coded by bacterial orders, and clonal isolates represented as squares. Subsets comprising clonal isolates catabolizing each antibiotic are represented as trees around the periphery, grouped by antibiotic class. 16S ribosomal DNA (rDNA) was sequenced from antibiotic catabolizing clonal isolates using universal bacterial rDNA primers. High-quality, non-chimeric sequences were classified using Greengenes (DeSantis et al. (2006) *Applied and Environmental Microbiology* 72:5069), with consensus annotations from RDP (Cole et al. (2007) *Nucleic Acids Res* 35:D169) and NCBI taxonomies (Wheeler et al. (2000) *Nucleic Acids Res* 28:10). Phylogenetic trees were constructed using the neighbor joining algorithm in ARB (Ludwig et al. (2004) *Nucleic Acids Res* 32:1363) using the Greengenes aligned 16S rDNA database. Placement in the tree was confirmed by comparing automated Greengenes taxonomy to the annotated taxonomies of nearest neighbors of each sequence in the aligned database. The phylogenetic distributions of species isolated from different antibiotics as sole carbon source exhibit some interesting trends. For instance, the fluoroquinolone antibiotics, ciprofloxacin and levofloxacin, have similar phylogenetic distributions, as do the aminoglycoside antibiotics, gentamycin and amikacin, but the two sets are notably different from each other. Interestingly, the orders of bacteria subsisting on amikacin appear more similar to gentamycin than kanamycin despite amikacin being a semi synthetic kanamycin derivative.

Clonal bacterial isolates from 11 diverse soils (Table 2) which were capable of utilizing one of 18 different antibiotics as the sole carbon source were cultured. The 18 antibiotics comprised of natural, semi-synthetic and synthetic compounds of different ages and included all major bacterial target classes. Every antibiotic tested was able to support bacterial growth (FIG. 1A and FIGS. 4A-4B). Notably, 6 out of 18 antibiotics supported growth in all 11 soils, covering 5 of the 8 classes of antibiotics tested. Appropriate controls were performed to ensure that carbon source contamination of the source media or carbon fixation from the air were insignificant to this experiment (See Example II).

Clonal isolates capable of subsisting on penicillin and carbenicillin were obtained from all the soils tested, and isolates from 9 out of 11 soils that could subsist on dicloxacillin. Representative isolates capable of growth on penicillin and carbenicillin were selected for subsequent analysis by high performance liquid chromatography (HPLC) (See Example II). Removal of the antibiotics from the media was observed within 4 and 6 days, respectively (FIG. 1B). Mass spectrometry analysis of penicillin cultures is consistent with a penicillin catabolic pathway (Johnsen (1977) *Archives of Microbiology* 115:271) initiated by hydrolytic cleavage of the beta lactam ring, which is the dominant mode of clinical resistance to penicillin and related beta lactam antibiotics, followed by a decarboxylation step (FIGS. 6A-6C) (See Example II).

Bacteria were isolated from all the soils tested that grew on ciprofloxacin (FIG. 1A), a synthetic fluoroquinolone and one of the most widely prescribed antibiotics. Clonal isolates capable of catabolizing the other two synthetic quinolones tested, levofloxacin and nalidixic acid, were also isolated from a majority of the soils (FIG. 1A). Previous studies have highlighted the strong parallels between antibiotic resistance determinants harbored by soil dwelling microbes and human pathogens (Davies (1994) *Science* 264:375; Marshall (1998) *Antimicrobial Agents and Chemotherapy* 42:2215; D'Costa et al. (2007) *Curr. Opin. Microbiol.* 10:481). The lateral transfer of genes encoding the enzymatic machinery responsible for subsistence on quinolone antibiotics to human pathogens could introduce a novel resistance mechanism so far not observed in the clinic.

Figure 2:
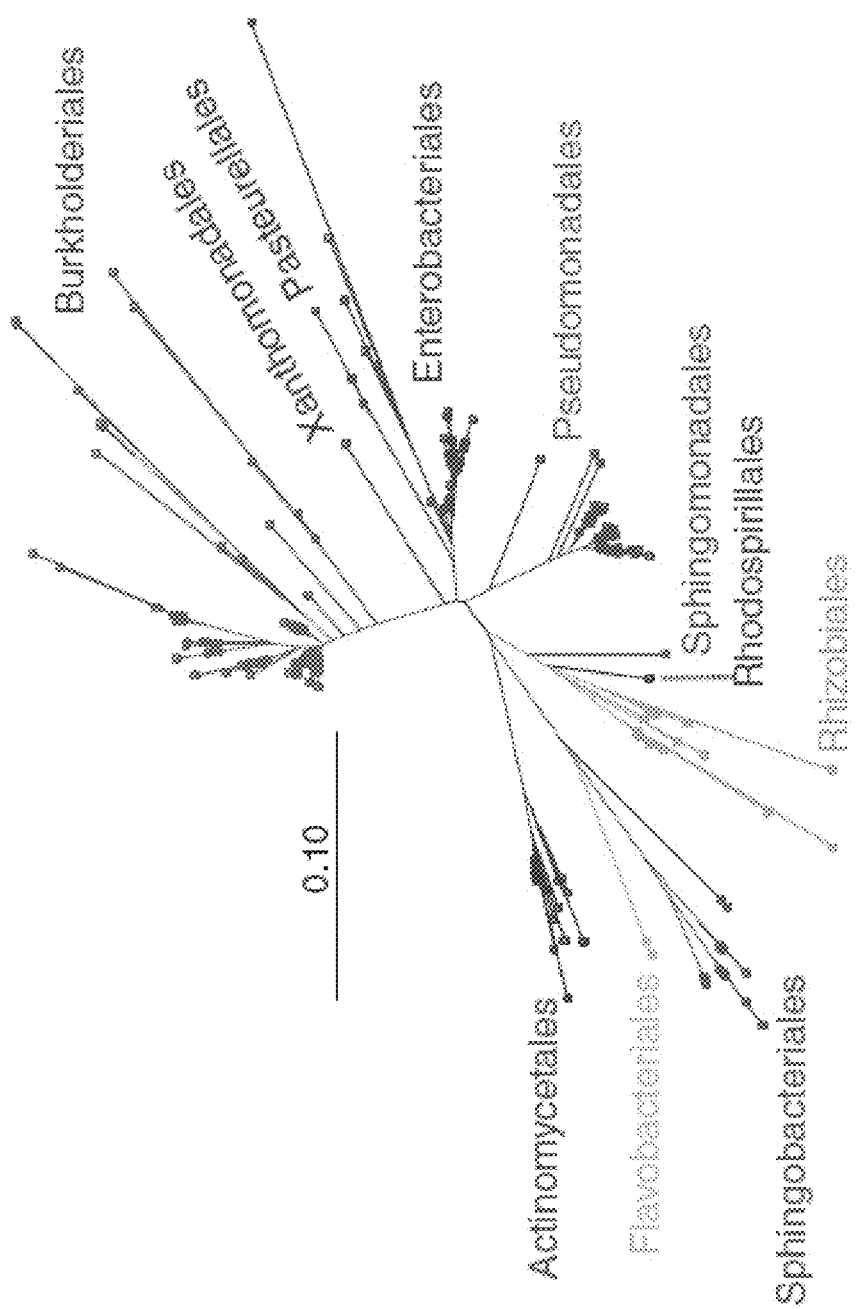
FIG. 2 graphically depicts the phylogenetic distribution of bacterial isolates subsisting on antibiotics. 16S ribosomal DNA (rDNA) was sequenced from antibiotic catabolizing clonal isolates using universal bacterial rDNA primers. High-quality, non-chimeric sequences were classified using Greengenes (DeSantis et al. (2006) *Applied and Environmental Microbiology* 72:5069), with consensus annotations from RDP (Cole et al. (2007) *Nucl. Acids Res.* 35:D169) and NCBI taxonomies (D. L. Wheeler et al. (2000) *Nucl. Acids Res.* 28:10). Phylogenetic trees were constructed using the neighbor-joining algorithm in ARB (W. Ludwig et al. (2004) *Nucl. Acids Res.* 32:1363) using the Greengenes aligned 16S rDNA database. Placement in the tree was confirmed by comparing automated Greengenes taxonomy to the annotated taxonomies of nearest neighbors of each sequence in the aligned database. Branches of the tree are color-coded by bacterial orders, and clonal isolates represented as squares. Accession numbers of certain of these bacterial isolates that have been deposited are from EU515334 to EU515623 (GenBank), and are hereby incorporated by reference in their entirety.

Phylogenetic profiling of the clonal isolates (See Example II) revealed a diverse set of species in the Proteobacteria (87%), Actinobacteria (7%) and Bacteroidetes (6%) (FIG. 2 and FIG. S2). These phyla all include many clinically relevant pathogens. Of the eleven orders represented, Burkholderiales constitute 41% of the species isolated. The other major orders (>5%) are: Pseudomonadales (24%), Enterobacteriales (13%), Actinomycetales (7%), Rhizobiales (7%), and Sphingobacteriales (6%).

Without intending to be bound by scientific theory, one explanation for the widespread catabolism of both natural and synthetic antibiotics may relate to their organic sub-structures which are found in nature. Metabolic mechanisms exist for processing those sub-structures and may allow for the utilization of the parent synthetic antibiotic molecule. It is interesting that more than half of the bacterial isolates identified in this study belong to the orders Burkholderiales and Pseudomonadales. Organisms in these orders typically have large genomes of approximately 6-10 megabases, which has been suggested to be positively correlated to their metabolic diversity and multiple antibiotic resistance (Projan (2007) *Antimicrobial Agents and Chemotherapy* 51:1133). These organisms can be thought of as scavengers, capable of utilizing a large variety of single carbon sources as food (Parke and Gurian-Sherman (2001) *Annual Review of Phytopathology* 39:225).

Figure 3:
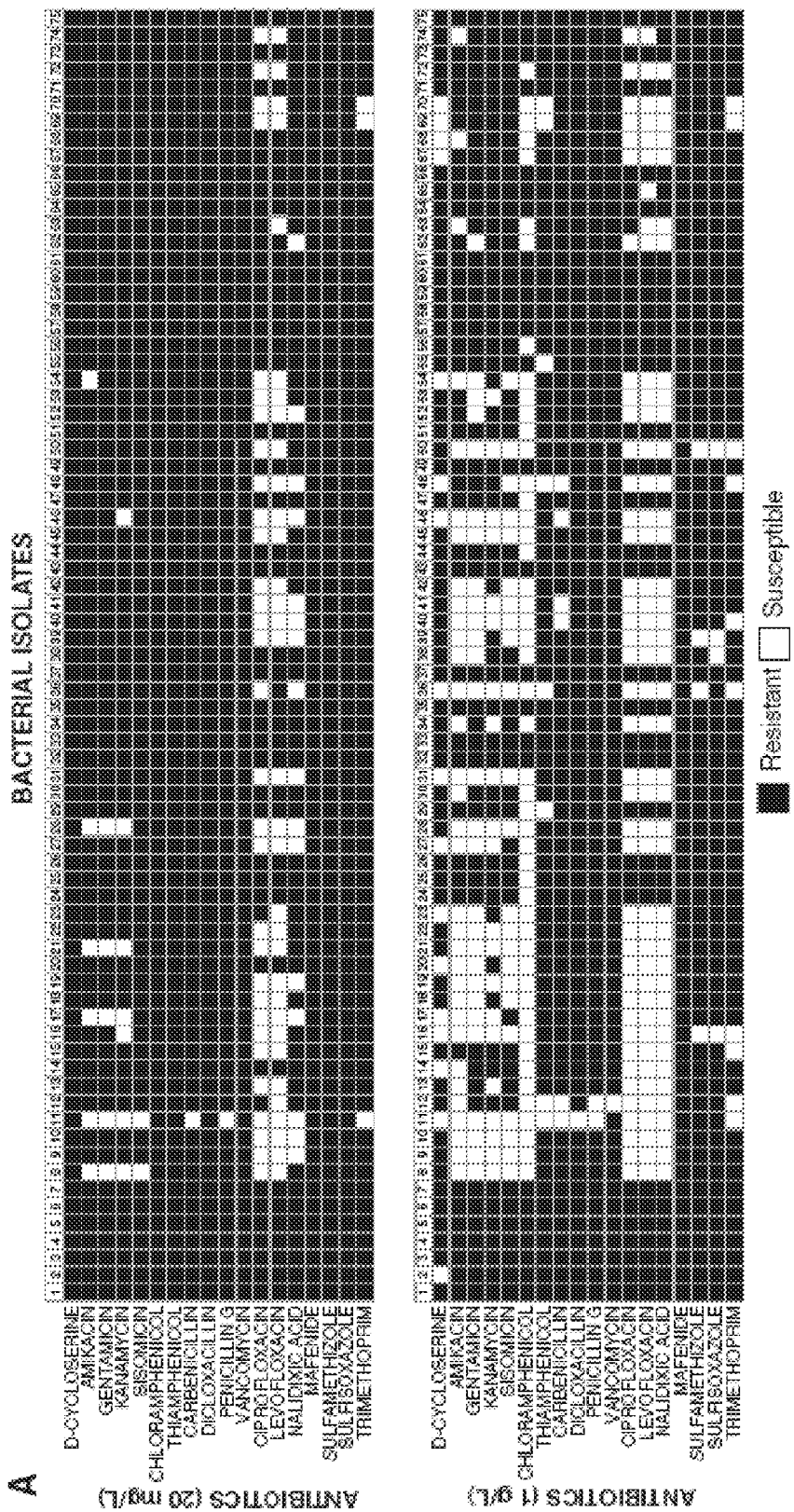
FIGS. 3A-3C graphically depict antibiotic resistance profiling of 75 clonal isolates capable of subsisting on antibiotics. (A) Heat map illustrating the resistance profiles of a representative subset of 75 clonal isolates capable of utilizing antibiotics as sole carbon source (Table 3). Resistance was determined as growth after 4 days at 22° C. in Luria Broth media containing 20 mg/liter antibiotic (top panel) and 1 g/liter antibiotic (bottom panel). (B) Percentage of clonal isolates resistant to each of the 18 antibiotics. Antibiotics are color coded by class, the full height of each bar corresponds to the percentage of clonal isolates resistant at 20 mg/liter and the solid colored section of each bar corresponds to the percentage of clonal isolates resistant at 1 g/liter. (C) Histogram depicting the distribution of the number of antibiotics that the clonal isolates were resistant to at 20 mg/liter (top panel) and 1 g/liter (bottom panel).
Figure 3:
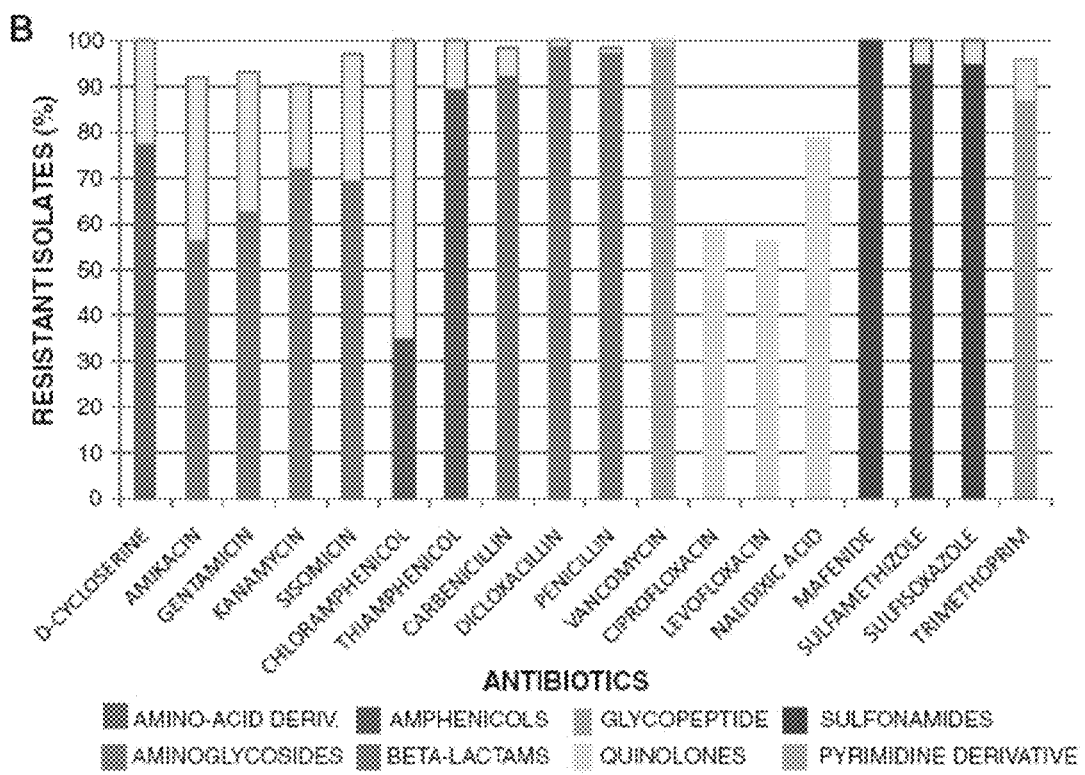
Figure 3:
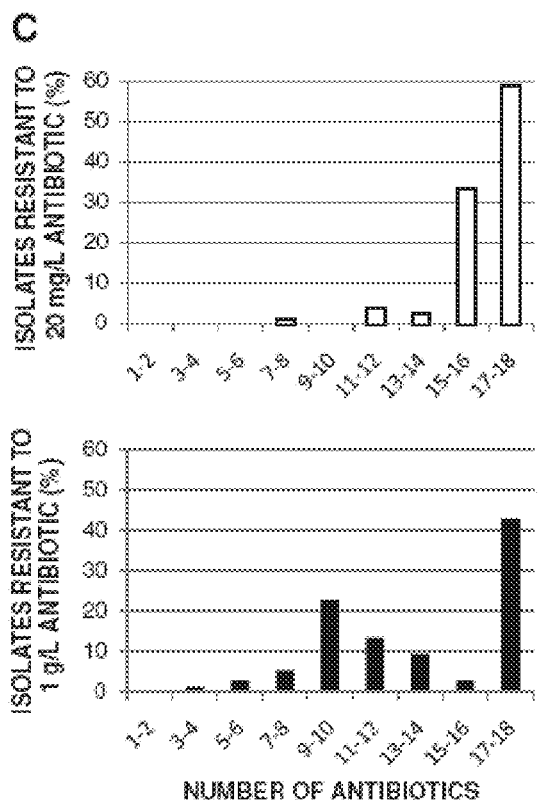

The magnitude of antibiotic resistance for a representative subset of 75 clonal isolates was determined (Table 3). Each clonal isolate was tested for resistance towards all 18 antibiotics used in the subsistence experiments at 20 mg/L and 1 g/L in rich media (See Example II). The clonal isolates tested on average were resistant to 17 out of 18 antibiotics at 20 mg/L, and 14 out of 18 antibiotics at 1 g/L (FIG. 3). Furthermore, for 74 of the 75 isolates, it was determined that if a bacterial isolate was able to subsist on an antibiotic, it was also resistant to all antibiotics in that class at 20 mg/L.

Previous work showing that strains from the genus *Streptomyces* are on average resistant to 7-8 antibiotics at 20 mg/L has highlighted the importance of producer organisms as a reservoir of antibiotic resistance (D'Costa et al. (2006) *Science* 311:374). Here bacteria subsisting on antibiotics are described as a substantial addition to the antibiotic resistome in terms of both phylogenetic diversity and prevalence of resistance. The bacteria isolated and described herein are 'super resistant,' since they tolerate concentrations of antibiotics>1 g/L which are 50-fold higher than the antibiotic concentrations used to define the antibiotic resistome. Id.

Greengenes (DeSantis et al. (2006) *Applied and Environmental Microbiology* 72:5069) identified isolates among the bacteria subsisting on antibiotics that are closely related to known pathogens e.g., members of the *Burkholderia cepacia* complex, and *Serratia marcescens*. In principle, relatedness allows for easier transfer of genetic material, since codon usage, promoter binding sites and other transcriptional and translational motifs are likely to be similar. It is therefore possible that pathogenic microbes can more readily use resistance genes originating from bacteria subsisting on antibiotics compared to the resistance genes from more distantly related antibiotic producer organisms.

To date, there have been no reports describing antibiotic catabolism in pathogenic strains. However, since most sites of serious infection in the human body are not carbon source limited it is unlikely that pathogenic microbes would have a strong selective advantage by catabolizing antibiotics compared to just resisting them, so it is likely that only the resistance conferring part of the catabolic machinery would be selected for in pathogenic strains.

In addition to the finding that bacteria subsisting on natural and synthetic antibiotics are widely distributed in the environment, these results highlight an unrecognized reservoir of multiple antibiotic resistance machinery. Bacteria subsisting on antibiotics are phylogenetically diverse, and include many organisms closely related to clinically relevant pathogens. It is thus possible that pathogens could obtain antibiotic resistance genes from environmentally distributed super-resistant microbes subsisting on antibiotics.

References

Riesenfeld et al. (2004) Environmental Microbiology 6:981
Walsh (2000) *Nature* 406:775
Alekshun and Levy (2007) *Cell* 128:1037
Fredrickson et al. (2000) *Applied and Environmental Microbiology* 66:2006
McAllister et al. (1996) *Biodegradation* 7:1
Kameda et al. (1961) *Nature* 191:1122
Abd-El-Malek et al. (1961) *Nature* 189:775
Cole et al. (2007) *Nucleic Acids Res* 35:D169
Wheeler et al. (2000) *Nucleic Acids Res* 28:10
Ludwig et al. (2004) *Nucleic Acids Res* 32:1363

EXAMPLE II

Materials and Methods

Growth Media

All liquid media used for isolating bacteria capable of subsisting on antibiotics was made by dissolving 1 g/L of the relevant antibiotics (Table 1, which depicts lot purities of antibiotics used, as reported on Certificates of Analysis from Sigma-Aldrich) into single carbon source (SCS) media containing 5 g $(NH_4)_2SO_4$, 3 g $KH_2PO_4$, 0.5 g $MgSO_4.7H_2O$, 15 mg EDTA, 4.5 mg $ZnSO_4.7H_2O$, 4.5 mg $CaCl_2.2H_2O$, 3 mg $FeSO_4.7H_2O$, 1 mg $MnCl_2.4H_2O$, 1 mg $H_3BO_3$, 0.4 mg $Na_2MoO_4.2H_2O$, 0.3 mg $CuSO_4.5H_2O$, 0.3 mg $CoCl_2.6H_2O$ and 0.1 mg KI per liter water. The pH was adjusted to 5.5 using HCl, and the media was sterilized through a 0.22 μm filter. Solid medium was prepared by adding 15 g agar per liter of liquid SCS media followed by autoclaving before adding antibiotics.

TABLE 1

| Antibiotics | Lot Purity % |
|---|---|
| Ciprofloxacin | 98.5 |
| Levofloxacin | 100.0 |
| Sisomicin | 99 |
| Gentamicin | NR |
| Kanamycin | NR |
| Amikacin | 100 |
| Penicillin G | 99.7 |
| Carbenicillin | 92.9 |
| Dicloxacillin | 99.8 |
| Chloramphenicol | >99 |
| Nalidixic acid | 100 |
| Thiamphenicol | >99 |
| Sulfisoxazole | 99.7 |
| Trimethoprim | 100 |
| Mafenide | 100 |
| Sulfamethizole | 99.9 |
| D-Cycloserine | 98 |
| Vancomycin | NR |

NR, not reported.

All liquid media used for resistance profiling was made by dissolving 20 mg/L or 1 g/L of the relevant antibiotics into autoclaved Luria broth containing 5 g Yeast Extract, 10 g NaCl and 10 g of tryptone in 1 Liter of water. The pH was adjusted to 5.5 using HCl, and the media was sterilized through a 0.22 µm filter.

Culturing of Environmental Bacteria Capable of Subsisting on Antibiotics

Initial soil microbial inocula (soil description in Table 2, which depicts soil information for the 11 different soils from which bacteria capable of subsisting on antibiotics were isolated) were prepared in minimal medium containing no carbon, and inoculated into SCS-antibiotic media (corresponding to approximately 125 mg of dissolved soil in 5 mL of media). To significantly reduce the transfer of residual alternative carbon sources present in original inocula, samples were passaged (2.5 µL) into fresh SCS-antibiotic media (5 mL) two additional times after 7 days of growth, resulting in a $5 \times 10^4$ dilution at each passage (resulting in a final carryover of approximately 30 ng of soil in 5 mL of media at the third passage). Clonal isolates from the liquid cultures were obtained by plating cultures out on SCS-antibiotic agar medium and resulting single colonies were picked and re-streaked on corresponding plates. Three colonies each were then inoculated into fresh SCS-antibiotic liquid media (5 mL) to confirm clonal phenotype. Final culture growth was recorded after 1 month incubation without shaking at 22° C. and cultures with at least $10^8$ cells/mL were assayed as positive growth.

TABLE 2

| FIG. 1A identifiers | Soil type | Soil name | Soil collection location |
|---|---|---|---|
| F1 | Farmland | S1G | Corn Field with Antibiotic Treated Manure, Great Brook Farm, Carlisle, MA |
| F2 | Farmland | S1N | Alfalfa Field with Manure Treatment, Northcroft Farm, Pelican Rapids, MN |
| F3 | Farmland | S2N | Alfalfa Field without Manure Treatment, Northcroft Farm, Pelican Rapids, MN |
| P1 | Pristine | S2R | Raccoon Ledger, Rockport, MA |
| P2 | Pristine | S3N | Prairie next to Northcroft Farm, Pelican Rapids, MN |
| P3 | Pristine | S1R | Brier's Swamp, Rockport, MA |
| P4 | Pristine | S1A | Pristine Forest Soil, Alan Seeger Natural Area, PA |
| P5 | Pristine | S2T | Untreated Forested Area, Toftrees State Gameland Area, PA |
| U1 | Urban | S1T | Waste Water Treated Area, Toftrees State Gameland Area, PA |
| U2 | Urban | S3F | Boston Fens, MA |
| U3 | Urban | S1P | Boston Public Garden, MA |

Since inoculation in media lacking a carbon source (no carbon control) did not show growth in any cases, carbon source contamination of the source media or carbon fixation from the air were considered insignificant to this experiment. The only other alternative carbon substrate for growth could be impurities in the antibiotic stocks. All antibiotics used were purchased from Sigma-Aldrich at the highest purities available. Lot purities of each compound used are listed in Table 1. Based on an average carbon mass of $0.15 \times 10^{-12}$ g per bacterial cell, it was estimated that at least 15 µg of carbon must be incorporated into bacterial biomass to reach sufficient culture densities in 1 mL of culture to be rated as successful growth. Assuming 50% carbon content of impurities, and under the most stringent assumptions of (1) 100% incorporation of carbon impurities into biomass, and (2) no loss of carbon as metabolic byproducts (such as $CO_2$), antibiotics with greater than 97% purity would have insufficient impurities to support sole carbon source growth. Of the antibiotic lots used in this experiment (Table 1), twelve compound stocks are at least 99% pure, two compounds (ciprofloxacin and D-cycloserine) have between 98 and 98.5% purity, one compound (carbenicillin) is 92.9% pure, and no purity information is available for three compounds (kanamycin, gentamicin, and vancomycin).

Phylogenetic Profiling

The 16S ribosomal DNA (rDNA) of each of the clonal isolates identified in this study was amplified using universal bacterial 16S primers:

```
>Bact_63f_62C
5'- CAG GCC TAA CAC ATG CAA GTC -3'   (SEQ ID NO: 1)

>Bact_1389r_63C
5'- ACG GCC GGT GTG TAC AAG -3'       (SEQ ID NO: 2)
```

Successful 16S rDNA amplicons were sequenced for phylogenetic profiling. High-quality, non-chimeric sequences were classified using Greengenes (DeSantis et al. (2006) Nucleic Acids Res 34:W394; DeSantis et al. (2006) Applied and Environmental Microbiology 72:5069), with consensus annotations from RDP (Cole et al. (2007) Nucleic Acids Res 35:D169) and NCBI taxonomies (Wheeler et al. (2000) Nucleic Acids Res 28: 10). Phylogenetic trees were constructed using the neighbor-joining algorithm in ARB (Ludwig et al. (2004) Nucleic Acids Res 32:1363) using the Greengenes aligned 16S rDNA database. Placement in the tree was confirmed by comparing automated Greengenes taxonomy to the annotated taxonomies of nearest neighbors of each sequence in the aligned database.

Resistance Profiling of 75 Representative Isolates Capable of Subsisting on Antibiotics 75 clonal isolates (Table 3, which lists strain information for the 75 clonal isolates used for resistance profiles) were selected to include multiple isolates capable of subsisting on each of the 18 antibiotics and originating from each of the 11 soils (Table 2). Bacterial cultures were inoculated into Luria Broth from frozen glycerol stocks and were incubated at 22° C. for 3 days. 500 nL of this culture was used to inoculate each of the clonal isolates into 200 uL of Luria Broth containing one of the eighteen different antibiotics (See Table 1) at 20 mg/L and 1 g/L. Cultures were incubated without shaking at 22° C. for 4 days. Resistance of an isolate was determined by turbidity at 600 nm using a Versamax microplate reader from Molecular Devices.

TABLE 3

| FIG. 3A identifier | Strain name | Subsisting on | From soil |
|---|---|---|---|
| 1 | Levo-S2T-M1LLLSSL-2 | Levofloxacin | S2T |
| 2 | Kana-S2T-M1LLLSSL-3 | Kanamycin | S2T |
| 3 | Amik-S2T-M1LLLSSL-1 | Amikacin | S2T |
| 4 | Carb-S2T-M1LLLSSL-1 | Carbenicillin | S2T |
| 5 | Chlo-S2T-M1LLLSSL-2 | Chloramphenicol | S2T |
| 6 | Nali-S2T-M1LLLSSL-1 | Nalidixic acid | S2T |
| 7 | Thia-S2T-M1LLLSSL-2 | Thiamphenicol | S2T |
| 8 | Trim-S2T-M1LLLSSL-1 | Trimethoprim | S2T |
| 9 | Mafe-S2T-M1LLLSSL-3 | Mafenide | S2T |
| 10 | Cycl-S2T-M1LLLSSL-3 | D-Cycloserine | S2T |
| 11 | Vanc-S2T-M1LLLSSL-3 | Vancomycin | S2T |
| 12 | Siso-S2N-M1LLLSSL-1 | Sisomycin | S2N |
| 13 | Gent-S2N-M1LLLSSL-2 | Gentamycin | S2N |
| 14 | Kana-S2N-M1LLLSSL-2 | Kanamycin | S2N |
| 15 | Peni-S2N-M1LLLSSL-2 | Penicillin G | S2N |
| 16 | Dicl-S2N-M1LLLSSL-1 | Dicloxacillin | S2N |
| 17 | Trim-S2N-M1LLLSSL-1 | Trimethoprim | S2N |
| 18 | Vanc-S2N-M1LLLSSL-1 | Vancomycin | S2N |
| 19 | Dicl-S3N-M1LLLSSL-2 | Dicloxacillin | S3N |
| 20 | Thia-S3N-M1LLLSSL-3 | Thiamphenicol | S3N |
| 21 | Trim-S3N-M1LLLSSL-2 | Trimethoprim | S3N |
| 22 | Mafe-S3N-M1LLLSSL-2 | Mafenide | S3N |
| 23 | Vanc-S3N-M1LLLSSL-2 | Vancomycin | S3N |
| 24 | Cipr-S1P-M1LLLSSL-3 | Ciprofloxacin | S1P |
| 25 | Peni-S1P-M1LLLSSL-2 | Penicillin G | S1P |
| 26 | Chlo-S1P-M1LLLSSL-1 | Chloramphenicol | S1P |
| 27 | Thia-S1P-M1LLLSSL-1 | Thiamphenicol | S1P |
| 28 | Trim-S1P-M1LLLSSL-3 | Trimethoprim | S1P |
| 29 | Slfm-S1P-M1LLLSSL-1 | Sulfamethizole | S1P |
| 30 | Cycl-S1P-M1LLLSSL-1 | D-Cycloserine | S1P |
| 31 | Vanc-S1P-M1LLLSSL-3 | Vancomycin | S1P |
| 32 | Cipr-S1T-M1LLLSSL-2 | Ciprofloxacin | S1T |
| 33 | Levo-S1T-M1LLLSSL-1 | Levofloxacin | S1T |
| 34 | Siso-S1T-M1LLLSSL-1 | Sisomycin | S1T |
| 35 | Carb-S1T-M1LLLSSL-1 | Carbenicillin | S1T |
| 36 | Dicl-S1T-M1LLLSSL-1 | Dicloxacillin | S1T |
| 37 | Chlo-S1T-M1LLLSSL-1 | Chloramphenicol | S1T |
| 38 | Thia-S1T-M1LLLSSL-3 | Thiamphenicol | S1T |
| 39 | Trim-S1T-M1LLLSSL-2 | Trimethoprim | S1T |
| 40 | Mafe-S1T-M1LLLSSL-1 | Mafenide | S1T |
| 41 | Cycl-S1T-M1LLLSSL-2 | D-Cycloserine | S1T |
| 42 | Vanc-S1T-M1LLLSSL-1 | Vancomycin | S1T |
| 43 | Levo-S3F-M1LLLSSL-3 | Levofloxacin | S3F |
| 44 | Slfs-S3F-M1LLLSSL-3 | Sulfisoxazole | S3F |
| 45 | Trim-S3F-M1LLLSSL-1 | Trimethoprim | S3F |
| 46 | Mafe-S3F-M1LLLSSL-3 | Mafenide | S3F |
| 47 | Slfm-S3F-M1LLLSSL-3 | Sulfamethizole | S3F |
| 48 | Vanc-S3F-M1LLLSSL-2 | Vancomycin | S3F |
| 49 | Amik-S1R-M1LLLSSL-3 | Amikacin | S1R |
| 50 | Peni-S1R-M1LLLSSL-2 | Penicillin G | S1R |
| 51 | Mafe-S1R-M1LLLSSL-2 | Mafenide | S1R |
| 52 | Vanc-S1R-M1LLLSSL-2 | Vancomycin | S1R |
| 53 | Trim-S1N-M1LLLSSL-1 | Trimethoprim | S1N |
| 54 | Vanc-S1N-M1LLLSSL-1 | Vancomycin | S1N |
| 55 | Kana-S1A-M1LLLSSL-2 | Kanamycin | S1A |
| 56 | Carb-S1A-M1LLLSSL-2 | Carbenicillin | S1A |
| 57 | Slfs-S1A-M1LLLSSL-1 | Sulfisoxazole | S1A |
| 58 | Vanc-S1A-M1LLLSSL-1 | Vancomycin | S1A |
| 59 | Kana-S2R-M1LLLSSL-2 | Kanamycin | S2R |
| 60 | Amik-S2R-M1LLLSSL-3 | Amikacin | S2R |
| 61 | Peni-S2R-M1LLLSSL-2 | Penicillin G | S2R |
| 62 | Dicl-S2R-M1LLLSSL-1 | Dicloxacillin | S2R |
| 63 | Mafe-S2R-M1LLLSSL-2 | Mafenide | S2R |

TABLE 3-continued

| FIG. 3A identifier | Strain name | Subsisting on | From soil |
|---|---|---|---|
| 64 | Slfm-S2R-M1LLLSSL-1 | Sulfamethizole | S2R |
| 65 | Cipr-S1G-M1LLLSSL-1 | Ciprofloxacin | S1G |
| 66 | Levo-S1G-M1LLLSSL-1 | Levofloxacin | S1G |
| 67 | Gent-S1G-M1LLLSSL-3 | Gentamycin | S1G |
| 68 | Kana-S1G-M1LLLSSL-1 | Kanamycin | S1G |
| 69 | Peni-S1G-M1LLLSSL-1 | Penicillin G | S1G |
| 70 | Carb-S1G-M1LLLSSL-3 | Carbenicillin | S1G |
| 71 | Chlo-S1G-M1LLLSSL-3 | Chloramphenicol | S1G |
| 72 | Nali-S1G-M1LLLSSL-2 | Nalidixic acid | S1G |
| 73 | Thia-S1G-M1LLLSSL-1 | Thiamphenicol | S1G |
| 74 | Slfs-S1G-M1LLLSSL-3 | Sulfisoxazole | S1G |
| 75 | Mafe-S1G-M1LLLSSL-2 | Mafenide | S1G |

Analysis of Antibiotic Removal of Penicillin and Carbenicillin Subsisting Bacteria Representative isolates capable of growth on penicillin and carbenicillin as sole carbon source were selected for analysis of antibiotic removal from the growth media by High Performance Liquid Chromatography (HPLC). 2 µL of these cultures were re-inoculated into fresh SCS-antibiotic medium (5 mL) and allowed to grow for 28 days. Samples of the cultures and un-inoculated media controls were taken at regular intervals throughout the 28 day period and the catabolism of penicillin and carbenicillin was monitored at 214 nm by HPLC of filtered media from samples using a Hewlett Packard 1090 Liquid Chromatograph and a Vydac C-18 column. HPLC was performed at a flow rate of 0.3 mL/min with an acetonitrile gradient going from 5% to 65% in 30 minutes in the presence of 0.1% trifluoroacetic acid.

The HPLC chromatogram of the penicillin catabolizing culture medium (FIG. 1B) started out with a single peak corresponding to the penicillin peak of the un-inoculated control. This peak disappeared at day 4 with the appearance of multiple smaller peaks at lower elution times; by day 20 these peaks had also disappeared in agreement with the complete catabolism of penicillin by the culture in 20 days. In comparison, the single penicillin peak in the un-inoculated control remained the dominant peak over the same time course. The HPLC chromatogram of the medium from the carbenicillin catabolizing culture (FIG. 1B) started out with a bimodal peak corresponding to the un-inoculated carbenicillin control, which remained stable for 2 days. At day 4, corresponding to the appearance of visible turbidity in the inoculated culture, the bimodal peak had almost disappeared and secondary peaks at lower elution times were observed. These secondary peaks almost completely disappeared by the 28th day, suggesting that carbenicillin was almost completely catabolized within 28 days. The bimodal carbenicillin peak remained relatively unchanged in the un-inoculated control over the same time course.

Figure 6:
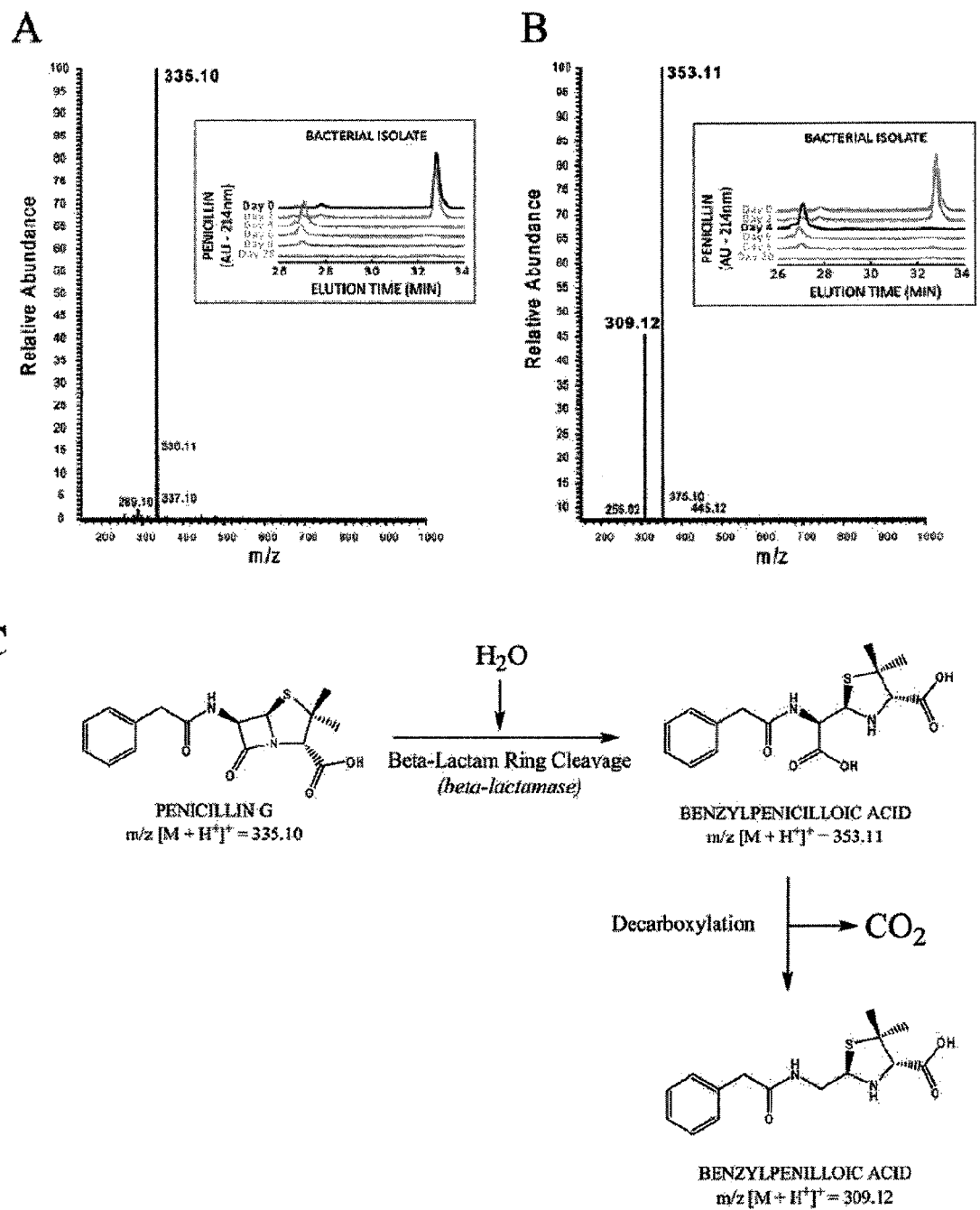
FIGS. 6A-6C depict mass spectrometry analysis of growth media from penicillin subsisting bacterial culture. (A) Mass spectra of day 0 growth media from penicillin culture with a major peak at m/z of 335.10 corresponding exactly to the protonated penicillin G molecule. (B) Mass spectra of day 4 growth media from penicillin culture with two major peaks at m/z values 353.11 and 309.12 corresponding to protonated benzylpenicilloic acid and benzylpenilloic acid, respectively. (C) First steps of a proposed penicillin G degradation pathway.

Samples from the penicillin subsisting culture from day 0 and day 4 were prepared for LC/MS using a Waters Sep-Pak Cartridge prior to mass spectrometry analysis using a LTQ-FT from Thermo Electron. Mass spectra were analyzed using XCalibur 2.0.5 and the empirically determined m/z values of all major peaks were compared to predicted m/z values of putative penicillin degradation products calculated using ChemDraw Ultra 9.0 (FIGS. 6A-6C).

What is claimed is:

1. A method of reducing a level of one or more antibiotics from an antibiotic-contaminated substance comprising culturing a bacterium that can utilize the one or more antibiotics as a carbon source in the presence of the antibiotic-contaminated substance for a sufficient amount of time to reduce the level of one or more antibiotics from the antibiotic-contaminated substance wherein the one or more antibiotics is a sulfonamide, quinolone, glycopeptide, amphenicol, or aminoglycoside.

2. The method of claim 1, wherein the antibiotic-contaminated substance is selected from the group consisting of contaminated soil, contaminated water and a contaminated work surface.

3. The method of claim 2, wherein the contaminated work surface is present in a hospital, a clinic or a laboratory.

4. The method of claim 1, wherein the one or more antibiotics are used by the bacterium as a sole carbon source.

5. The method of claim 1, wherein the bacterium has a 16S nucleic acid sequence comprising a GenBank Accession Number selected from the group consisting of EU515334, EU515335, EU515336, EU515337, EU515338, EU515339, EU515400, EU515401, EU515402, EU515403, EU515404, EU515405, EU515406, EU515407, EU515408, EU515409, EU515410, EU515411, EU515412, EU515413, EU515414, EU515415, EU515416, EU515417, EU515418, EU515419, EU515420, EU515421, EU515422, EU515423, EU515424, EU515425, EU515426, EU515427, EU515428, EU515429, EU515430, EU515431, EU515432, EU515433, EU515434, EU515435, EU515436, EU515437, EU515438, EU515439, EU515440, EU515441, EU515442, EU515443, EU515444, EU515445, EU515446, EU515447, EU515448, EU515449, EU515450, EU515451, EU515452, EU515453, EU515454, EU515455, EU515456, EU515457, EU515458, EU515459, EU515460, EU515461, EU515462, EU515463, EU515464, EU515465, EU515466, EU515467, EU515468, EU515469 EU515470, EU515471, EU515472, EU515473, EU515474, EU515475, EU515476, EU515477, EU515478, EU515479, EU515480, EU515481, EU515482, EU515483, EU515484, EU515485, EU515486, EU515487, EU515488, EU515489, EU515490, EU515491, EU515492, EU515493, EU515494, EU515495, EU515496, EU515497, EU515498, EU515499, EU515500, EU515501, EU515502, EU515503, EU515504, EU515505, EU515506, EU515507, EU515508, EU515509, EU515510, EU515511, EU515512, EU515513, EU515514, EU515515, EU515516, EU515517, EU515518, EU515519, EU515520, EU515521, EU515522, EU515523, EU515524, EU515525, EU515526, EU515527, EU515528, EU515529, EU515530, EU515531, EU515532, EU515533, EU515534, EU515535, EU515536, EU515537, EU515538, EU515539, EU515540, EU515541, EU515542, EU515543, EU515544, EU515545, EU515546, EU515547, EU515548, EU515549, EU515550, EU515551, EU515552, EU515553, EU515554, EU515555, EU515556, EU515557, EU515558, EU515559, EU515560, EU515561, EU515562, EU515563, EU515564, EU515565, EU515566, EU515567, EU515568, EU515569, EU515570, EU515571, EU515572, EU515573, EU515574, EU515575, EU515576, EU515577, EU515578, EU515579, EU515580, EU515581, EU515582, EU515583, EU515584, EU515585, EU515586, EU515587, EU515588, EU515589, EU515590, EU515591, EU515592, EU515593, EU515594, EU515595, EU515596, EU515597, EU515598, EU515599, EU515600, EU515601, EU515602, EU515603, EU515604, EU515605, EU515606, EU515607, EU515608, EU515609, EU515610, EU515611, EU515612, EU515613, EU515614, EU515615, EU515616, EU515617, EU515618, EU515619, EU515620, EU515621, EU515622 and EU515623.

6. A method of reducing a level of one or more antibiotic from an antibiotic-contaminted substance comprising culture a bacterium that can utilize the one or more antibiotics as a carbon source in the presence of the antibiotic-contaminated substance for a sufficient amount of time to reduce the level of one or more antibiotics from the antibiotic-contaminated substance, wherein the one or more antibiotics is chloramphenicol, vancomycin, carbenicillin, ciprofloxacin, mafenide, kanamycin, sisomicin, amikacin, trimethropin, D-cycloserine, gentamicin, dicloxacillin, nalidixic acid, thiamphenicol, levofloxacin, sulfemethizole or sulfisoxazole.

7. The method of claim 6, wherein the bacterium has a 16S nucleic acid sequence comprising a GenBank Accession Number selected from the group consisting of EU515334, EU515335, EU515336, EU515337, EU515338, EU515339, EU515400, EU515401, EU515402, EU515403, EU515404, EU515405, EU515406, EU515407, EU515408, EU515409, EU515410, EU515411, EU515412, EU515413, EU515414, EU515415, EU515416, EU515417, EU515418, EU515419, EU515420, EU515421, EU515422, EU515423, EU515424, EU515425, EU515426, EU515427, EU515428, EU515429, EU515430, EU515431, EU515432, EU515433, EU515434, EU515435, EU515436, EU515437, EU515438, EU515439, EU515440, EU515441, EU515442, EU515443, EU515444, EU515445, EU515446, EU515447, EU515448, EU515449, EU515450, EU515451, EU515452, EU515453, EU515454, EU515455, EU515456, EU515457, EU515458, EU515459, EU515460, EU515461, EU515462, EU515463, EU515464, EU515465, EU515466, EU515467, EU515468, EU515469 EU515470, EU515471, EU515472, EU515473, EU515474, EU515475, EU515476, EU515477, EU515478, EU515479, EU515480, EU515481, EU515482, EU515483, EU515484, EU515485, EU515486, EU515487, EU515488, EU515489, EU515490, EU515491, EU515492, EU515493, EU515494, EU515495, EU515496, EU515497, EU515498, EU515499, EU515500, EU515501, EU515502, EU515503, EU515504, EU515505, EU515506, EU515507, EU515508, EU515509, EU515510, EU515511, EU515512, EU515513, EU515514, EU515515, EU515516, EU515517, EU515518, EU515519, EU515520, EU515521, EU515522, EU515523, EU515524, EU515525, EU515526, EU515527, EU515528, EU515529, EU515530, EU515531, EU515532, EU515533, EU515534, EU515535, EU515536, EU515537, EU515538, EU515539, EU515540, EU515541, EU515542, EU515543, EU515544, EU515545, EU515546, EU515547, EU515548, EU515549, EU515550, EU515551, EU515552, EU515553, EU515554, EU515555, EU515556, EU515557, EU515558, EU515559, EU515560, EU515561, EU515562, EU515563, EU515564, EU515565, EU515566, EU515567, EU515568, EU515569, EU515570, EU515571, EU515572, EU515573, EU515574, EU515575, EU515576, EU515577, EU515578, EU515579, EU515580, EU515581, EU515582, EU515583, EU515584, EU515585, EU515586, EU515587, EU515588, EU515589, EU515590, EU515591, EU515592, EU515593, EU515594, EU515595, EU515596, EU515597, EU515598, EU515599, EU515600, EU515601, EU515602, EU515603, EU515604, EU515605, EU515606, EU515607, EU515608, EU515609, EU515610, EU515611, EU515612, EU515613, EU515614, EU515615, EU515616, EU515617, EU515618, EU515619, EU515620, EU515621, EU515622 and EU515623.

8. A method of eliminating one or more antibiotics from an antibiotic-contaminated substance, comprising culturing a bacterium in the presence of the antibiotic-contaminated substance for a sufficient amount of time to eliminate the one or more antibiotics from the antibiotic-contaminated substance wherein the one or more antibiotics is a sulfonamide, quinolone, glycopeptide, amphenicol, or aminoglycoside and wherein the bacterium has a 16S nucleic acid sequence comprising a GenBank Accession Number selected from the group consisting of EU515334, EU515335, EU515336, EU515337, EU515338, EU515339, EU515400, EU515401, EU515402, EU515403, EU515404, EU515405, EU515406, EU515407, EU515408, EU515409, EU515410, EU515411, EU515412, EU515413, EU515414, EU515415, EU515416, EU515417, EU515418, EU515419, EU515420, EU515421, EU515422, EU515423, EU515424, EU515425, EU515426, EU515427, EU515428, EU515429, EU515430, EU515431, EU515432, EU515433, EU515434, EU515435, EU515436, EU515437, EU515438, EU515439, EU515440, EU515441, EU515442, EU515443, EU515444, EU515445, EU515446, EU515447, EU515448, EU515449, EU515450, EU515451, EU515452, EU515453, EU515454, EU515455, EU515456, EU515457, EU515458, EU515459, EU515460, EU515461, EU515462, EU515463, EU515464, EU515465, EU515466, EU515467, EU515468, EU515469 EU515470, EU515471, EU515472, EU515473, EU515474, EU515475, EU515476, EU515477, EU515478, EU515479, EU515480, EU515481, EU515482, EU515483, EU515484, EU515485, EU515486, EU515487, EU515488, EU515489, EU515490, EU515491, EU515492, EU515493, EU515494, EU515495, EU515496, EU515497, EU515498, EU515499, EU515500, EU515501, EU515502, EU515503, EU515504, EU515505, EU515506, EU515507, EU515508, EU515509, EU515510, EU515511, EU515512, EU515513, EU515514, EU515515, EU515516, EU515517, EU515518, EU515519, EU515520, EU515521, EU515522, EU515523, EU515524, EU515525, EU515526, EU515527, EU515528, EU515529, EU515530, EU515531, EU515532, EU515533, EU515534, EU515535, EU515536, EU515537, EU515538, EU515539, EU515540, EU515541, EU515542, EU515543, EU515544, EU515545, EU515546, EU515547, EU515548, EU515549, EU515550, EU515551, EU515552, EU515553, EU515554, EU515555, EU515556, EU515557, EU515558, EU515559, EU515560, EU515561, EU515562, EU515563, EU515564, EU515565, EU515566, EU515567, EU515568, EU515569, EU515570, EU515571, EU515572, EU515573, EU515574, EU515575, EU515576, EU515577, EU515578, EU515579, EU515580, EU515581, EU515582, EU515583, EU515584, EU515585, EU515586, EU515587, EU515588, EU515589, EU515590, EU515591, EU515592, EU515593, EU515594, EU515595, EU515596, EU515597, EU515598, EU515599, EU515600, EU515601, EU515602, EU515603, EU515604, EU515605, EU515606, EU515607, EU515608, EU515609, EU515610, EU515611, EU515612, EU515613, EU515614, EU515615, EU515616, EU515617, EU515618, EU515619, EU515620, EU515621, EU515622 and EU515623.

9. The method of claim 8, wherein the one or more antibiotics are used by the bacterium as a sole carbon source.

10. The method of claim 8, wherein the antibiotic-contaminated substance is selected from the group consisting of contaminated soil, contaminated water and a contaminated work surface.

11. The method of claim 10, wherein the contaminated work surface is present in a hospital, a clinic or a laboratory.

12. A method of eliminating one or more antibiotics from an antibiotic-contaminated substance, comprising culturing a bacterium in the presence of the antibiotic-contaminated substance for a sufficient amount of time to eliminate the one or more antibiotics from the antibiotic-contaminated substance wherein the one or more antibiotics are selected from the group consisting of chloramphenicol, vancomycin, carbenicillin, ciprofloxacin, mafenide, kanamycin, sisomicin, amikacin, trimethropin, D-cycloserine, gentamicin, dicloxacillin, nalidixic acid, thiamphenicol, levofloxacin, sulfamethizole and sulfisoxazole.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Amplification primer

<400> SEQUENCE: 1
caggcctaac acatgcaagt c                                             21

<210> SEQ ID NO 2
<211> LENGTH: 18
<212> TYPE: DNA
<213> ORGANISM: Artificial Sequence
<220> FEATURE:
<223> OTHER INFORMATION: Amplification primer

<400> SEQUENCE: 2
acgggcggtg tgtacaag                                                 18